(12) United States Patent
Wallace et al.

(10) Patent No.: US 11,708,361 B2
(45) Date of Patent: Jul. 25, 2023

(54) PROCESSES AND INTERMEDIATES FOR THE PREPARATION OF SOLUBLE GUANYLATE CYCLASE STIMULATORS

(71) Applicant: Cyclerion Therapeutics, Inc., Cambridge, MA (US)

(72) Inventors: Debra Jane Wallace, Lexington, MA (US); Fenger Zhou, Cambridge, MA (US); Yuguang Wang, Cambridge, MA (US); Takashi Nakai, Newton, MA (US); Vishnu Vardhan Reddy Karnati, Sudbury, MA (US); Wayne C. Schairer, Westboro, MA (US); William Kissel, Cambridge, MA (US); Song Xue, Newton, MA (US); Ahmad Hashash, Southborough, MA (US)

(73) Assignee: Cyclerion Therapeutics, Inc., Cambridge, MA (US)

( * ) Notice: Subject to any disclaimer, the term of this patent is extended or adjusted under 35 U.S.C. 154(b) by 0 days.

(21) Appl. No.: 17/497,352

(22) Filed: Oct. 8, 2021

(65) Prior Publication Data

US 2022/0024909 A1      Jan. 27, 2022

Related U.S. Application Data

(62) Division of application No. 16/961,109, filed as application No. PCT/US2019/013060 on Jan. 10, 2019, now Pat. No. 11,274,096.

(60) Provisional application No. 62/615,678, filed on Jan. 10, 2018.

(30) Foreign Application Priority Data

Feb. 22, 2018  (WO) ............... PCT/CN2018/076982

(51) Int. Cl.
*C07D 413/14*      (2006.01)
*C07D 403/04*      (2006.01)
*C07D 413/12*      (2006.01)

(52) U.S. Cl.
CPC ......... *C07D 413/14* (2013.01); *C07D 403/04* (2013.01); *C07D 413/12* (2013.01); *C07B 2200/13* (2013.01)

(58) Field of Classification Search
CPC ............... C07D 413/14; C07D 403/04
See application file for complete search history.

(56) References Cited

U.S. PATENT DOCUMENTS

| | | | |
|---|---|---|---|
| 9,481,689 B2 | 11/2016 | Nakai et al. | |
| 2017/0137439 A1 | 5/2017 | Nakai et al. | |
| 2017/0291889 A1 | 10/2017 | Barden et al. | |
| 2021/0053962 A1 | 2/2021 | Wallace et al. | |
| 2021/0284632 A1 | 9/2021 | Xue et al. | |
| 2021/0323951 A1 | 10/2021 | Xue et al. | |

FOREIGN PATENT DOCUMENTS

| | | |
|---|---|---|
| WO | 2016/044447 A1 | 3/2016 |
| WO | 2017/095697 A1 | 6/2017 |

OTHER PUBLICATIONS

U.S. Appl. No. 16/961,109, filed Jul. 9, 2020, 2021-0053962, Published.
Nakai et al., Discovery of IWP-051, a Novel Orally Bioavailable sGC Stimulator with Once-Daily Dosing Potential in Humans. ACS Med Chem Lett. Feb. 24, 2016;7(5):465-9.
International Search Report and Written Opinion for Application No. PCT/US2019/013060, dated Apr. 11, 2019, 10 pages.

*Primary Examiner* — Kamal A Saeed
(74) *Attorney, Agent, or Firm* — McCarter & English, LLP; Xin Zhang; Zhongyu "Alex" Wang

(57) ABSTRACT

The present disclosure relates to novel processes for the preparation of compounds of Formula I. Some of these compounds are useful as stimulators of soluble guanylate cyclase (sGC). Others are useful intermediates towards the preparation of said stimulators. These processes are amenable to large scale preparation and produce stable 3-(2-pyrimidinyl)pyrazoles of Formula I in high purity and yields. The present invention has the additional advantage of facile reaction conditions, amenable to scale up for large scale manufacturing. The disclosure also provides novel intermediates useful in the preparation of said compounds.

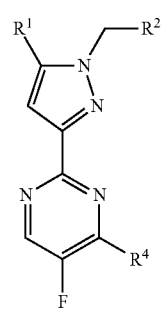

Formula I

14 Claims, 5 Drawing Sheets

PROCESSES AND INTERMEDIATES FOR THE PREPARATION OF SOLUBLE GUANYLATE CYCLASE STIMULATORS

RELATED APPLICATIONS

This Application is a divisional of U.S. patent application Ser. No. 16/961,109, filed Jul. 9, 2020, which is a 371 national phase of International Application No.: PCT/US2019/013060, filed on Jan. 10, 2019, which claims the benefit of the filing date of U.S. Provisional Application No. 62/615,678, filed Jan. 10, 2018 and International Application No. PCT/CN2018/076982, filed on Feb. 22, 2018. The entire contents of these applications are incorporated herein by reference in their entirety.

TECHNICAL FIELD

The present disclosure relates to novel processes and intermediates for the preparation of compounds useful as stimulators of soluble guanylate cyclase (sGC). These processes produce stable 3-(2-pyrimidinyl)pyrazoles of Formula I in high purity and yields. These processes have the additional advantage of involving facile reaction conditions that are amenable to scale up for large scale manufacturing.

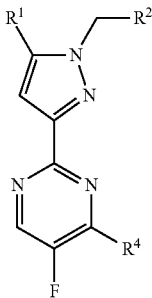

Formula I

BACKGROUND OF THE INVENTION sGC is the primary receptor for NO in vivo. sGC can be activated via both NO-dependent and NO-independent mechanisms. In response to this activation, sGC converts guanosine-5'-triphosphate (GTP) into the secondary messenger cGMP. The increased level of cGMP, in turn, modulates the activity of downstream effectors including protein kinases, phosphodiesterases (PDEs) and ion channels.

In the body, NO is synthesized from arginine and oxygen by various nitric oxide synthase (NOS) enzymes and by sequential reduction of inorganic nitrate. Experimental and clinical evidence indicates that reduced NO concentrations, reduced NO bioavailability and/or reduced responsiveness to endogenously produced NO contributes to the development of diseases.

sGC stimulators are NO-independent, heme-dependent modulators of the sGC enzyme, and display strong synergistic enzyme activation with NO. These are clearly differentiated from NO-independent, heme-independent sGC activators.

There is a need to develop novel sGC stimulators because compounds that stimulate sGC in an NO-independent manner offer considerable advantages over other current alternative therapies that target the aberrant NO pathway. As a result, there is also a need to develop efficient processes that are amenable to large scale manufacturing for the synthesis of these new sGC stimulators. There is a need for processes that are efficient and amenable to large scale manufacturing, which provide stable sGC stimulators in high purity and yields.

SUMMARY OF THE INVENTION

Novel processes for preparing compounds of Formula I are described herein.

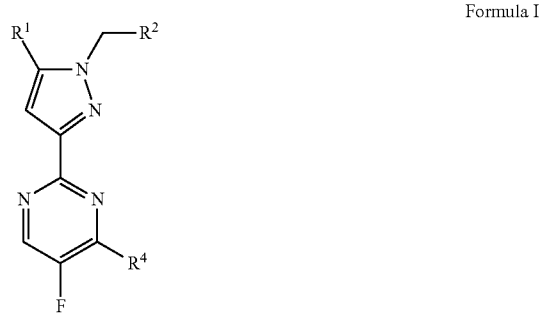

Formula I

In one aspect, compounds of Formula I and their pharmaceutically acceptable salts are sGC stimulators useful for treating diseases or disorders that benefit from sGC stimulation or from an increase in the concentration of nitric oxide (NO) and/or cyclic guanosine monophosphate (cGMP). In another aspect, compounds of Formula I are useful intermediates in the preparation of said sGC stimulators.

For a compound of Formula I, the following definitions apply:

$R^1$ is phenyl, or a 5 to 6-membered heteroaryl ring; optionally substituted with up to three instances independently selected from the group consisting of halogen or methyl; wherein said 5 or 6-membered heteroaryl ring contains up to 3 ring atoms selected from the group consisting of N, S or O;

$R^2$ is phenyl or a 6-membered heteroaryl, optionally substituted with up to three instances of $R^5$; wherein said 6-membered heteroaryl ring contains up to 2 nitrogen ring atoms;

$R^4$ is chloro, —OMe or —$NR^6R^7$;

each $R^5$ is independently methyl, methoxy or halogen;

$R^6$ is hydrogen or $C_{1-4}$ alkyl substituted with 0 to 3 instances of $R^8$;

$R^7$ is hydrogen or $C_{1-4}$ alkyl substituted with 0 to 3 instances of $R^8$; and each $R^8$ is independently —OH, $C_{1-3}$ haloalkyl, halogen or —C(O)$NH_2$.

In a first embodiment, a compound of Formula I is a compound of Formula II. In a second embodiment, a compound of Formula I is a compound of Formula III. In a third embodiment, a compound of Formula I is a compound of Formula IV. In a fourth embodiment, a compound of Formula I is a compound of Formula V. In a fifth embodiment, a compound of Formula I is a compound of Formula VI. In a sixth embodiment, a compound of Formula I is a compound of Formula VII. In a seventh embodiment, a compound of Formula I is Compound IA. In an eighth embodiment, a compound of Formula I is a compound of Formula IB. In a ninth embodiment, a compound of Formula I is a compound of Formula IC. In a tenth embodiment, a compound of Formula I is a compound of Formula ID. In an eleventh embodiment, a compound of Formula I is Compound (9). In a twelfth embodiment, a compound of Formula I is Compound (9').
Formula II
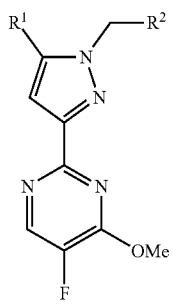
Compound 9
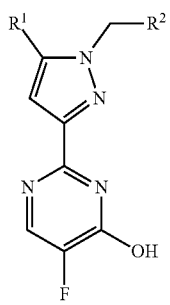
Formula III
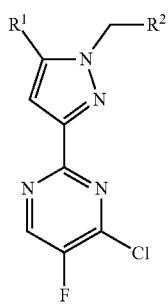
Formula IV
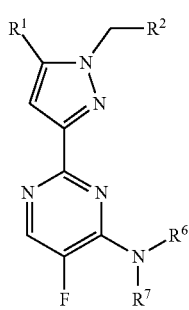
Formula V
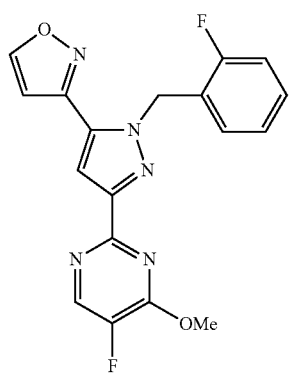
Compound 9'
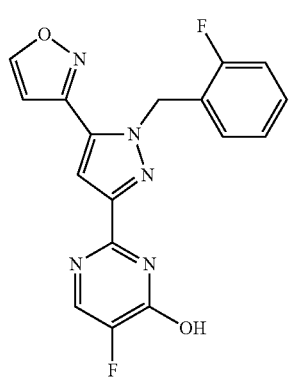
Formula VI
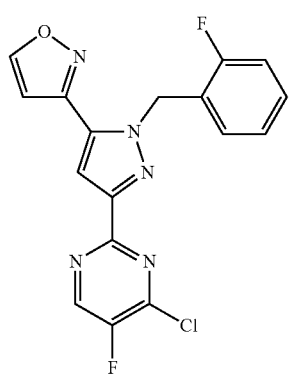
Formula VII
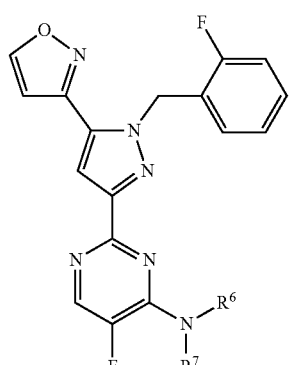

-continued

Formula IA

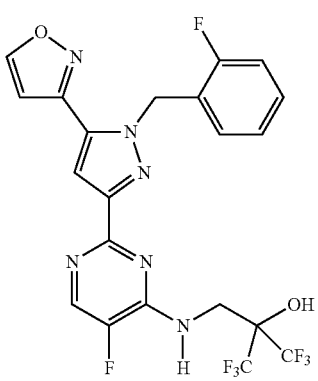

Formula IB

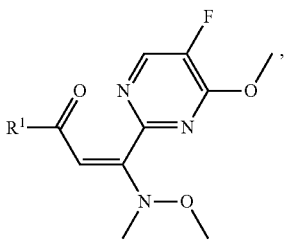

(4)

comprising the steps of:
i) coupling an amide of formula (1):

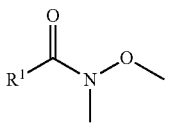

(1)

with a pyrimidine compound of formula (2):

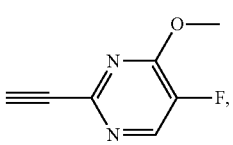

(2)

Formula IC

Formula ID

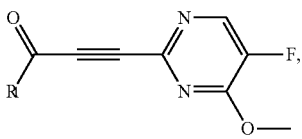

(3)

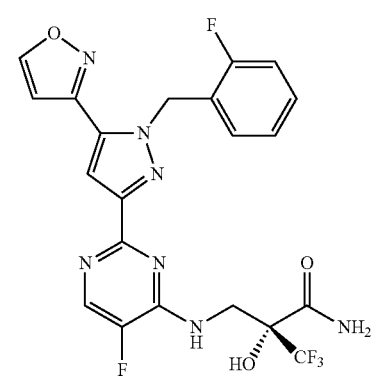

and ii) at a pH>5, optionally in the presence of added N,O-dimethylhydroxylamine or a salt (e.g., hydrochloride salt) thereof, allowing the mixture to react to form the compound of formula (4), wherein:

$R^1$ is phenyl, or a 5 to 6-membered heteroaryl ring; optionally substituted with up to three instances independently selected from the group consisting of halogen or methyl; wherein said 5 or 6-membered heteroaryl ring contains up to 3 ring atoms selected from the group consisting of N, S or O.

In a 1st specific embodiment, the present invention provides a process for preparing a compound of formula (4):

In a 2nd specific embodiment, the present invention provides a process for preparing a compound of Formula II:

[Formula II structure]

comprising the steps of:
i) coupling an amide of formula (1):

(1) [structure]

with a pyrimidine compound of formula (2):

(2) [structure]

in an aprotic organic solvent in the presence of a base, to form, after quenching with an acid, an intermediate of formula (3):

(3) [structure]

ii) at a pH>5, optionally in the presence of added N,O-dimethylhydroxylamine or a salt (e.g. HCl salt) thereof, allowing the mixture to react to form the compound of formula (4):

(4) [structure]

and
iii) condensing the compound of formula (4) with a hydrazine of formula $R^2$—$CH_2$—NH—$NH_2$ or a salt (e.g. HCl salt) thereof, optionally in the presence of a base, to form the compound of Formula II, wherein:

$R^1$ is phenyl, or a 5 to 6-membered heteroaryl ring; optionally substituted with up to three instances independently selected from the group consisting of halogen or methyl; wherein said 5 or 6-membered heteroaryl ring contains up to 3 ring atoms selected from the group consisting of N, S or O; and $R^2$ is phenyl or a 6-membered heteroaryl, optionally substituted with up to three instances of $R^5$; wherein said 6-membered heteroaryl ring contains up to 2 nitrogen ring atoms; and each $R^5$ is independently methyl, methoxy or halogen.

In a $3^{rd}$ specific embodiment, the present invention provides a process for preparing a compound of Formula II:

Formula II [structure]

comprising the steps of:
i) coupling an amide of formula (1):

(1) [structure]

with a pyrimidine compound of formula (2):

(2) [structure]

in an aprotic organic solvent in the presence of a base, to form, after quenching with an acid, an intermediate of formula (3):

(3) [structure]

ii) at a pH>5, optionally in the presence of added N,O-dimethylhydroxylamine or a salt (e.g. HCl salt) thereof, allowing the mixture to react to form the compound of formula (4):

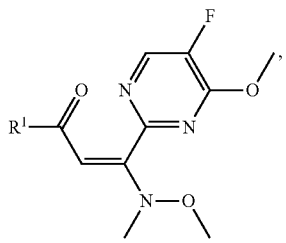

(4)

iiia) condensing the compound of formula (4) with hydrazine (e.g., hydrazine hydrate) to form the compound of formula (24):

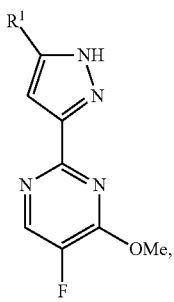

(24)

and iiib) alkylating intermediate of formula (24) with an alkylating agent of formula (22) to provide the compound of Formula II

 (22);

wherein:

$R^1$ is phenyl, or a 5 to 6-membered heteroaryl ring; optionally substituted with up to three instances independently selected from the group consisting of halogen or methyl; wherein said 5 or 6-membered heteroaryl ring contains up to 3 ring atoms selected from the group consisting of N, S or O; and $R^2$ is phenyl or a 6-membered heteroaryl, optionally substituted with up to three instances of $R^5$; wherein said 6-membered heteroaryl ring contains up to 2 nitrogen ring atoms;

each $R^5$ is independently methyl, methoxy or halogen; and

X is a leaving group selected from —Br, —I, —Cl, —F, and a sulfonate ester (e.g., mesylate, tosylate or triflate). In a more specific embodiment, X is —Br.

In a 4$^{th}$ specific embodiment, the present invention provides a process for preparing Compound (9):

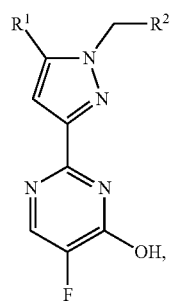

Compound (9)

comprising the steps of:

i) coupling an amide of formula (1):

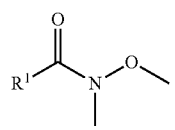

(1)

with a pyrimidine compound of formula (2):

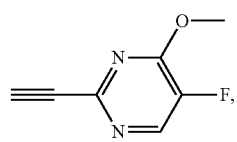

(2)

in an aprotic organic solvent in the presence of a base, to form, after quenching with an acid, an intermediate of formula (3):

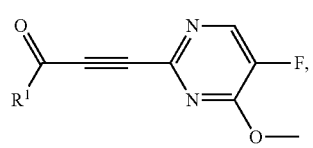

(3)

ii) at a pH>5, optionally in the presence of added N,O-dimethylhydroxylamine or a salt (e.g. HCl salt) thereof, allowing the mixture to react to form the compound of formula (4):

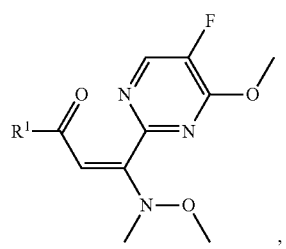

(4)

iii) condensing the compound of formula (4) with a hydrazine of formula $R^2$—$CH_2$—NH—$NH_2$ or a salt (e.g.

HCl salt) thereof, optionally in the presence of a base, to form the compound of Formula II;

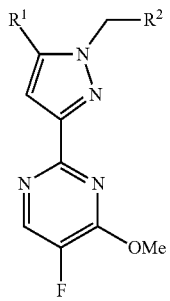

Formula II and iv) de-methylating the compound of Formula II to form an alcohol Compound (9); wherein $R^1$ is phenyl, or a 5 to 6-membered heteroaryl ring; optionally substituted with up to three instances independently selected from the group consisting of halogen or methyl; wherein said 5 or 6-membered heteroaryl ring contains up to 3 ring atoms selected from the group consisting of N, S or O; and $R^2$ is phenyl or a 6-membered heteroaryl, optionally substituted with up to three instances of $R^5$; wherein said 6-membered heteroaryl ring contains up to 2 nitrogen ring atoms; and each $R^5$ is independently methyl, methoxy or halogen.

In a 5$^{th}$ specific embodiment, the present invention provides a process for preparing Compound (9):

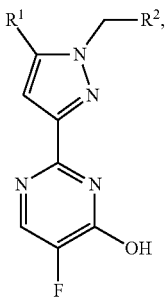

Compound (9)

comprising the steps of:

i) coupling an amide of formula (1):

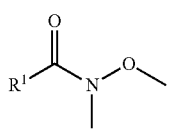

(1)

with a pyrimidine compound of formula (2):

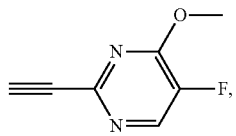

(2)

in an aprotic organic solvent in the presence of a base, to form, after quenching with an acid, an intermediate of formula (3):

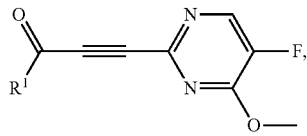

(3)

ii) at a pH>5, optionally in the presence of added N,O-dimethylhydroxylamine or a salt (e.g. HCl salt) thereof, allowing the mixture to react to form the compound of formula (4):

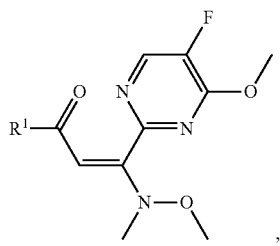

(4)

iiia) condensing the compound of formula (4) with hydrazine (e.g., hydrazine hydrate) to form the compound of formula (24):

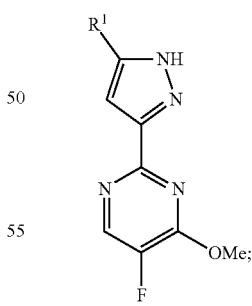

(24)

iiib) alkylating intermediate of formula (24) with an alkylating agent of formula (22) to provide the compound of Formula II:

(22)

$R^2$—CH$_2$—X

-continued

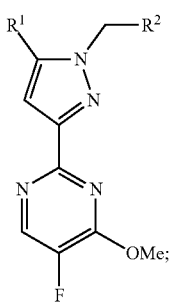
Formula II iv) de-methylating the compound of Formula II to form an alcohol Compound (9); wherein:

R¹ is phenyl, or a 5 to 6-membered heteroaryl ring; optionally substituted with up to three instances independently selected from the group consisting of halogen or methyl; wherein said 5 or 6-membered heteroaryl ring contains up to 3 ring atoms selected from the group consisting of N, S or O; and R² is phenyl or a 6-membered heteroaryl, optionally substituted with up to three instances of R⁵; wherein said 6-membered heteroaryl ring contains up to 2 nitrogen ring atoms;

each R⁵ is independently methyl, methoxy or halogen; and

X is a leaving group selected from —Br, —I, —Cl, —F, and a sulfonate ester (e.g., mesylate, tosylate or triflate). In a more specific embodiment, X is —Br.

In a 6$^{th}$ specific embodiment, the present invention provides a process for preparing a compound of formula III:

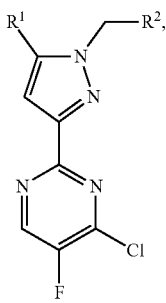
Formula III comprising the steps of:
i) coupling an amide of formula (1):

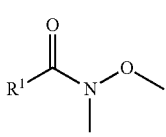
(1)

with a pyrimidine compound of formula (2):

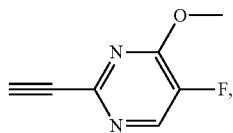
(2)

in an aprotic organic solvent in the presence of a base, to form, after quenching with an acid, an intermediate of formula (3):

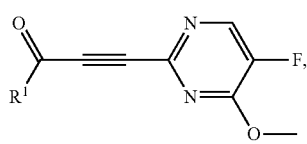
(3)

ii) at a pH>5, optionally in the presence of added N,O-dimethylhydroxylamine or a salt (e.g. HCl salt) thereof, allowing the mixture to react to form the compound of formula (4):

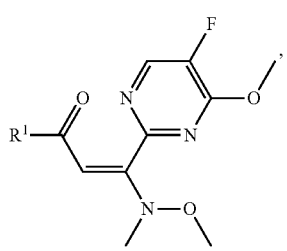
(4)

iii) condensing the compound of formula (4) with a hydrazine of formula R²—CH₂—NH—NH₂ or a salt (e.g., HCl salt) thereof, optionally in the presence of a base, to form a compound of Formula II:

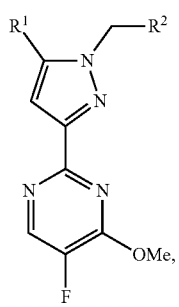
Formula II iv) de-methylating the compound of Formula II to form an alcohol compound of formula (9):

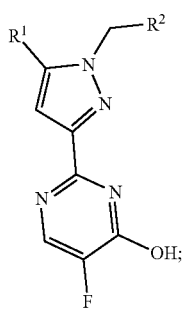

and v) chlorinating the alcohol compound of formula (9) with phosphoryl chloride to form the compound of Formula III, wherein $R^1$ and $R^2$ are as described above for Formula II.

In a 7$^{th}$ specific embodiment, the present invention provides a process for preparing a compound of formula III:

Formula III

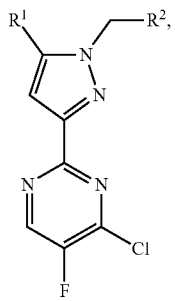

comprising the steps of:

i) coupling an amide of formula (1):

(1)

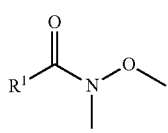

with a pyrimidine compound of formula (2):

(2)

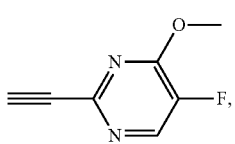

in an aprotic organic solvent in the presence of a base, to form, after quenching with an acid, an intermediate of formula (3):

(3)

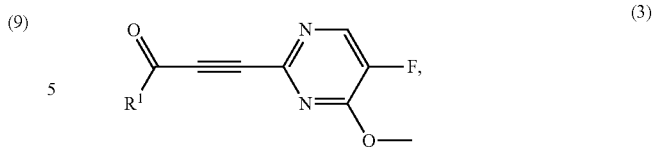

ii) at a pH>5, optionally in the presence of added N,O-dimethylhydroxylamine or a salt (e.g. HCl salt) thereof, allowing the mixture to react to form the compound of formula (4):

(4)

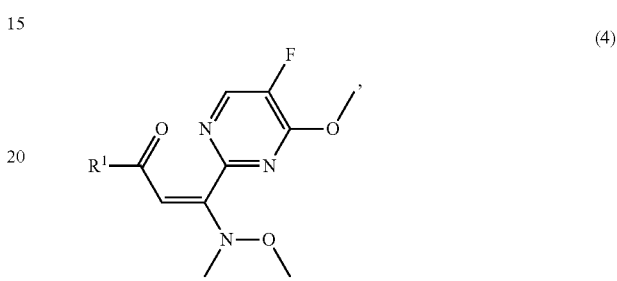

iiia) condensing the compound of formula (4) with hydrazine (e.g., hydrazine hydrate) to form the compound of formula (24):

(24)

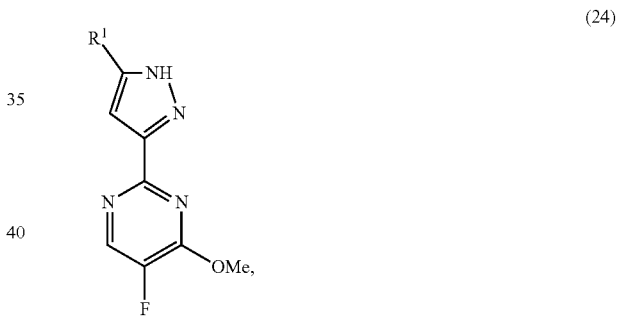

iiib) alkylating intermediate of formula (24) with an alkylating agent of formula (22) to provide the compound of Formula II:

(22)

Formula II

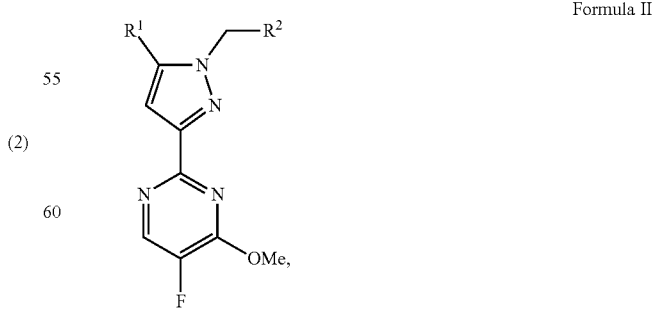

iv) de-methylating the compound of Formula II to form an alcohol compound of formula (9):

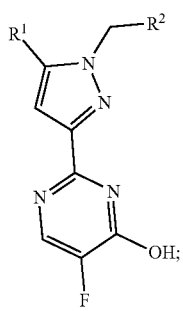

and v) chlorinating the alcohol compound of formula (9) with phosphoryl chloride to form the compound of Formula III, wherein $R^1$ and $R^2$ are as described above for Formula II; and X is a leaving group selected from —Br, —I, —Cl, —F, and a sulfonate ester (e.g., mesylate, tosylate or triflate).

In a 8$^{th}$ specific embodiment, the present invention provides a process of preparing a compound of Formula IV:

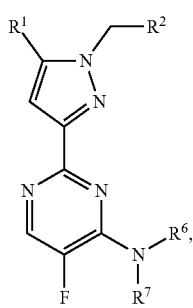

Formula IV comprising the steps of:

i) coupling an amide of formula (1):

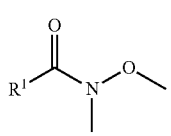

with a pyrimidine compound of formula (2):

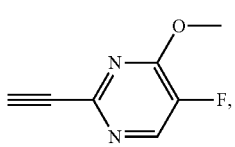

in an aprotic organic solvent in the presence of a base, to form, after quenching with acid, an intermediate of formula (3):

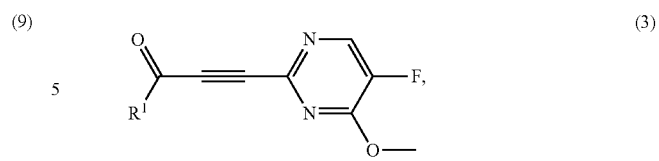

ii) at a pH>5, optionally in the presence of added N,O-dimethylhydroxylamine or a salt (e.g. HCl salt) thereof, allowing the mixture to react to form the compound of formula (4):

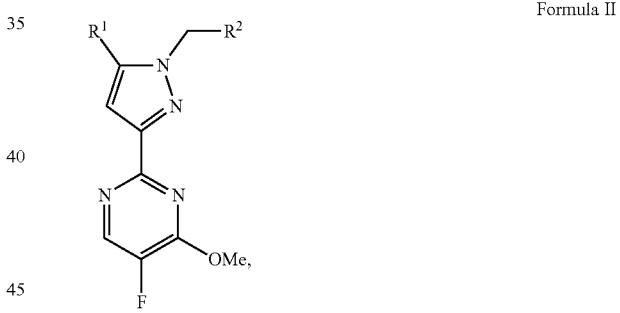

iii) condensing the compound of formula (4) with a hydrazine of formula $R^2$—$CH_2$—NH—$NH_2$ or a salt (e.g. HCl salt) thereof, optionally in the presence of a base, to form a compound of Formula II:

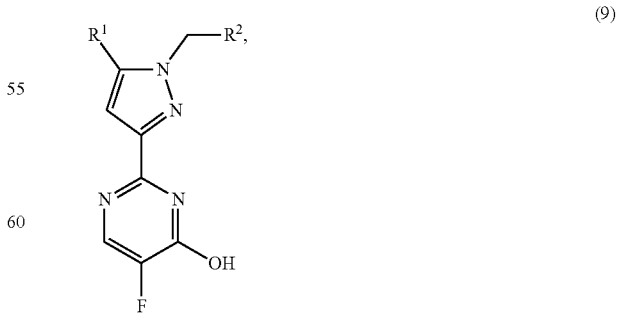

Formula II iv) de-methylating the compound of Formula II to form an alcohol compound of formula (9):

(9)

v) chlorinating the alcohol compound of formula (9) with phosphoryl chloride to form a compound of Formula III:

Formula III

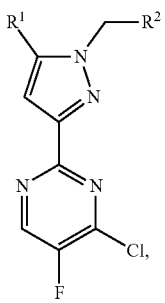

and vi) reacting an amine compound of formula (10):

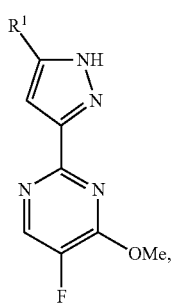
(10)

with the compound of Formula III, optionally in the presence of a base, to yield the compound of Formula IV, wherein:

$R^1$ is phenyl, or a 5 to 6-membered heteroaryl ring; optionally substituted with up to three instances independently selected from the group consisting of halogen or methyl; wherein said 5 or 6-membered heteroaryl ring contains up to 3 ring atoms selected from the group consisting of N, S or O;

$R^2$ is phenyl or a 6-membered heteroaryl, optionally substituted with up to three instances of $R^5$; wherein said 6-membered heteroaryl ring contains up to 2 nitrogen ring atoms, each $R^5$ is independently methyl, methoxy or halogen;

$R^6$ is hydrogen or $C_{1-4}$ alkyl substituted with 0 to 3 instances of $R^8$;

$R^7$ is hydrogen or $C_{1-4}$ alkyl substituted with 0 to 3 instances of $R^8$; and each $R^8$ is independently —OH, $C_{1-3}$ haloalkyl, halogen or —C(O)NH$_2$.

In a 9$^{th}$ specific embodiment, the present invention provides a process of preparing a compound of Formula IV:

Formula IV

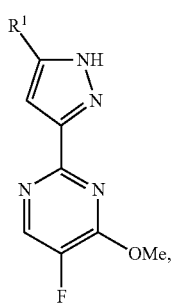

comprising the steps of:
i) coupling an amide of formula (1):

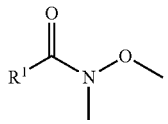
(1)

with a pyrimidine compound of formula (2):

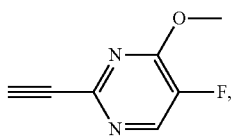
(2)

in an aprotic organic solvent in the presence of a base, to form, after quenching with acid, an intermediate of formula (3):

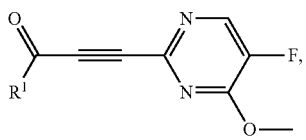
(3)

ii) at a pH>5, optionally in the presence of added N,O-dimethylhydroxylamine or a salt (e.g. HCl salt) thereof, allowing the mixture to react to form the compound of formula (4):

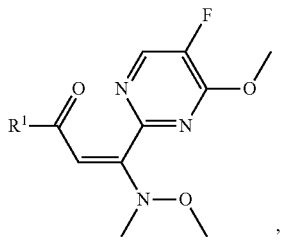
(4)

iiia) condensing the compound of formula (4) with hydrazine (e.g., hydrazine hydrate) to form the compound of formula (24):

(24)

iiib) alkylating intermediate of formula (24) with an alkylating agent of formula (22) to provide the compound of Formula II:

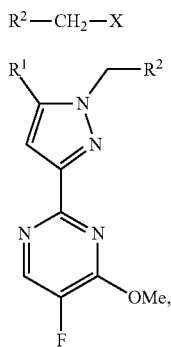

(22)

Formula II iv) de-methylating the compound of Formula II to form an alcohol compound of formula (9):

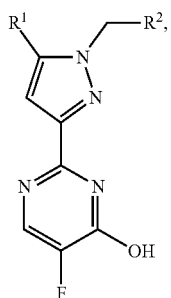

(9)

v) chlorinating the alcohol compound of formula (9) with phosphoryl chloride to form a compound of Formula III:

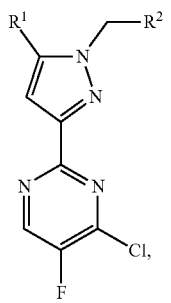

Formula III and
vi) reacting an amine compound of formula (10):

(10)

with the compound of Formula III, optionally in the presence of a base, to yield the compound of Formula IV, wherein:

$R^1$ is phenyl, or a 5 to 6-membered heteroaryl ring; optionally substituted with up to three instances independently selected from the group consisting of halogen or methyl; wherein said 5 or 6-membered heteroaryl ring contains up to 3 ring atoms selected from the group consisting of N, S or O;

$R^2$ is phenyl or a 6-membered heteroaryl, optionally substituted with up to three instances of $R^5$; wherein said 6-membered heteroaryl ring contains up to 2 nitrogen ring atoms, each $R^5$ is independently methyl, methoxy or halogen;

X is a leaving group selected from —Br, —I, —Cl, —F, and a sulfonate ester (e.g., mesylate, tosylate or triflate). In a more specific embodiment, X is —Br.

$R^6$ is hydrogen or $C_{1-4}$ alkyl substituted with 0 to 3 instances of $R^8$;

$R^7$ is hydrogen or $C_{1-4}$ alkyl substituted with 0 to 3 instances of $R^8$; and each $R^8$ is independently —OH, $C_{1-3}$ haloalkyl, halogen or —C(O)$NH_2$.

In a 10$^{th}$ specific embodiment, for the process described in the 1$^{st}$, 2$^{nd}$, 3$^{rd}$, 4$^{th}$, 5$^{th}$, 6$^{th}$, 7$^{th}$, 8$^{th}$ and 9$^{th}$ specific embodiment, the compound of formula (2) is prepared by a process comprising the steps of:

a) reacting dibromopyrimidine compound of formula (5):

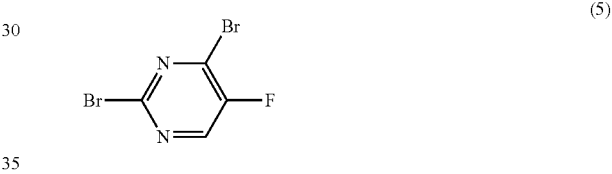

(5)

with a base in methanol or a methoxide salt in an aprotic solvent to form a bromopyrimidine compound of formula (6):

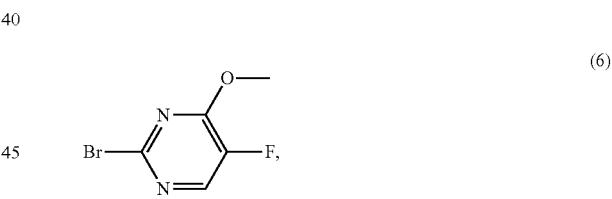

(6)

b) coupling the bromopyrimidine compound of formula (6) with ethynyltrimethylsilane, in an aprotic organic solvent in the presence of a base and a Pd catalyst, optionally in the presence of a Cu(I) catalyst, to form a compound of formula (7):

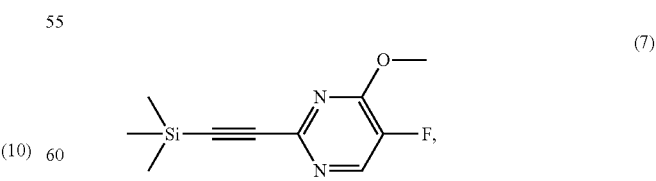

(7)

and
c) de-silylating the compound of formula (7) to form the pyrimidine compound of formula (2).

In a 11$^{th}$ specific embodiment, for the process described in the 1$^{st}$, 2$^{nd}$, 3$^{rd}$, 4$^{th}$, 5$^{th}$, 6$^{th}$, 7$^{th}$, 8$^{th}$, 9$^{th}$ and 10$^{th}$ specific embodiment, the compound of formula (1) is prepared by reacting a carboxylic acid of formula (8):

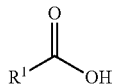
(8)

with oxalyl chloride or an equivalent amide coupling reagent, followed by N, O-dimethylhydroxylamine or a salt (e.g., hydrochloride salt) thereof in the presence of a base to form the amide of formula (1).

In a 12$^{th}$ embodiment, for steps i) and ii) of the process described in the 1$^{st}$, 2$^{nd}$, 3$^{rd}$, 4$^{th}$, 5$^{th}$, 6$^{th}$, 7$^{th}$, 8$^{th}$, 9$^{th}$, 10$^{th}$ and 11$^{th}$ specific embodiment, the process comprises contacting the reaction product of the amide of formula (1) and the pyrimidine compound of formula (2) with a solution comprising N,O-dimethylhydroxylamine or a salt thereof and an acid to form the compound of formula (4). In one embodiment, the acid is an aqueous acid. More specifically, the acid is hydrochloric acid. In another embodiment, the acid is a non-aqueous acid. More specifically, the acid is glacial acetic acid.

In certain embodiments, for the process described in the 1$^{st}$, 2$^{nd}$, 3$^{rd}$, 4$^{th}$, 5$^{th}$, 6$^{th}$, 7$^{th}$, 8$^{th}$, 9$^{th}$, 10$^{th}$, 11$^{th}$ and 12$^{th}$ specific embodiment, R$^1$ is a 5-membered heteroaryl ring. In other embodiments, R$^1$ is a 5-membered heteroaryl ring containing up to 2 ring heteroatoms selected from the group consisting of N and O.

In certain embodiments, for the process described in the 2$^{nd}$, 3$^{rd}$, 4$^{th}$, 5$^{th}$, 6$^{th}$, 7$^{th}$, 8$^{th}$, 9$^{th}$, 10$^{th}$, 11$^{th}$ and 12$^{th}$ specific embodiment, R$^2$ is phenyl optionally substituted with up to two instances of R$^5$. In some embodiments, R$^2$ is phenyl optionally substituted with one instance of R$^5$. In some embodiments, R$^2$ is represented by the formula

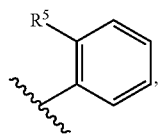

In some embodiments, R$^2$ is a 6-membered heteroaryl, optionally substituted with up to two instances of R$^5$; and wherein said 6-membered heteroaryl ring contains up to 2 nitrogen ring atoms.

In certain embodiments, for the process described in the 2$^{nd}$, 3$^{rd}$, 4$^{th}$, 5$^{th}$, 6$^{th}$, 7$^{th}$, 8$^{th}$, 9$^{th}$, 10$^{th}$, 11$^{th}$ and 12$^{th}$ specific embodiment, each R$^5$ is independently methyl or halogen. In some embodiments, each R$^5$ is independently halogen. In other embodiments, each R$^5$ is fluoro.

In certain embodiments, for the process described in the 8$^{th}$, 9$^{th}$, 10$^{th}$, 11$^{th}$ and 12$^{th}$ specific embodiment, R$^6$ is hydrogen or C$_{1-2}$ alkyl substituted with 0 to 3 instances of R$^8$. In some embodiment, R$^6$ is hydrogen.

In certain embodiments, for the process described in the 8$^{th}$, 9$^{th}$, 10$^{th}$, 11$^{th}$ and 12$^{th}$ specific embodiment, R$^7$ is hydrogen or C$_{1-2}$ alkyl substituted with 0 to 3 instances of R$^8$. In some embodiments, R$^7$ is C$_{1-2}$ alkyl substituted with 3 instances of R$^8$.

In certain embodiments, for the process described in the 8$^{th}$, 9$^{th}$, 10$^{th}$, 11$^{th}$ and 12$^{th}$ specific embodiment, each R$^8$ is independently —OH, trifluoromethyl, or —C(O)NH$_2$.

In certain embodiments, for the process described in the 1$^{st}$, 2$^{nd}$, 3$^{rd}$, 4$^{th}$, 5$^{th}$, 6$^{th}$, 7$^{th}$, 8$^{th}$, 9$^{th}$, 10$^{th}$, 11$^{th}$ and 12$^{th}$ specific embodiment, the definitions for the variables are described below:

R$^1$ is an unsubstituted 5-membered heteroaryl ring containing up to 2 ring heteroatoms selected from the group consisting of N and O;

R$^2$ is phenyl, optionally substituted with one or two instances of R$^5$;

each R$^5$ is fluoro;

R$^6$ is hydrogen;

R$^7$ is C$_{1-2}$ alkyl substituted with 3 instances of R$^8$; and each R$^8$ is independently —OH, trifluoromethyl, or —C(O)NH$_2$.

In certain embodiments, for the process described in the 1$^{st}$, 2$^{nd}$, 3$^{rd}$, 4$^{th}$, 5$^{th}$, 6$^{th}$, 7$^{th}$, 8$^{th}$, 9$^{th}$, 10$^{th}$, 11$^{th}$ and 12$^{th}$ specific embodiment, the definitions for the variables are described below:

R$^1$ is an unsubstituted 5-membered heteroaryl ring containing up to 2 ring heteroatoms selected from the group consisting of N and O;

R$^2$ is presented by the formula

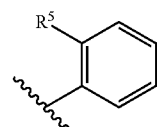

each R$^5$ is fluoro;

R$^6$ is hydrogen;

R$^7$ is C$_{1-2}$ alkyl substituted with 3 instances of R$^8$; and each R$^8$ is independently —OH, trifluoromethyl, or —C(O)NH$_2$.

In a 13$^{th}$ specific embodiment, the present invention provides a process of preparing a compound of formula (4'):

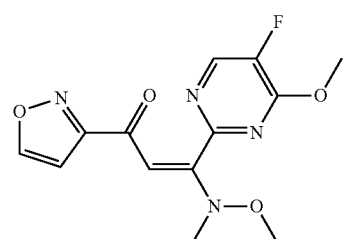
(4')

comprising the steps of:

i) coupling an amide of formula (1'):

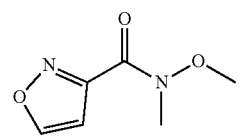
(1')

in an aprotic organic solvent in the presence of a base, to form, after quenching with acid, an intermediate of formula (3'):

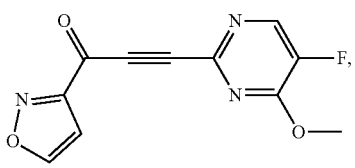

and ii) at a pH>5, optionally in the presence of added N,O-dimethylhydroxylamine or a salt (e.g. HCl salt) thereof, allowing the mixture to react to form the compound of formula (4').

In a 14th specific embodiment, the present invention provides a process of preparing a compound of Formula V:

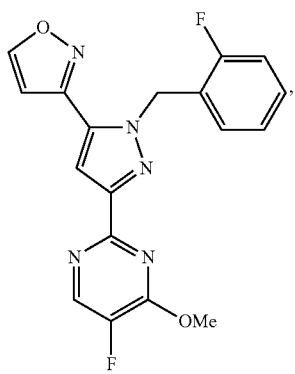

Formula V comprising the steps of:
i) coupling an amide of formula (1'):

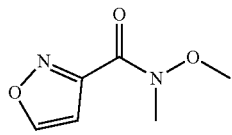

with a pyrimidine compound of formula (2):

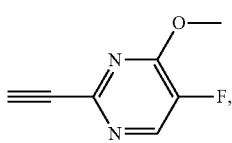

in an aprotic organic solvent in the presence of a base, to form, after quenching with acid, an intermediate of formula (3'):

ii) at a pH>5, optionally in the presence of added N,O-dimethylhydroxylamine or a salt (e.g. HCl salt) thereof, allowing the mixture to react to form the compound of formula (4'):

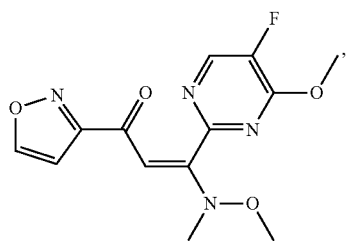

iii) condensing the compound of formula (4') with a hydrazine of formula

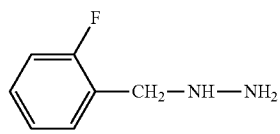

or a salt (e.g., HCl salt) thereof, optionally in the presence of a base, to form the compound of Formula V.

In a 15th specific embodiment, the present invention provides a process of preparing a compound of Formula V:

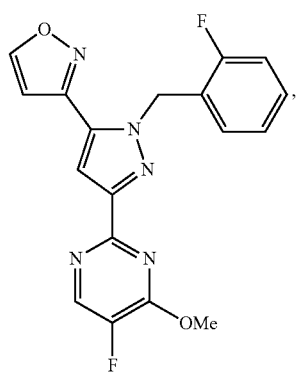

Formula V comprising the steps of:
i) coupling an amide of formula (1'):

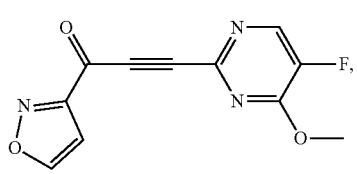

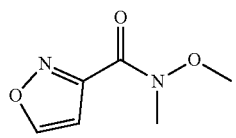

with a pyrimidine compound of formula (2):

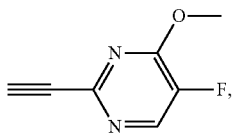
(2)

in an aprotic organic solvent in the presence of a base, to form, after quenching with acid, an intermediate of formula (3'):

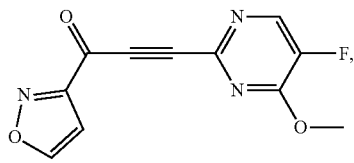
(3')

ii) at a pH>5, optionally in the presence of added N,O-dimethylhydroxylamine or a salt (e.g. HCl salt) thereof, allowing the mixture to react to form the compound of formula (4'):

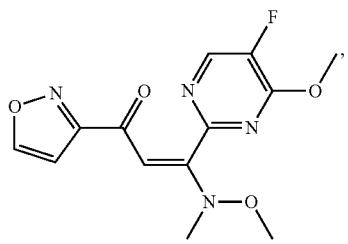
(4')

iiia) condensing the compound of formula (4') with hydrazine (e.g., hydrazine hydrate) to form the compound of formula (24'):

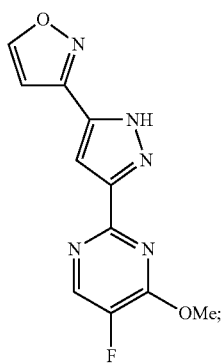
(24')

and iiib) alkylating intermediate of formula (24') with an alkylating agent of formula (23A) to provide the compound of Formula V:

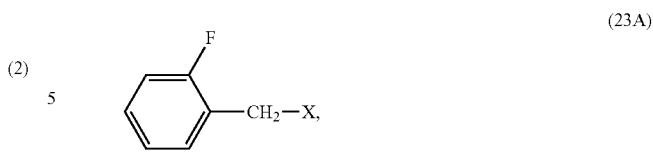
(23A)

wherein X is a leaving group selected from —Br, —I, —Cl, —F, and a sulfonate ester (e.g., mesylate, tosylate or triflate). In a more specific embodiment, X is —Br.

In a 16$^{th}$ specific embodiment, the present invention provides a process for preparing Compound (9'):

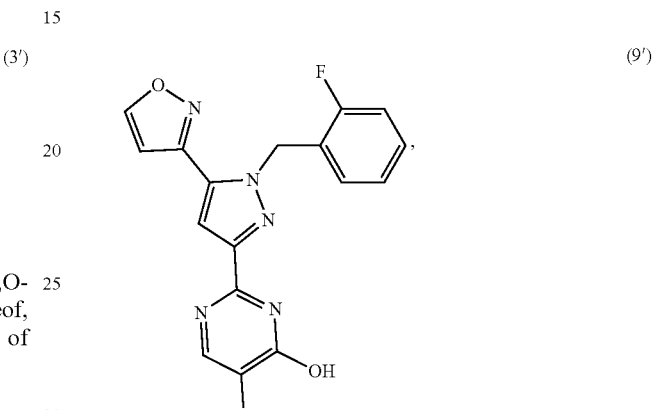
(9')

comprising the steps of:
i) coupling an amide of formula (1'):

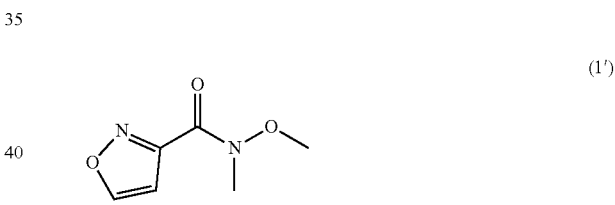
(1')

with a pyrimidine compound of formula (2):

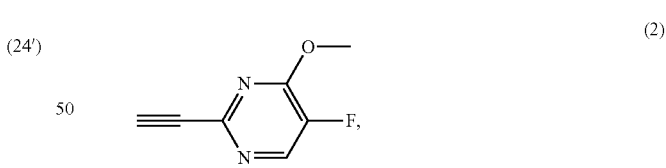
(2)

in an aprotic organic solvent in the presence of a base, to form, after quenching with acid, an intermediate of formula (3'):

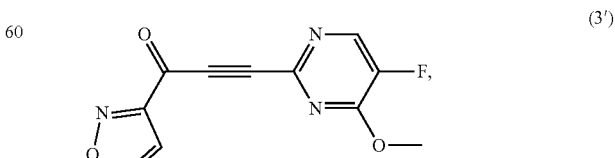
(3')

ii) at a pH>5, optionally in the presence of added N,O-dimethylhydroxylamine or a salt (e.g. HCl salt) thereof, allowing the mixture to react to form the compound of formula (4'):

(4')

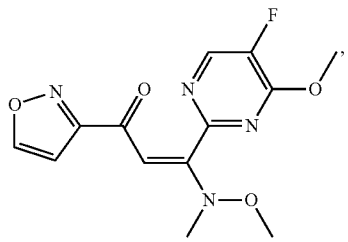

iii) condensing the compound of formula (4') with a hydrazine of formula

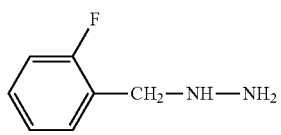

or a salt (e.g., HCl salt) thereof, optionally in the presence of a base, to form the compound of Formula V:

Formula V

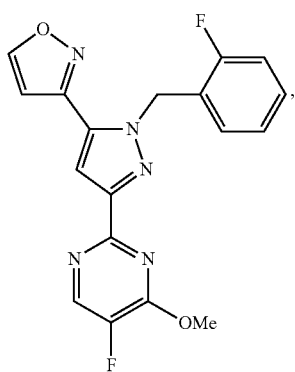

and iv) de-methylating the compound of Formula V to form an alcohol Compound (9').

In a 17$^{th}$ specific embodiment, the present invention provides a process for preparing Compound (9'):

(9')

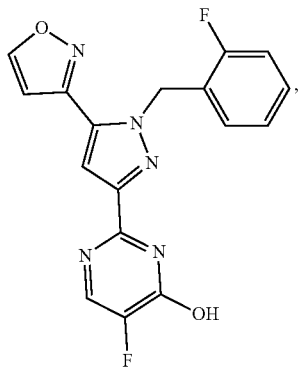

comprising the steps of:

i) coupling an amide of formula (1'):

(1')

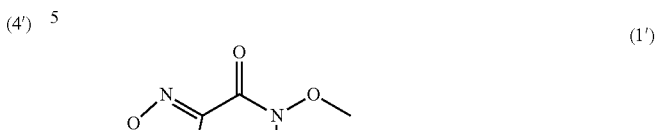

with a pyrimidine compound of formula (2):

(2)

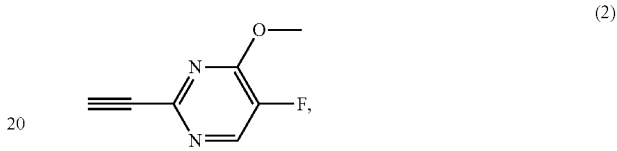

in an aprotic organic solvent in the presence of a base, to form, after quenching with acid, an intermediate of formula (3'):

(3')

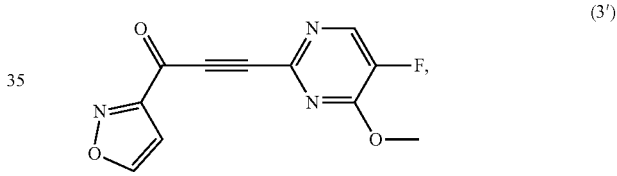

ii) at a pH>5, optionally in the presence of added N,O-dimethylhydroxylamine or a salt (e.g. HCl salt) thereof, allowing the mixture to react to form the compound of formula (4'):

(4')

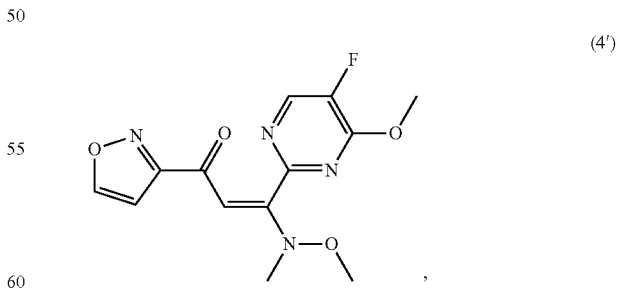

iiia) condensing the compound of formula (4') with hydrazine (e.g., hydrazine hydrate) to form the compound of formula (24'):

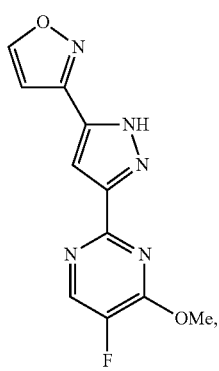
(24')

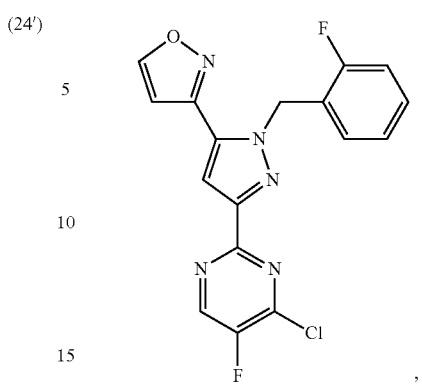
Formula VI iiib) alkylating intermediate of formula (24') with an alkylating agent of formula (23A) to provide the compound of Formula V:

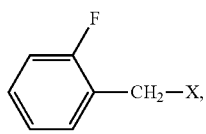
(23A)

comprising the steps of:
i) coupling an amide of formula (1'):

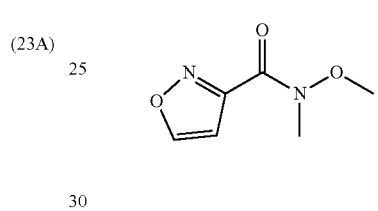
(1')

with a pyrimidine compound of formula (2):

Formula V

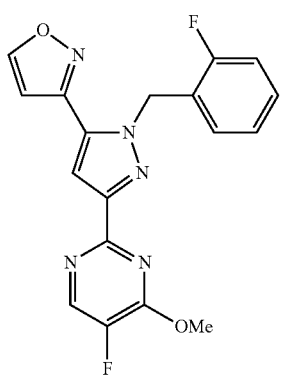

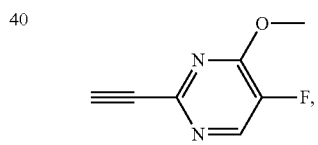
(2)

in an aprotic organic solvent in the presence of a base, to form, after quenching with acid, an intermediate of formula (3'):

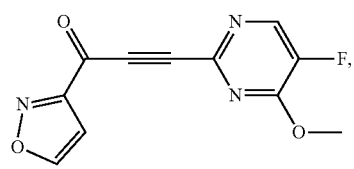
(3')

and iv) de-methylating the compound of Formula V to form an alcohol Compound (9'), wherein X is a leaving group selected from —Br, —I, —Cl, —F, and a sulfonate ester (e.g., mesylate, tosylate or triflate). In a more specific embodiment, X is —Br.

In an 18$^{th}$ specific embodiment, the present invention provides a process of preparing a compound of Formula VI:

ii) at a pH>5, optionally in the presence of added N,O-dimethylhydroxylamine or a salt (e.g. HCl salt) thereof, allowing the mixture to react to form the compound of formula (4'):

(4')

[Chemical structure: isoxazole-C(=O)-CH=C(N(OMe)Me)-pyrimidine(F)(OMe)]

iii) condensing the compound of formula (4') with a hydrazine of formula

[Chemical structure: 2-fluorobenzyl-CH₂—NH—NH₂]

or a salt (e.g., HCl salt) thereof, optionally in the presence of a base, to form a compound of Formula V:

Formula V

[Chemical structure: isoxazole-pyrazole with N-(2-fluorobenzyl) substituent, pyrazole linked to pyrimidine bearing F and OMe]

iv) de-methylating the compound of Formula V to form an alcohol compound of formula (9'):

(9')

[Chemical structure: same as Formula V but with OH instead of OMe on pyrimidine]

and
v) chlorinating the alcohol compound of formula (9') with phosphoryl chloride to form the compound of Formula VI.

In a 19th specific embodiment, the present invention provides a process of preparing a compound of Formula VI:

Formula VI

[Chemical structure: isoxazole-pyrazole with N-(2-fluorobenzyl) substituent, pyrazole linked to pyrimidine bearing F and Cl]

comprising the steps of:
i) coupling an amide of formula (1'):

(1')

[Chemical structure: isoxazole-3-carboxylic acid N-methoxy-N-methyl amide (Weinreb amide)]

with a pyrimidine compound of formula (2):

(2)

[Chemical structure: 2-ethynyl-5-fluoro-4-methoxypyrimidine]

in an aprotic organic solvent in the presence of a base, to form, after quenching with acid, an intermediate of formula (3'):

(3')

[Chemical structure: isoxazole-C(=O)-C≡C-pyrimidine(F)(OMe)]

ii) at a pH>5, optionally in the presence of added N,O-dimethylhydroxylamine or a salt (e.g. HCl salt) thereof, allowing the mixture to react to form the compound of formula (4'):

and v) chlorinating the alcohol compound of formula (9') with phosphoryl chloride to form the compound of Formula VI, wherein X is a leaving group selected from —Br, —I, —Cl, —F, and a sulfonate ester (e.g., mesylate, tosylate or triflate). In a more specific embodiment, X is —Br.

In a 20th specific embodiment, the present invention provides a process of preparing a compound of formula VII:

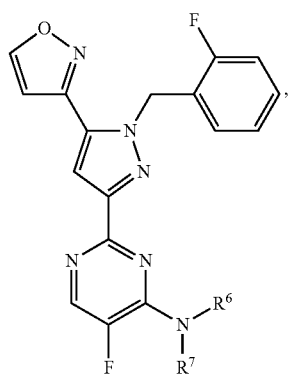

Formula VII comprising the steps of:

i) coupling an amide of formula (1'):

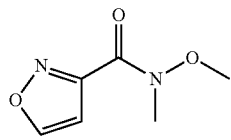

(1')

with a pyrimidine compound of formula (2):

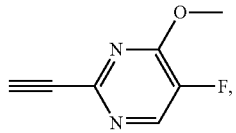

(2)

in an aprotic organic solvent in the presence of a base, to form, after quenching with an acid, an intermediate of formula (3'):

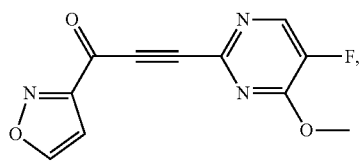

(3')

ii) at a pH>5, optionally in the presence of added N,O-dimethylhydroxylamine or a salt (e.g. HCl salt) thereof, allowing the mixture to react to form the compound of formula (4'):

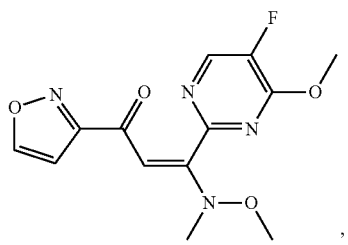

(4')

iiia) condensing the compound of formula (4') with hydrazine (e.g., hydrazine hydrate) to form the compound of formula (24'):

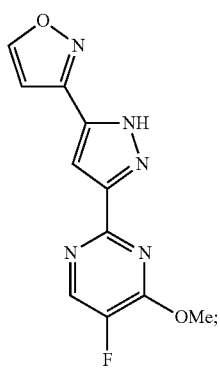

(24')

iiib) alkylating intermediate of formula (24') with an alkylating agent of formula (23A) to provide the compound of Formula V.

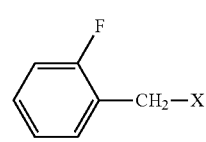

(23A)

iv) de-methylating the compound of Formula V to form an alcohol compound of formula (9'):

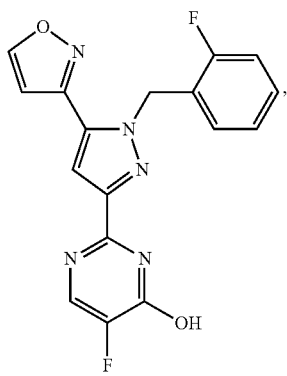

(9')

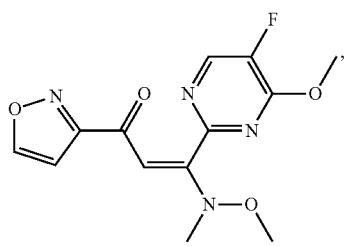

(4')

iii) condensing the compound of formula (4') with a hydrazine of formula

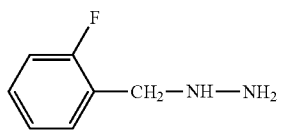

or a salt (e.g., HCl salt) thereof, optionally in the presence of a base, to form a compound of Formula V:

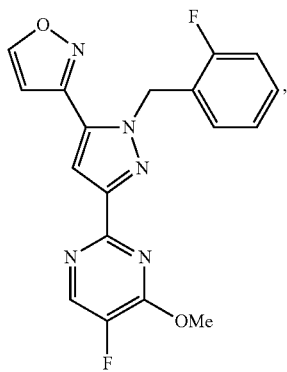

Formula V iv) de-methylating the compound of Formula V to form an alcohol compound of formula (9'):

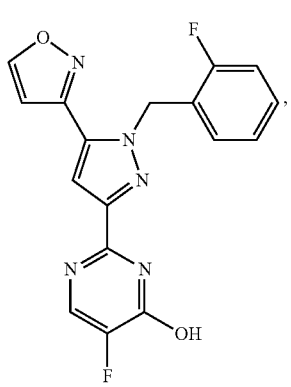

(9')

v) chlorinating the alcohol compound of formula (9') with phosphoryl chloride to form a compound of Formula VI:

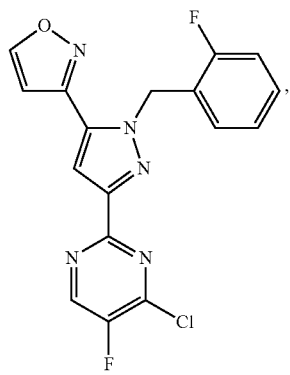

Formula VI and vi) reacting an amine compound of formula (10):

(10)

with the compound of Formula VI, optionally in the presence of a base, to yield the compound of Formula VII, wherein:

$R^6$ is hydrogen or $C_{1-4}$ alkyl substituted with 0 to 3 instances of $R^8$;

$R^7$ is hydrogen or $C_{1-4}$ alkyl substituted with 0 to 3 instances of $R^8$; and each $R^8$ is independently —OH, $C_{1-3}$ haloalkyl, halogen or —C(O)NH$_2$.

In a $21^{st}$ specific embodiment, the present invention provides a process of preparing a compound of formula VII:

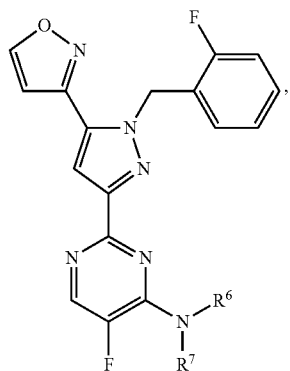

Formula VII comprising the steps of:

i) coupling an amide of formula (1'):

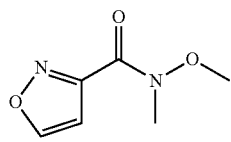

(1')

with a pyrimidine compound of formula (2):

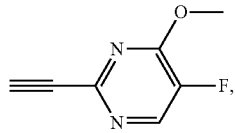
(2)

in an aprotic organic solvent in the presence of a base, to form, after quenching with an acid, an intermediate of formula (3'):

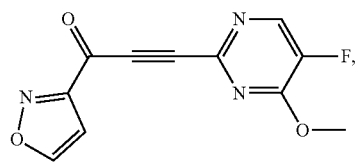
(3')

ii) at a pH>5, optionally in the presence of added N,O-dimethylhydroxylamine or a salt (e.g. HCl salt) thereof, allowing the mixture to react to form the compound of formula (4'):

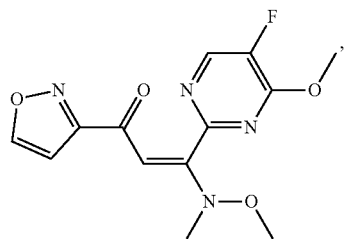
(4')

iiia) condensing the compound of formula (4') with hydrazine (e.g., hydrazine hydrate) to form the compound of formula (24'):

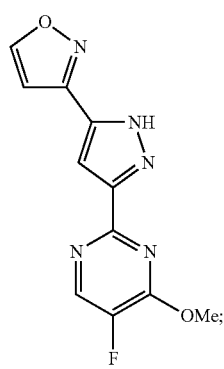
(24')

and iiib) alkylating intermediate of formula (24') with an alkylating agent of formula (23A) to provide the compound of Formula V:

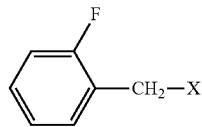
(23A)

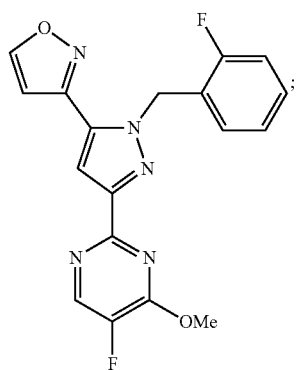
Formula V iv) de-methylating the compound of Formula V to form an alcohol compound of formula (9'):

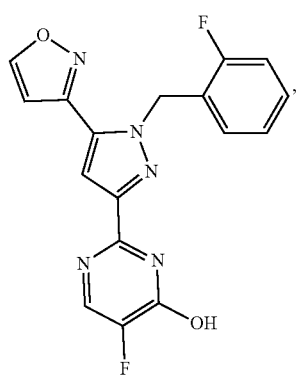
(9')

v) chlorinating the alcohol compound of formula (9') with phosphoryl chloride to form a compound of Formula VI:

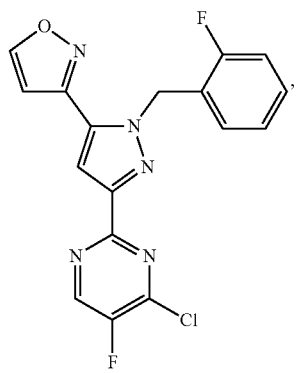
Formula VI and vi) reacting an amine compound of formula (10):

(10)

with the compound of Formula VI, optionally in the presence of a base, to yield the compound of Formula VII, wherein:

X is a leaving group selected from —Br, —I, —Cl, —F, and a sulfonate ester (e.g., mesylate, tosylate or triflate);

$R^6$ is hydrogen or $C_{1-4}$ alkyl substituted with 0 to 3 instances of $R^8$;

$R^7$ is hydrogen or $C_{1-4}$ alkyl substituted with 0 to 3 instances of $R^8$; and each $R^8$ is independently —OH, $C_{1-3}$ haloalkyl, halogen or —C(O)NH$_2$. In a more specific embodiment, X is —Br.

In a 22$^{nd}$ specific embodiment, for the process of the 13$^{th}$, 14$^{th}$, 15$^{th}$, 16$^{th}$, 17$^{th}$, 18$^{th}$, 19$^{th}$, 20$^{th}$, and 21$^{st}$ specific embodiments, the compound of formula (2) is prepared by a process comprising the steps of:

(a) reacting dibromopyrimidine compound of formula (5):

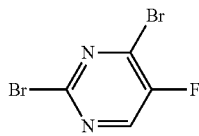
(5)

with a base in methanol or a methoxide salt in an aprotic solvent to form a bromopyrimidine compound of formula (6):

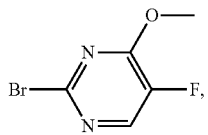
(6)

b) coupling the bromopyrimidine compound of formula (6) with ethynyltrimethylsilane, in an aprotic organic solvent in the presence of a base and a Pd catalyst, optionally in the presence of a Cu(I) catalyst, to form a compound of formula (7):

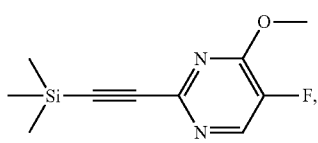
(7)

and c) de-silylating the compound of formula (7) to form the pyrimidine compound of (2).

In a 23$^{rd}$ specific embodiment, for the process of the 13$^{th}$, 14, 15$^{th}$, 16$^{th}$, 17$^{th}$, 18$^{th}$, 19$^{th}$, 20$^{th}$, 21$^{th}$, and 22$^{nd}$ specific embodiments, the compound of formula (1'$^{h}$) is prepared by reacting a carboxylic acid of formula (8'):

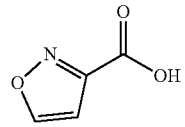
(8')

with oxalyl chloride or an equivalent amide coupling reagent, followed by N,O-dimethylhydroxylamine or a salt (e.g. HCl salt) thereof, in the presence of a base to form the amide of formula (1').

In certain embodiments, for the process of the 20$^{th}$, 21$^{st}$, 22$^{nd}$ or 23$^{rd}$ specific embodiment, $R^6$ is hydrogen or $C_{1-2}$ alkyl substituted with 0 to 3 instances of $R^8$. In some embodiments, $R^6$ is hydrogen.

In certain embodiments, for the process of the 20$^{th}$, 21$^{st}$, 22$^{nd}$ or 23$^{rd}$ specific embodiment, $R^7$ is hydrogen or $C_{1-2}$ alkyl substituted with 0 to 3 instances of $R^8$. In some embodiments, $R^7$ is $C_{1-2}$ alkyl substituted with 3 instances of $R^8$.

In certain embodiments, for the process of the 20$^{th}$, 21$^{st}$, 22$^{nd}$ or 23$^{rd}$ specific embodiment, $R^8$ is independently —OH, trifluoromethyl, or —C(O)NH$_2$.

In certain embodiments, for the process of the 20$^{th}$, 21$^{st}$, 22$^{nd}$ or 23$^{rd}$ specific embodiment, $R^6$ is hydrogen; $R^7$ is $C_{1-2}$ alkyl substituted with 3 instances of $R^8$ and each $R^8$ is independently —OH, trifluoromethyl, or —C(O)NH$_2$.

In a 24$^{th}$ specific embodiment, the present invention provides a process of preparing a compound of Formula IA:

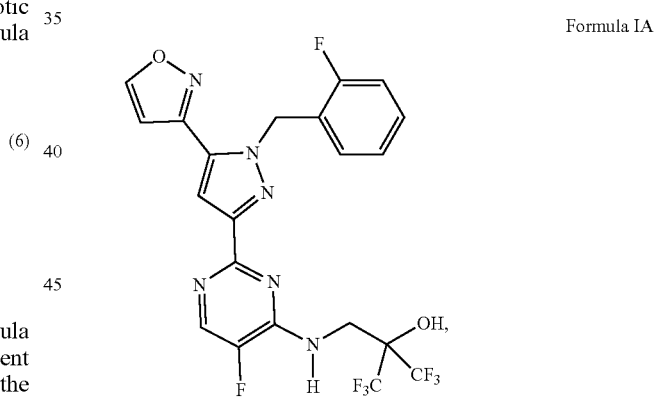
Formula IA comprising the step of:

i) coupling an amide of formula (1'):

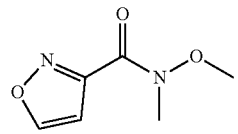
(1')

with a pyrimidine compound of formula (2):

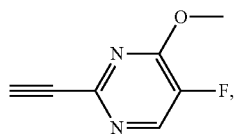
(2)

in an aprotic organic solvent in the presence of a base, to form, after quenching with an acid, an intermediate of formula (3'):

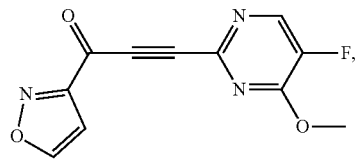
(3')

ii) at a pH>5, optionally in the presence of added N,O-dimethylhydroxylamine or a salt (e.g. HCl salt) thereof, allowing the mixture to react to form the compound of formula (4'):

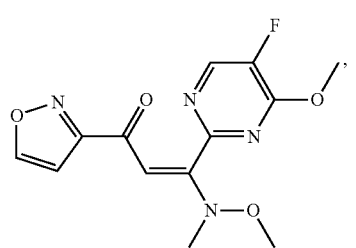
(4')

iii) condensing the compound of formula (4') with a hydrazine of formula

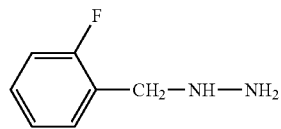

or a salt (e.g. HCl salt) thereof, optionally in the presence of a base, to form a compound of Formula V:

Formula V

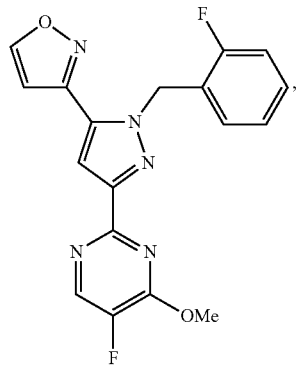

iv) de-methylating the compound of Formula V to form an alcohol compound of formula (9'):

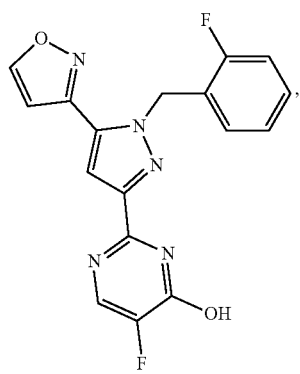
(9')

v) chlorinating the alcohol compound of formula (9') with phosphoryl chloride o form a compound of Formula VI:

Formula VI

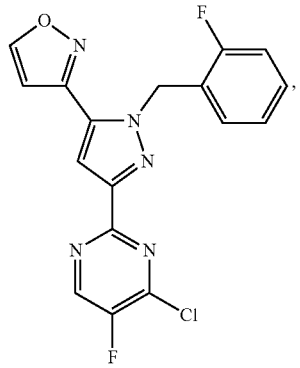

and vi) reacting an amine of formula (17):

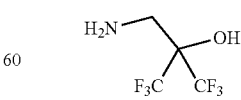
(17)

with the compound of Formula VI, optionally in the presence of a base, to yield the compound of Formula IA.

In a 25$^{th}$ specific embodiment, the present invention provides a process of preparing a compound of Formula IA:

Formula IA

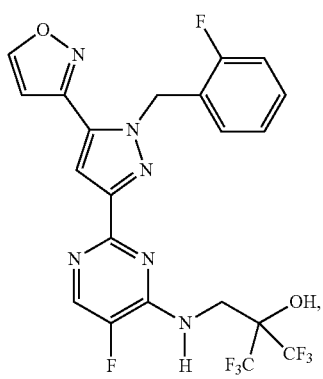

comprising the step of:
 i) coupling an amide of formula (1'):

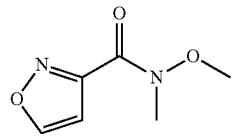

with a pyrimidine compound of formula (2):

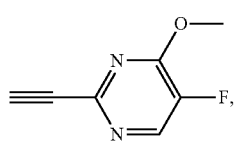

in an aprotic organic solvent in the presence of a base, to form, after quenching with an acid, an intermediate of formula (3'):

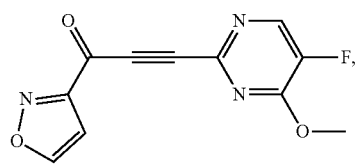

and
 ii) at a pH>5, optionally in the presence of added N,O-dimethylhydroxylamine or a salt (e.g. HCl salt) thereof, allowing the mixture to react to form the compound of formula (4'):

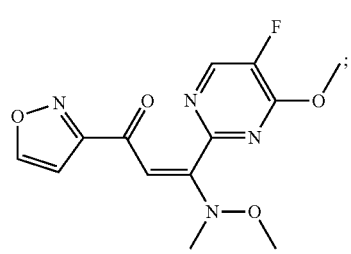

iiia) condensing the compound of formula (4') with hydrazine (e.g., hydrazine hydrate) to form the compound of formula (24'):

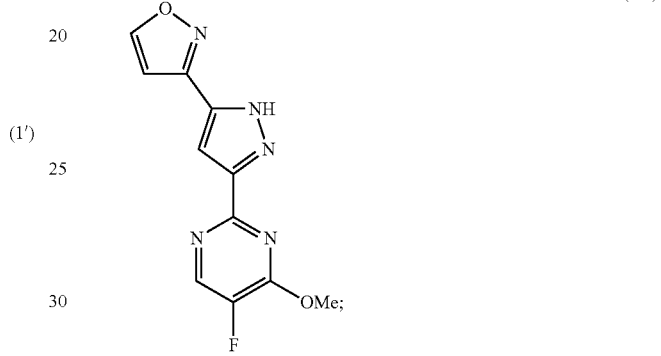

iiib) alkylating intermediate of formula (24') with an alkylating agent of formula (23A) to provide the compound of Formula V:

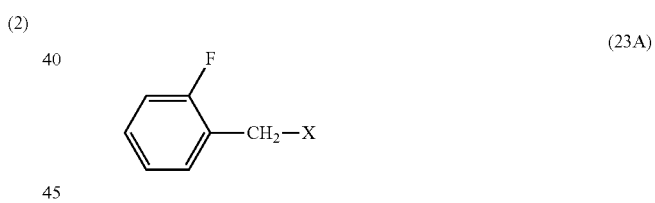

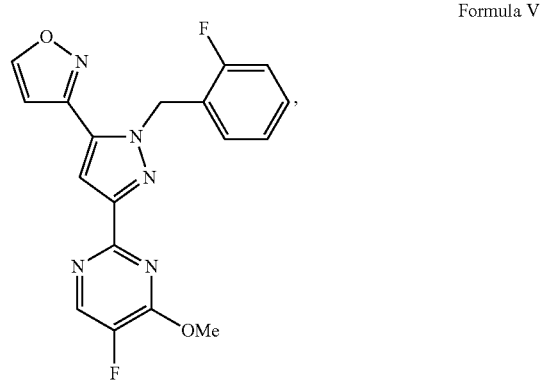 [SMILES: COc1nc(-c2cc(-c3ccon3)n(Cc3ccccc3F)n2)ncc1F]

iv) de-methylating the compound of Formula V to form an alcohol compound of formula (9'):

47

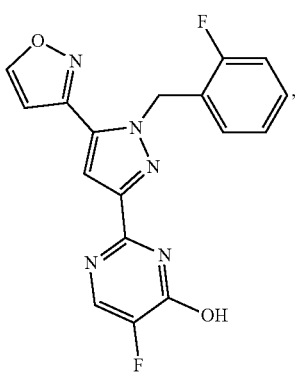

(9')

v) chlorinating the alcohol compound of formula (9') with phosphoryl chloride o form a compound of Formula VI:

Formula VI

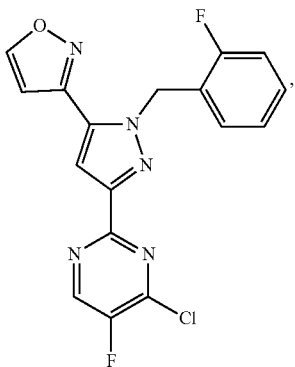

and
vi) reacting an amine of formula (17):

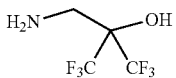

(17)

with the compound of Formula VI, optionally in the presence of a base, to yield the compound of Formula IA, wherein X is a leaving group selected from —Br, —I, —Cl, —F, and a sulfonate ester (e.g., mesylate, tosylate or triflate). In a more specific embodiment, X is —Br.

In one embodiment, the processes of the 24$^{th}$ and 25$^{th}$ specific embodiments further comprise recrystallization of the compound of Formula IA. In one embodiment, the process further comprises recrystallization of the compound of Formula IA in a mixture of methanol and water. In one embodiment, the recrystallization comprises the steps of: A') dissolving the compound of Formula IA in methanol at a temperature between 30° C. and 65° C. to obtain a methanol solution of the compound of Formula IA; B') filtering the methanol solution of the compound of Formula IA from step A') to form a filtered methanol solution of the compound of Formula IA; C') adding water to the filtered methanol solution of the compound of Formula IA at a temperature between 50° C. and 60° C. to yield a slurry; D') cooling the slurry of step C') to yield a recrystallized compound of Formula IA; and E') filtering and drying the recrystallized compound of Formula IA.

48

In a 26$^{th}$ specific embodiment, the present invention provides a process of preparing a compound of Formula IB:

Formula IB

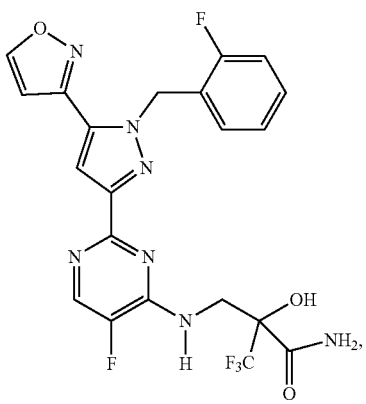

comprising the step of:
i) coupling an amide of formula (1'):

(1')

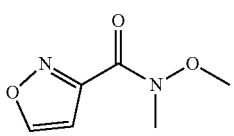

with a pyrimidine compound of formula (2):

(2)

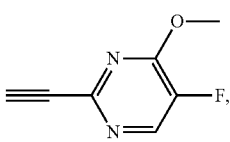

in an aprotic organic solvent in the presence of a base, to form, after quenching with an acid, an intermediate of formula (3'):

(3')

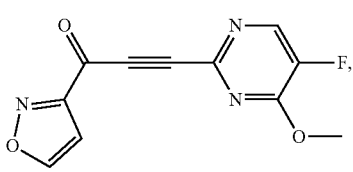

ii) at a pH>5, optionally in the presence of added N,O-dimethylhydroxylamine or a salt (e.g. HCl salt) thereof, allowing the mixture to react to form the compound of formula (4'):

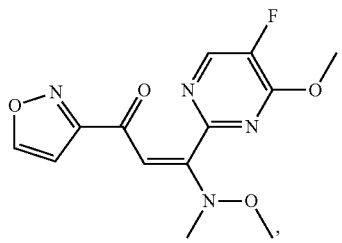

(4')

iii) condensing the compound of formula (4') with a hydrazine of formula

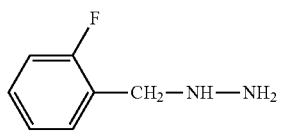

or a salt (e.g. HCl salt) thereof, optionally in the presence of a base, to form a compound of Formula V:

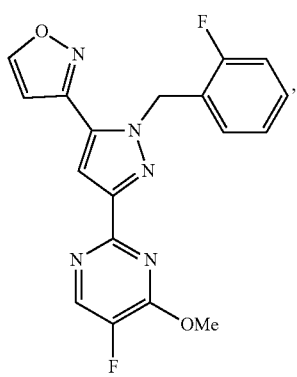

Formula V iv) de-methylating the compound of Formula V to form an alcohol compound of formula (9'):

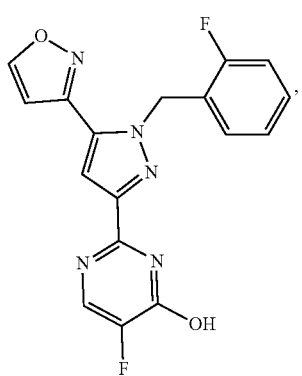

(9')

v) chlorinating the alcohol compound of formula (9') with phosphoryl chloride to form a compound of Formula VI:

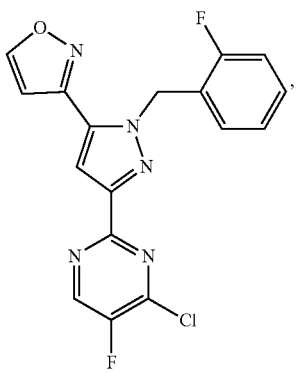

Formula VI and vi) reacting an amine of formula (13):

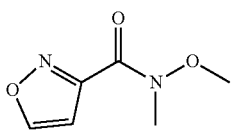

(13)

with the compound of Formula VI, optionally in the presence of a base, to yield the compound of Formula IB.

In a 27$^{th}$ specific embodiment, the present invention provides a process of preparing a compound of Formula IB:

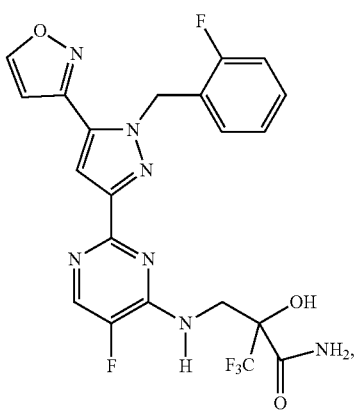

Formula IB comprising the step of:

i) coupling an amide of formula (1'):

(1')

with a pyrimidine compound of formula (2):

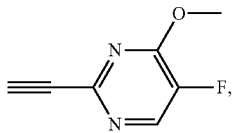
(2)

in an aprotic organic solvent in the presence of a base, to form, after quenching with an acid, an intermediate of formula (3'):

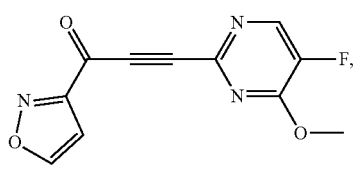
(3')

ii) at a pH>5, optionally in the presence of added N,O-dimethylhydroxylamine or a salt (e.g. HCl salt) thereof, allowing the mixture to react to form the compound of formula (4'):

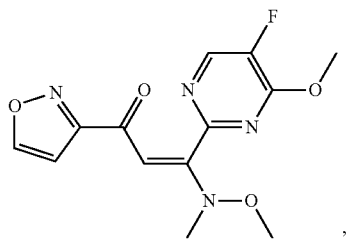
(4')

iiia) condensing the compound of formula (4') with hydrazine (e.g., hydrazine hydrate) to form the compound of formula (24'):

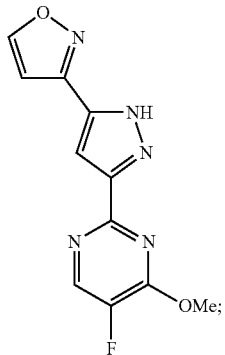
(24')

iiib) alkylating intermediate of formula (24') with an alkylating agent of formula (23A) to provide the compound of Formula V:

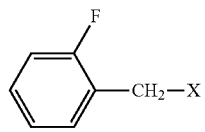
(23A)

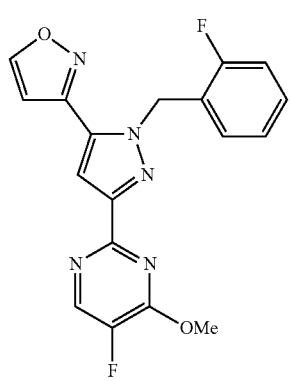
Formula V iv) de-methylating the compound of Formula V to form an alcohol compound of formula (9'):

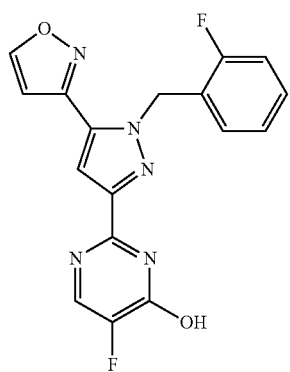
(9')

v) chlorinating the alcohol compound of formula (9') with phosphoryl chloride to form a compound of Formula VI:

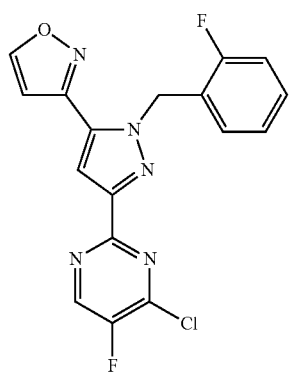
Formula VI and vi) reacting an amine of formula (13):

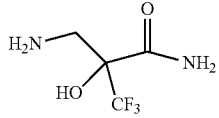
(13)

with the compound of Formula VI, optionally in the presence of a base, to yield the compound of Formula IB, wherein X is a leaving group selected from —Br, —I, —Cl, —F, and a sulfonate ester (e.g., mesylate, tosylate or triflate). In a more specific embodiment, X is —Br.

In a 28$^{th}$ specific embodiment, the present invention provides a process of preparing a compound of Formula IC:

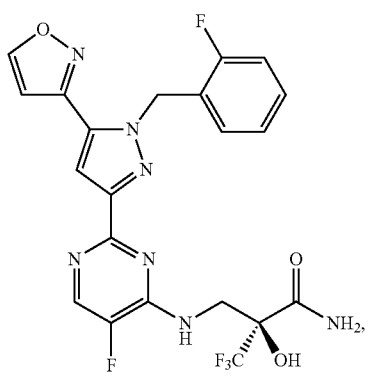
Formula IC comprising the steps of:

i) coupling an amide of formula (1'):

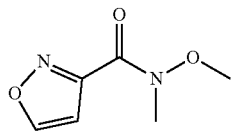
(1')

with a pyrimidine compound of formula (2):

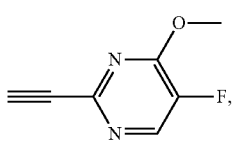
(2)

in an aprotic organic solvent in the presence of a base, to form, after quenching with an acid, an intermediate of formula (3'):

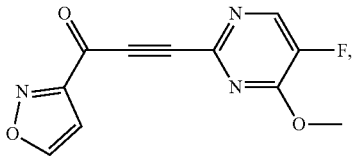
(3')

ii) at a pH>5, optionally in the presence of added N,O-dimethylhydroxylamine or a salt (e.g. HCl salt) thereof, allowing the mixture to react to form the compound of formula (4'):

(4')

iii) condensing the compound of formula (4') with a hydrazine of formula

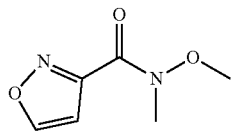

or a salt (e.g. HCl salt) thereof, optionally in the presence of a base, to form a compound of Formula V:

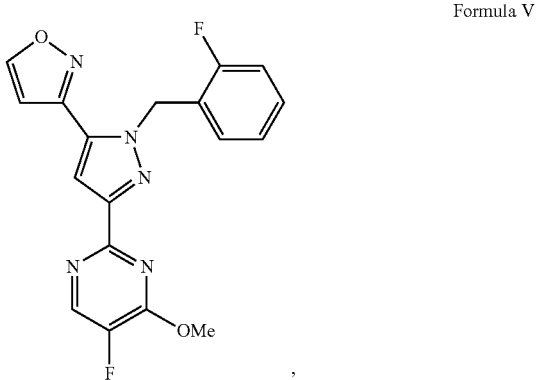 [SMILES: COc1nc(-c2cc(-c3ccon3)n(Cc3ccccc3F)n2)ncc1F]
Formula V iv) de-methylating the compound of Formula V to form an alcohol compound of formula (9'):

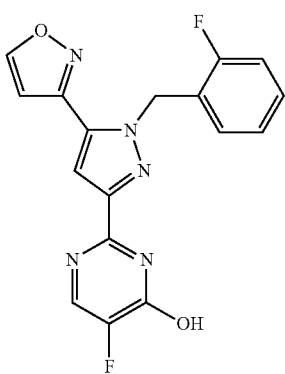

(9')

v) chlorinating the alcohol compound of formula (9') with phosphoryl chloride to form a compound of Formula VI:

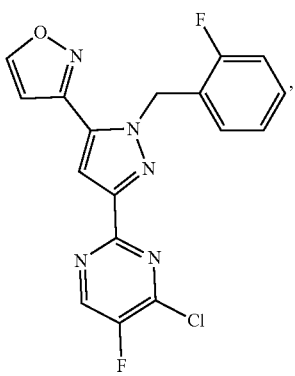

Formula VI and vi) reacting an amine of formula (19A) or its HCl salt of formula (19):

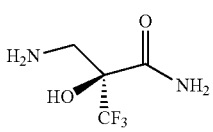

(19A)

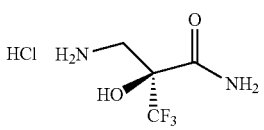

(19)

with the compound of Formula VI, optionally in the presence of a base, to yield the compound of Formula IC.

In a 29th specific embodiment, the present invention provides a process of preparing a compound of Formula IC:

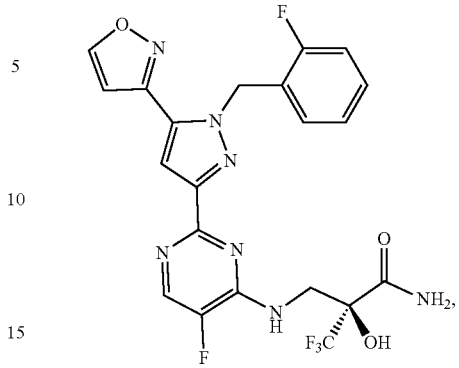

Formula IC comprising the steps of:

i) coupling an amide of formula (1'):

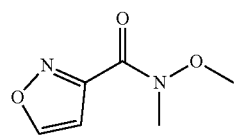

(1')

with a pyrimidine compound of formula (2):

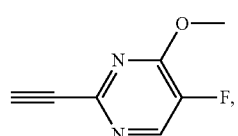

(2)

in an aprotic organic solvent in the presence of a base, to form, after quenching with an acid, an intermediate of formula (3'):

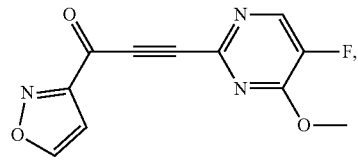

(3')

ii) at a pH>5, optionally in the presence of added N,O-dimethylhydroxylamine or a salt (e.g. HCl salt) thereof, allowing the mixture to react to form the compound of formula (4'):

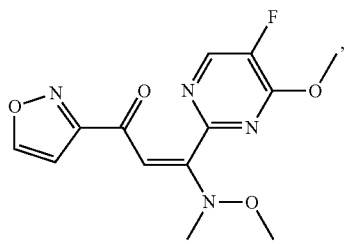

(4')

iiia) condensing the compound of formula (4') with hydrazine (e.g., hydrazine hydrate) to form the compound of formula (24'):

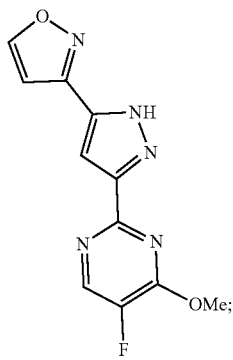

(24')

iiib) alkylating intermediate of formula (24') with an alkylating agent of formula (23A) to provide the compound of Formula V:

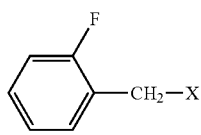

(23A)

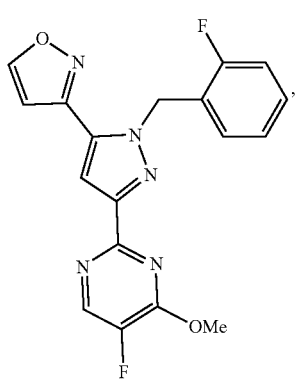

Formula V iv) de-methylating the compound of Formula V to form an alcohol compound of formula (9'):

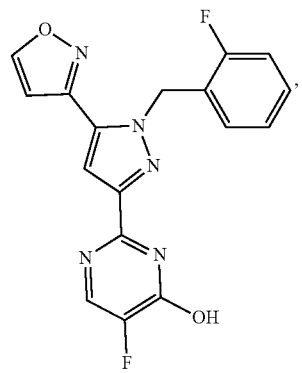

(9')

v) chlorinating the alcohol compound of formula (9') with phosphoryl chloride to form a compound of Formula VI:

Formula VI

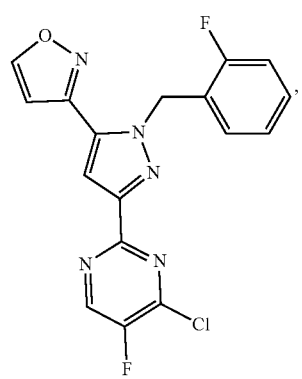

and vi) reacting an amine of formula (19A) or its HCl salt of formula (19):

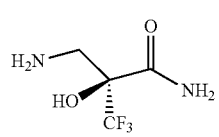

(19A)

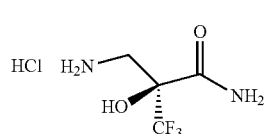

(19)

with the compound of Formula VI, optionally in the presence of a base, to yield the compound of Formula IC, wherein X is a leaving group selected from —Br, —I, —Cl, —F, and a sulfonate ester (e.g., mesylate, tosylate or triflate). In a more specific embodiment, X is —Br.

In a 30th specific embodiment, the present invention provides a process of preparing a compound of Formula ID:

Formula ID

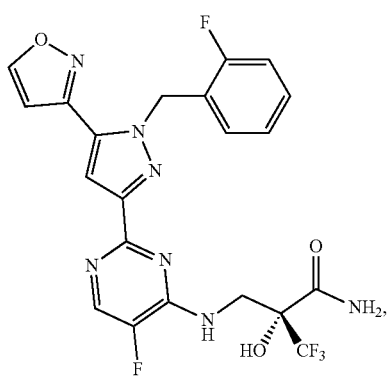

comprising the steps of:
i) coupling an amide of formula (1'):

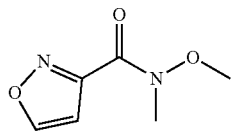
(1')

with a pyrimidine compound of formula (2):

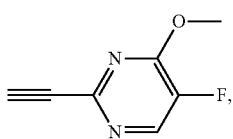
(2)

in an aprotic organic solvent in the presence of a base, to form, after quenching with an acid, an intermediate of formula (3'):

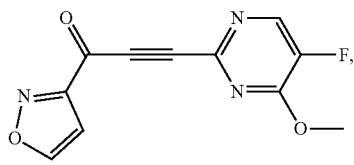
(3')

ii) at a pH>5, optionally in the presence of added N,O-dimethylhydroxylamine or a salt (e.g. HCl salt) thereof, allowing the mixture to react to form the compound of formula (4'):

(4')

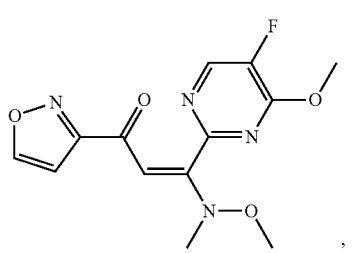

iii) condensing the compound of formula (4') with a hydrazine of formula

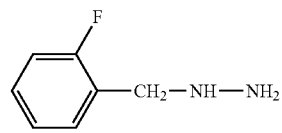

or a salt (e.g. HCl salt) thereof, optionally in the presence of a base, to form a compound of Formula V:

Formula V

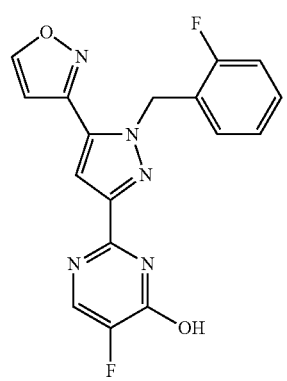

iv) de-methylating the compound of Formula V to form an alcohol compound of formula (9'):

(9')

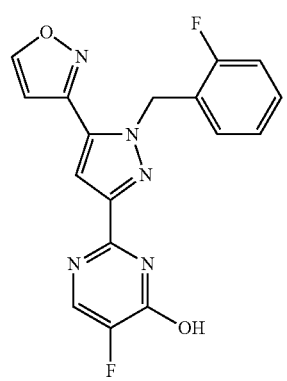

v) chlorinating the alcohol compound of formula (9') with phosphoryl chloride to form a compound of Formula VI:

Formula VI

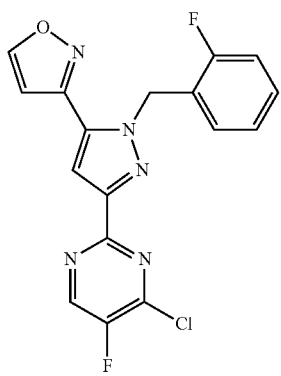

and
vi) reacting an amine of formula (15A) or its HCl salt of formula (15):

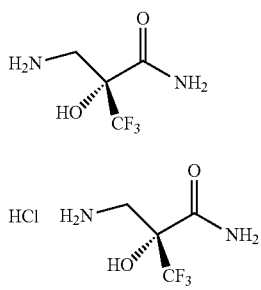

with the compound of Formula VI, optionally in the presence of a base, to yield the compound of Formula ID.

In a 31$^{st}$ specific embodiment, the present invention provides a process of preparing a compound of Formula ID:

Formula ID

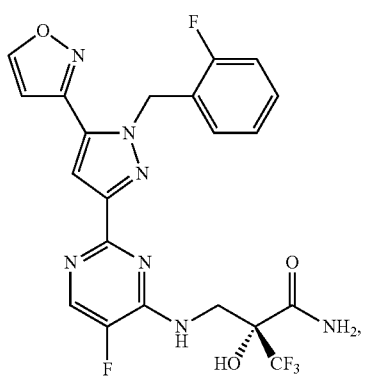

comprising the steps of:
i) coupling an amide of formula (1'):

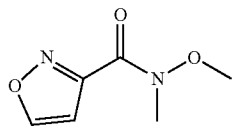

(1')

with a pyrimidine compound of formula (2):

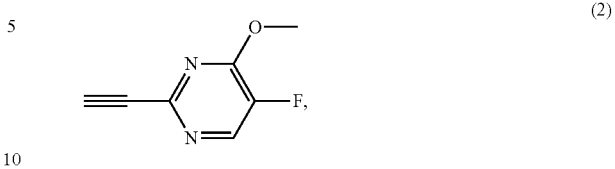

(2)

in an aprotic organic solvent in the presence of a base, to form, after quenching with an acid, an intermediate of formula (3'):

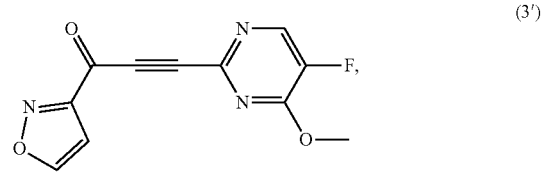 [SMILES: COc1nc(C#CC(=O)c2ccon2)ncc1F]

(3')

ii) at a pH>5, optionally in the presence of added N,O-dimethylhydroxylamine or a salt (e.g. HCl salt) thereof, allowing the mixture to react to form the compound of formula (4'):

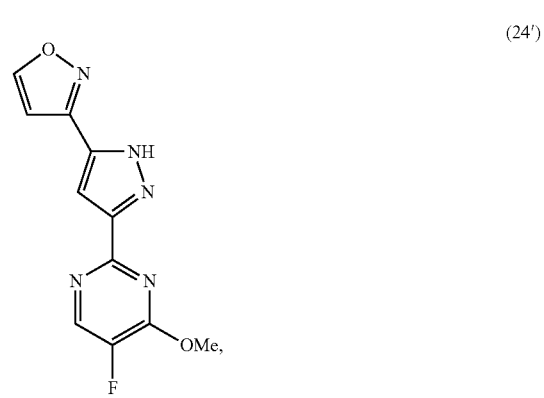 [SMILES: COc1nc(-c2cc(-c3ccon3)[nH]n2)ncc1F]

(4')

iiia) condensing the compound of formula (4') with hydrazine (e.g., hydrazine hydrate) to form the compound of formula (24'):

(24')

iiib) alkylating intermediate of formula (24') with an alkylating agent of formula (23A) to provide the compound of Formula V:

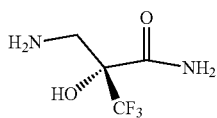

(23A)

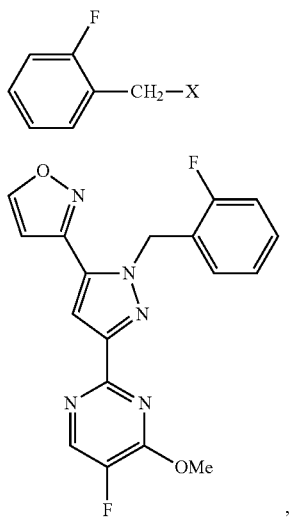

iv) de-methylating the compound of Formula V to form an alcohol compound of formula (9'):

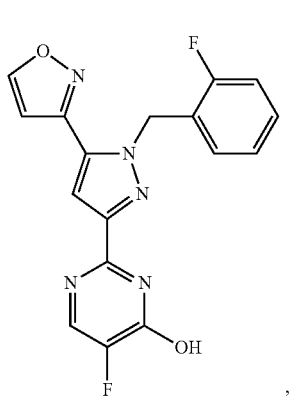

(9')

v) chlorinating the alcohol compound of formula (9') with phosphoryl chloride to form a compound of Formula VI:

Formula VI

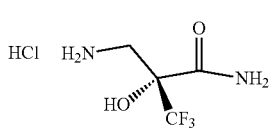

(15A)

Formula V

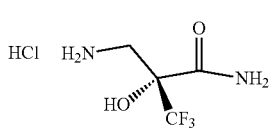

(15)

with the compound of Formula VI, optionally in the presence of a base, to yield the compound of Formula ID, wherein X is a leaving group selected from —Br, —I, —Cl, —F, and a sulfonate ester (e.g., mesylate, tosylate or triflate). In a more specific embodiment, X is —Br.

In a 32$^{nd}$ specific embodiment, the present invention provides a process of preparing a compound of Formula IC:

Formula IC

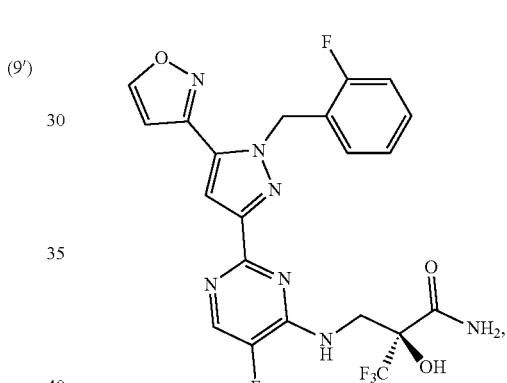

comprising the steps of:

i) coupling an amide of formula (1'):

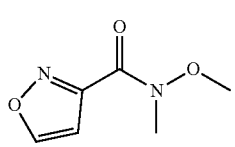

(1')

with a pyrimidine compound of formula (2):

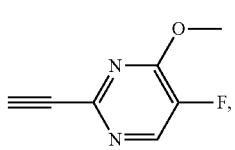

(2)

and vi) reacting an amine of formula (15A) or its HCl salt of formula (15):

in an aprotic organic solvent in the presence of a base, to form, after quenching with an acid, an intermediate of formula (3'):

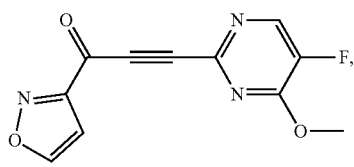
(3')

ii) at a pH>5, optionally in the presence of added N,O-dimethylhydroxylamine or a salt (e.g. HCl salt) thereof, allowing the mixture to react to form the compound of formula (4'):

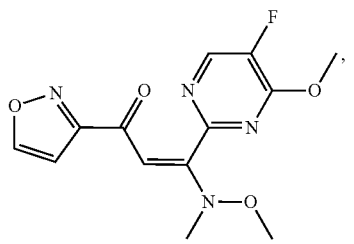
(4')

iii) condensing the compound of formula (4') with a hydrazine of formula

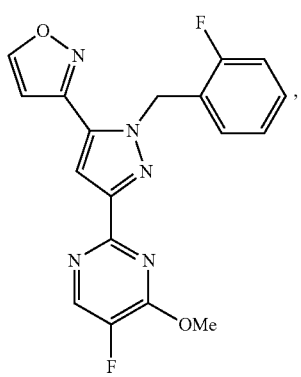

or a salt (e.g., HCl salt) thereof, optionally in the presence of a base, to form a compound of Formula V:

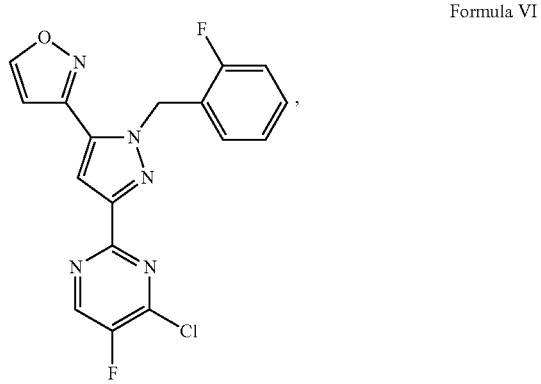 [SMILES: Fc1ccccc1Cn1nc(-c2ncc(F)c(Cl)n2)cc1-c1ccon1]
Formula V iv) de-methylating the compound of Formula V to form an alcohol compound of formula (9'):

(9')

v) chlorinating the alcohol compound of formula (9') with phosphoryl chloride to form a compound of Formula VI:

Formula VI and vi) reacting an (L)-malic acid salt of an amine (21) represented by formula (18):

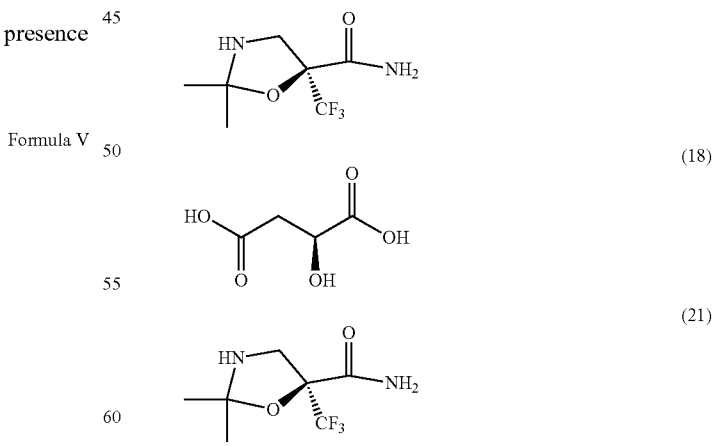
(18)

(21)

with the compound of Formula VI, optionally in the presence of a base, to yield the compound of Formula IC.

In a 33$^{rd}$ specific embodiment, the present invention provides a process of preparing a compound of Formula IC:

Formula IC

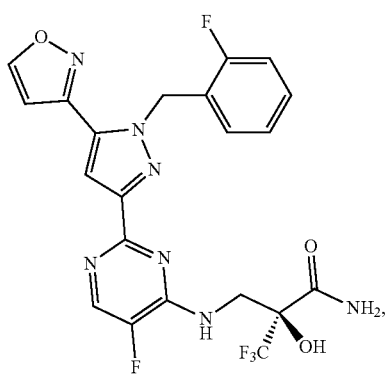

comprising the steps of:
i) coupling an amide of formula (1'):

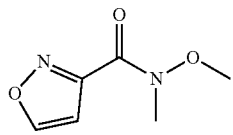
(1')

with a pyrimidine compound of formula (2):

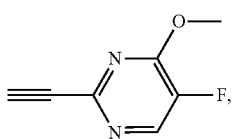
(2)

in an aprotic organic solvent in the presence of a base, to form, after quenching with an acid, an intermediate of formula (3'):

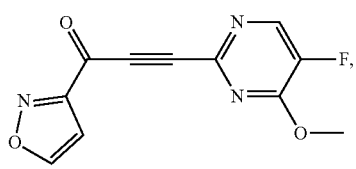
(3')

ii) at a pH>5, optionally in the presence of added N,O-dimethylhydroxylamine or a salt (e.g. HCl salt) thereof, allowing the mixture to react to form the compound of formula (4'):

(4')
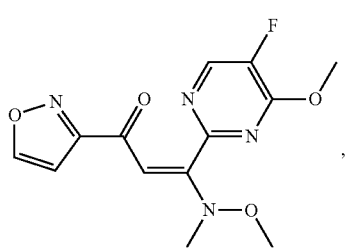

iiia) condensing the compound of formula (4') with a hydrazine (e.g., hydrazine hydrate) to form a compound of formula (24'):

(24')
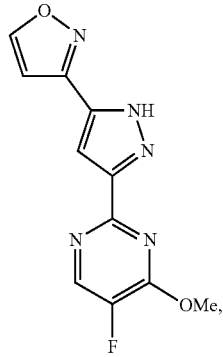

iiib) alkylating intermediate of formula (24') with an alkylating agent of formula (23A) to provide the compound of Formula V:

(23A)
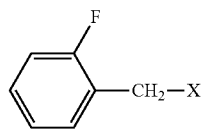

Formula V
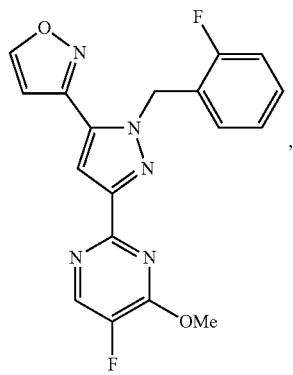

iv) de-methylating the compound of Formula V to form an alcohol compound of formula (9'):

(9')
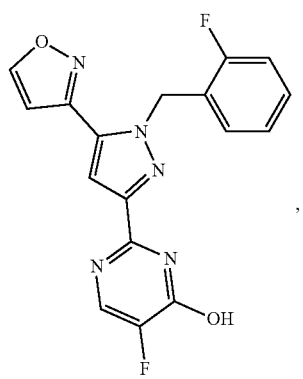

v) chlorinating the alcohol compound of formula (9') with phosphoryl chloride to form a compound of Formula VI:

Formula VI

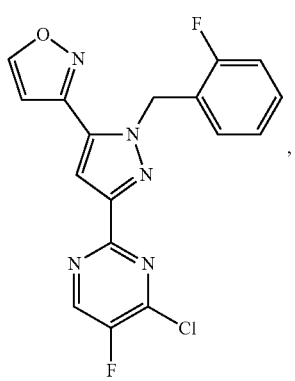

and vi) reacting an (L)-malic acid salt of an amine (21) represented by formula (18):

(18)

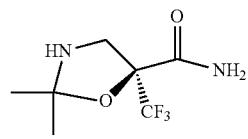

(21)

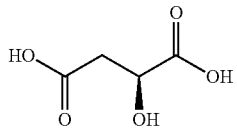

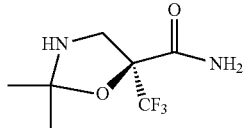

with the compound of Formula VI, optionally in the presence of a base, to yield the compound of Formula IC, wherein X is a leaving group selected from —Br, —I, —Cl, —F, and a sulfonate ester (e.g., mesylate, tosylate or triflate). In a more specific embodiment, X is —Br.

In a 34th specific embodiment, the present invention provides a process of preparing a compound of Formula ID:

Formula ID

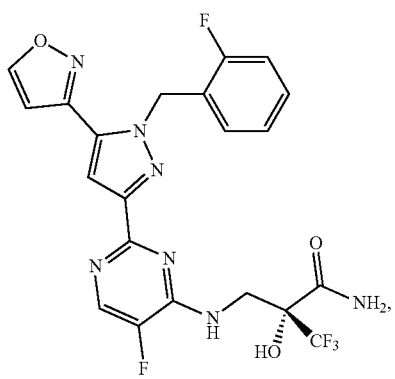

comprising the steps of:

i) coupling an amide of formula (1'):

(1')

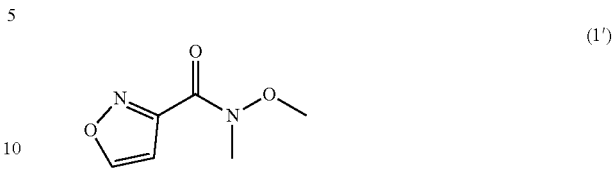

with a pyrimidine compound of formula (2):

(2)

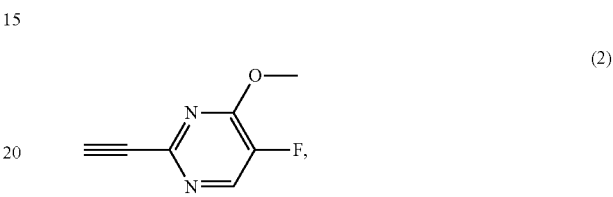

in an aprotic organic solvent in the presence of a base, to form, after quenching with acid, an intermediate of formula (3'):

(3')

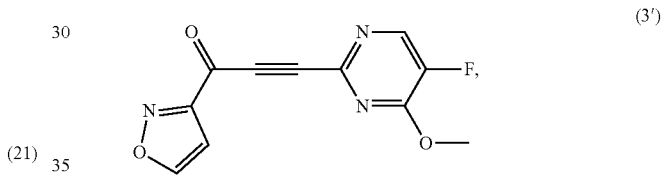

ii) at a pH>5, optionally in the presence of added N,O-dimethylhydroxylamine or a salt (e.g. HCl salt) thereof, allowing the mixture to react to form the compound of formula (4'):

(4')

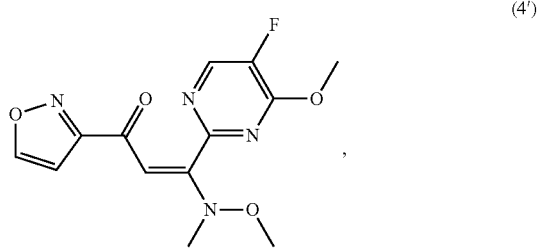 [SMILES: COc1nc(/C(=C\C(=O)c2ccon2)N(C)OC)ncc1F]

iii) condensing the compound of formula (4') with a hydrazine of formula

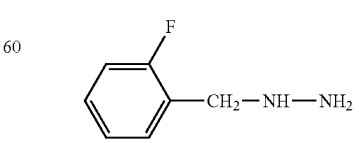

or a salt (e.g., HCl salt) thereof, optionally in the presence of a base, to form a compound of Formula V:

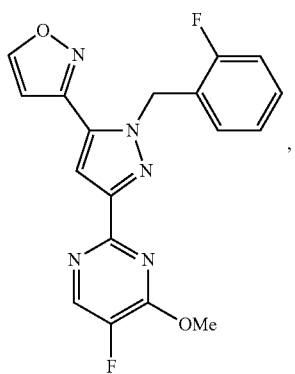
, iv) de-methylating the compound of Formula V to form an alcohol compound of formula (9'):

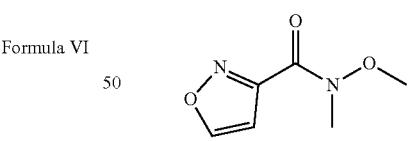
, v) chlorinating the alcohol compound of formula (9') with phosphoryl chloride to form a compound of Formula VI:

Formula VI and vi) reacting a (D)-malic acid salt of an amine (20) represented by formula (14):

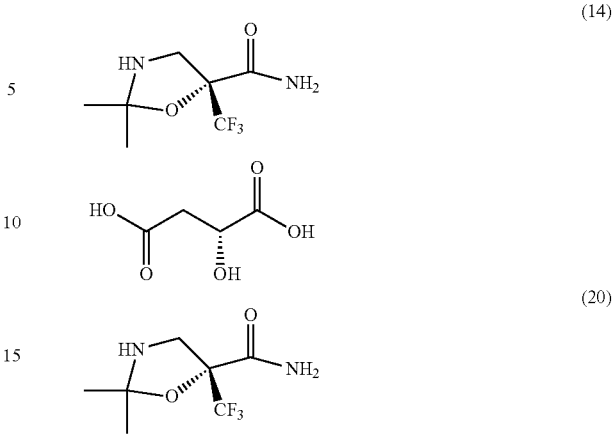

with the compound of Formula VI, optionally in the presence of a base, to yield the compound of Formula ID.

In a 35th specific embodiment, the present invention provides a process of preparing a compound of Formula ID:

Formula ID comprising the steps of:

i) coupling an amide of formula (1'):

with a pyrimidine compound of formula (2):

in an aprotic organic solvent in the presence of a base, to form, after quenching with acid, an intermediate of formula (3'):

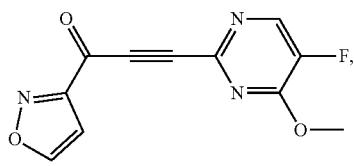

(3')

ii) at a pH>5, optionally in the presence of added N,O-dimethylhydroxylamine or a salt (e.g. HCl salt) thereof, allowing the mixture to react to form the compound of formula (4'):

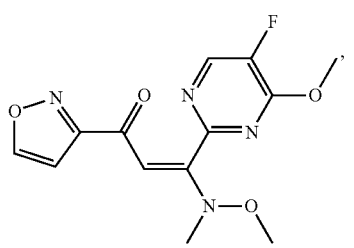

(4')

iiia) condensing the compound of formula (4') with a hydrazine (e.g., hydrazine hydrate) to form a compound of formula (24'):

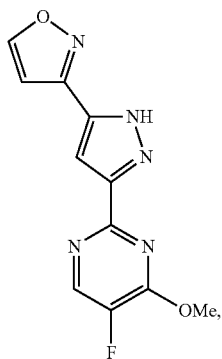

(24')

iiib) alkylating intermediate of formula (24') with an alkylating agent of formula (23A)

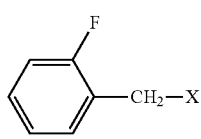

to provide the compound of Formula V:

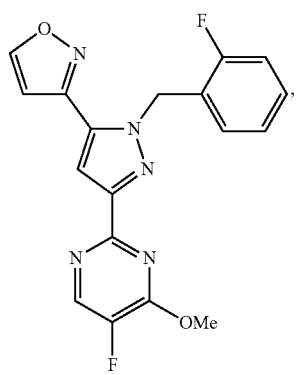

Formula V iv) de-methylating the compound of Formula V to form an alcohol compound of formula (9'):

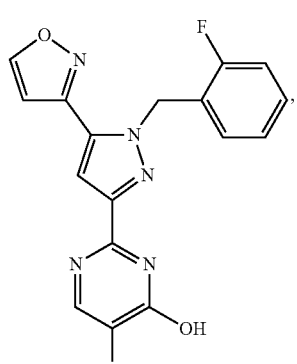

(9')

v) chlorinating the alcohol compound of formula (9') with phosphoryl chloride to form a compound of Formula VI:

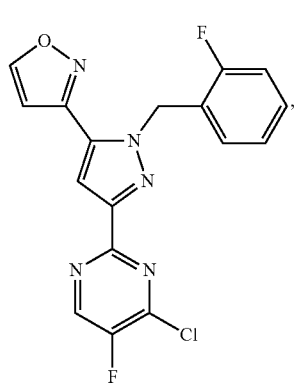

Formula VI and vi) reacting a (D)-malic acid salt of an amine (20) represented by formula (14):

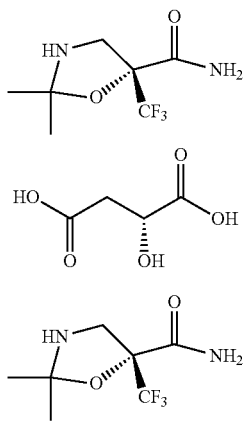

(14)

(20)

with the compound of Formula VI, optionally in the presence of a base, to yield the compound of Formula ID, wherein X is a leaving group selected from —Br, —I, —Cl, —F, and a sulfonate ester (e.g., mesylate, tosylate or triflate). In a more specific embodiment, X is —Br.

In one embodiment, the processes of the 34$^{th}$ and 35$^{th}$ specific embodiments further comprise a step of recrystallization of the compound of Formula ID to yield crystalline Form B of the compound of Formula ID. In one embodiment, the recrystallization comprises the steps of: A") dissolving the compound of Formula ID in acetonitrile and water at a temperature between 70° C. and 75° C. to form a solution of the compound; B") filtering the solution of step A") to form a filtered solution of the compound; C") heating the filtered solution at a temperature between 65° C. and 75° C. and adding water to yield a slurry; D") cooling the slurry of step C") to a temperature between 0 to 5° C. to yield crystalline Form B of the compound of Formula ID; and E") filtering, washing with a mixture of acetonitrile and water, and drying the crystalline Form B of the compound of Formula ID.

In a 36$^{th}$ specific embodiment, for the process described in the 24$^{th}$, 25$^{st}$, 26$^{th}$, 27$^{th}$, 28$^{th}$, 29$^{th}$, 30$^{th}$, 31$^{st}$, 32$^{nd}$, 33$^{rd}$ 34$^{th}$ and 35$^{th}$ specific embodiments, the compound of formula (2) is prepared by a process comprising the steps of:

a) reacting dibromopyrimidine compound of formula (5):

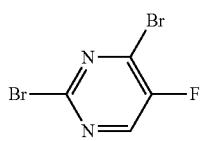

(5)

with a base in methanol or a methoxide salt in an aprotic solvent to form a bromopyrimidine compound of formula (6):

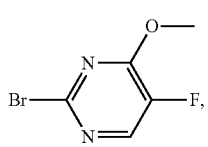

(6)

b) coupling the bromopyrimidine compound of formula (6) with ethynyltrimethylsilane, in an aprotic organic solvent in the presence of a base and a Pd catalyst, optionally in the presence of a Cu(I) catalyst, to form a compound of formula (7):

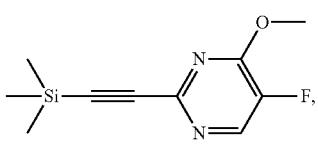

(7)

and c) de-silylating the compound of formula (7) to form the pyrimidine compound of (2).

In a 37$^{th}$ specific embodiment, for the process described in the 24$^{th}$, 25$^{st}$, 26$^{th}$, 27$^{th}$, 28$^{th}$, 29$^{th}$, 30$^{th}$, 31$^{st}$, 32$^{nd}$, 33$^{rd}$ 34$^{th}$, 35$^{th}$ and 36$^{th}$ specific embodiment, the compound of formula (1') is prepared by reacting a carboxylic acid of formula (8'):

(8')

with oxalyl chloride or an equivalent amide coupling reagent, followed by N,O-dimethylhydroxylamine or a salt (e.g. HCl salt) thereof, in the presence of a base to form the amide of formula (1').

In a 38$^{th}$ specific embodiment, for steps i) and ii) of the process described in the 13$^{th}$ to 37$^{th}$ specific embodiments, the process comprises contacting the reaction product of the reaction between the amide of formula (1') and the pyrimidine compound of formula (2) with a solution comprising N,O-dimethylhydroxylamine or a salt thereof and an acid to form the compound of formula (4'). In one embodiment, the acid is an aqueous acid. More specifically, the acid is hydrochloric acid. In another embodiment, the acid is a non-aqueous acid. More specifically, the acid is glacial acetic acid.

In some embodiments, for the process of the 1$^{st}$ to 38$^{th}$ specific embodiment, N,O-dimethylhydroxylamine or a salt (e.g., hydrochloride salt) thereof is added in step ii).

In one embodiments, for the process of the 1$^{st}$ to 11$^{th}$ and 13$^{th}$ to 37$^{th}$ specific embodiment, the intermediate of formula (3) or (3') formed in step i) is isolated and then reacted with N,O-dimethylhydroxylamine or a salt (e.g., hydrochloride salt) thereof at a pH>5 to form the compound of formula (4) or (4') respectively.

In some embodiments, for the process of the 1$^{st}$ to 38$^{th}$ specific embodiments, the base in step i) is n-butyllithium.

In some embodiments, for the process of the 1$^{st}$ to 38$^{th}$ specific embodiment, the aprotic solvent in step i) is THF, hexane or a mixture of THF and hexane.

In some embodiments, for the process of the 1$^{st}$ to 38$^{th}$ specific embodiments, 0.5 or 0.6 equivalents of N,O-dimethylhydroxylamine hydrochloride for every one equivalent of the pyrimidine compound formula (2) is used in the reaction of step ii).

In some embodiments, for the process of the 2$^{nd}$, 4$^{th}$, 6$^{th}$, 8$^{th}$, 10$^{th}$, 11$^{th}$, 12$^{th}$, 14$^{th}$, 16$^{th}$, 18$^{th}$ 20$^{th}$, 22$^{nd}$, 23$^{rd}$, 24$^{th}$, 26$^{th}$, $28^{th}$, $30^{th}$, $32^{nd}$, $34^{th}$, $36^{th}$, $37^{th}$ and $38^{th}$ specific embodiments, a base is present in the reaction of step iii). In one embodiment, the base is potassium carbonate.

In some embodiments, for the process of the $3^{rd}$, $5^{th}$, $7^{th}$, $9^{th}$, $10^{th}$, $11^{th}$, $12^{th}$, $15^{th}$, $17^{th}$, $19^{th}$, $21^{st}$, $22^{nd}$, $23^{rd}$, $25^{th}$, $27^{th}$, $29^{th}$, $31^{st}$, $33^{rd}$, $35^{th}$, $36^{th}$, $37^{th}$ and $38^{th}$ specific embodiments, a base is present in the reaction of step iiia). In one embodiment, the base is potassium carbonate.

In some embodiments, for the process of the $3^{rd}$, $5^{th}$, $7^{th}$, $9^{th}$, $10^{th}$, $11^{th}$, $12^{th}$, $15^{th}$, $17^{th}$, $19^{th}$, $21^{st}$, $22^{nd}$, $23^{rd}$, $25^{th}$, $27^{th}$, $29^{th}$, $31^{st}$, $33^{rd}$, $35^{th}$, $36^{th}$, $37^{th}$ and $38^{th}$ specific embodiments, no base is added for the reaction of step iiia).

In some embodiments, for the process of the $3^{rd}$, $5^{th}$, $7^{th}$, $9^{th}$, $10^{th}$, $11^{th}$, $12^{th}$, $15^{th}$, $17^{th}$, $19^{th}$, $21^{st}$, $22^{nd}$, $23^{rd}$, $25_{th}$, $27^{th}$, $29^{th}$, $31^{st}$, $33^{rd}$, $35^{th}$, $36^{th}$, $37^{th}$ and $38^{th}$ specific embodiments, hydrazine hydrate is used in the reaction of step iiia).

In some embodiments, for the process of the $3^{rd}$, $5^{th}$, $7^{th}$, $9^{th}$, $10^{th}$, $11^{th}$, $12^{th}$, $15^{th}$, $17^{th}$, $19^{th}$, $21^{st}$, $22^{nd}$, $23^{rd}$, $25^{th}$, $27^{th}$, $29^{th}$, $31^{st}$, $33^{rd}$, $35^{th}$, $36^{th}$, $37^{th}$ and $38^{th}$ specific embodiments, a base is present in the reaction of step iiib). In one embodiment, the base is an alkoxide. In another embodiment, the base is lithium tert-butoxide (LTB), potassium tert-butoxide (KTB), or sodium tert-butoxide (STB). In yet another embodiment, the base is lithium tert-butoxide. In another embodiment, the base is bis(trimethylsilylyl)amine (HMDS), sodium bis(trimethylsilyl)amide (NaHMDS), lithium bis(trimethylsilyl)amide (LiHMDS), potassium bis (trimethylsilyl)amide (KHMDS), NaH or lithium diisopropylamide (LDA). In one embodiment, the base is NaHMDS, LiHMDS or KHMDS.

In some embodiments, for the process of the $4^{th}$ to $12^{th}$, $16^{th}$ to $38^{th}$ specific embodiments, de-methylation in step iv) is carried out using an aqueous acid and the aqueous acid is HCL.

In some embodiments, for the process of the $8^{th}$ to $12^{th}$ and $20^{th}$ to $38^{th}$ specific embodiments, a base is present in the reaction of step vi). In one embodiment, the base is Hunig's base.

In some embodiments, for the process of the $8^{th}$ to $12^{th}$ and $20^{th}$ to $38^{th}$ specific embodiments, a base is not present in the reaction of step vi).

In some embodiments, for the process of the $10^{th}$, $11^{th}$, $12^{th}$, $22^{nd}$, $23^{rd}$, $36^{th}$, $37^{th}$ and $38^{th}$ specific embodiments, the methoxide salt in step a) is MeONa, MeOLi, MeOK or MeOCs. In one embodiment, the base is MeONa.

In some embodiments, for the process of the $10^{th}$, $11^{th}$, $12^{th}$, $22^{nd}$, $23^{rd}$, $36^{th}$, $37^{th}$ and $38^{th}$ specific embodiments, the aprotic organic solvent in step b) is an ether. In one embodiment, the ether is methyl-tert-butyl ether.

In some embodiments, for the process of the $10^{th}$, $11^{th}$, $12^{th}$, $22^{nd}$, $23^{rd}$, $36^{th}$, $37^{th}$ and $38^{th}$ specific embodiments, the base in step c) is triethylamine, Hunig's base, $Et_2NH$, $iPr_2NH$, piperidine, pyrrolidine, $K_2CO_3$, $Na_2CO_3$, $Cs_2CO_3$, or $K_3PO_4$. In one embodiment, the base is triethylamine.

In some embodiments, for the process of the $10^{th}$, $11^{th}$, $12^{th}$, $22^{nd}$, $23^{rd}$, $36^{th}$, $37^{th}$ and $38^{th}$ specific embodiments, a Cu(I) catalyst and a Pd catalyst are present in the reaction of step c). In one embodiment, the Cu(I) catalyst is CuCl, CuBr, CuI or CuOTf. In one embodiment, the Cu(I) catalyst is CuI. In another embodiment, the Pd catalyst is $PdCl_2(PPh_3)_2$.

In some embodiments, for the process of the $10^{th}$, $11^{th}$, $12^{th}$, $22^{nd}$, $23^{rd}$, $36^{th}$, $37^{th}$ and $38^{th}$ specific embodiments, de-silylation in step c) is carried out using a fluoride reactant. In some embodiments, the fluoride reactant is KF.

In some embodiments, for the process of the $11^{th}$, $12^{th}$, $23^{rd}$, $37^{th}$ and $38^{th}$ specific embodiments, oxalyl chloride is reacted with the compound of formula (8) or (8'), followed by N,O-dimethylhydroxylamine hydrochloride in the presence of a base. In one embodiment, the base is $K_2CO_3$.

Also provided by the present invention are compounds prepared by the processes of the present invention. In one embodiment, the present invention is directed to a compound of formula (3), (4), (3'), (4'), (14), (18), (15), (19), (20) or (21). In one embodiment, for compound of formula (3) or (4), $R^1$ is a 5-membered heteroaryl ring. In another embodiment, for compound of formula (3) or (4), $R^1$ is an unsubstituted 5-membered heteroaryl ring containing up to 2 ring heteroatoms selected from the group consisting of N and O.

In one aspect, the present invention provides crystalline Form A of the compound of Formula IA. In one embodiment, Form A is characterized by XRPD pattern substantially similar to that shown in FIG. 1. In another embodiment, Form A has the XRPD pattern as shown in FIG. 1. In another embodiment, Form A has at least one, two, three, four, five, six, seven or eight major peaks in an x-ray powder diffraction (XRPD) pattern selected from 4.2, 9.1, 9.8, 17.2, 17.7, 18.2, 27.5, and 36.0 degree 2θ angles.

In one embodiment, Form A has an endothermic onset (i.e., melting point) at a temperature between 155° C. and 170° C., between 160° C. and 165° C., between 162° C. and 164° C., or between 162.5° C. and 163.5° C. in a differential scanning calorimetry (DSC) profile. In another embodiment, Form A has an endothermic onset at 163.1° C.

In some embodiments, a composition of compound of formula IA has at least 70%, 80%, 90%, 95%, 98%, 99%, 99.5%, or 99.9% by weight of the compound is the crystalline Form A of the compound.

DETAILED DESCRIPTION OF THE INVENTION

Figure 1:
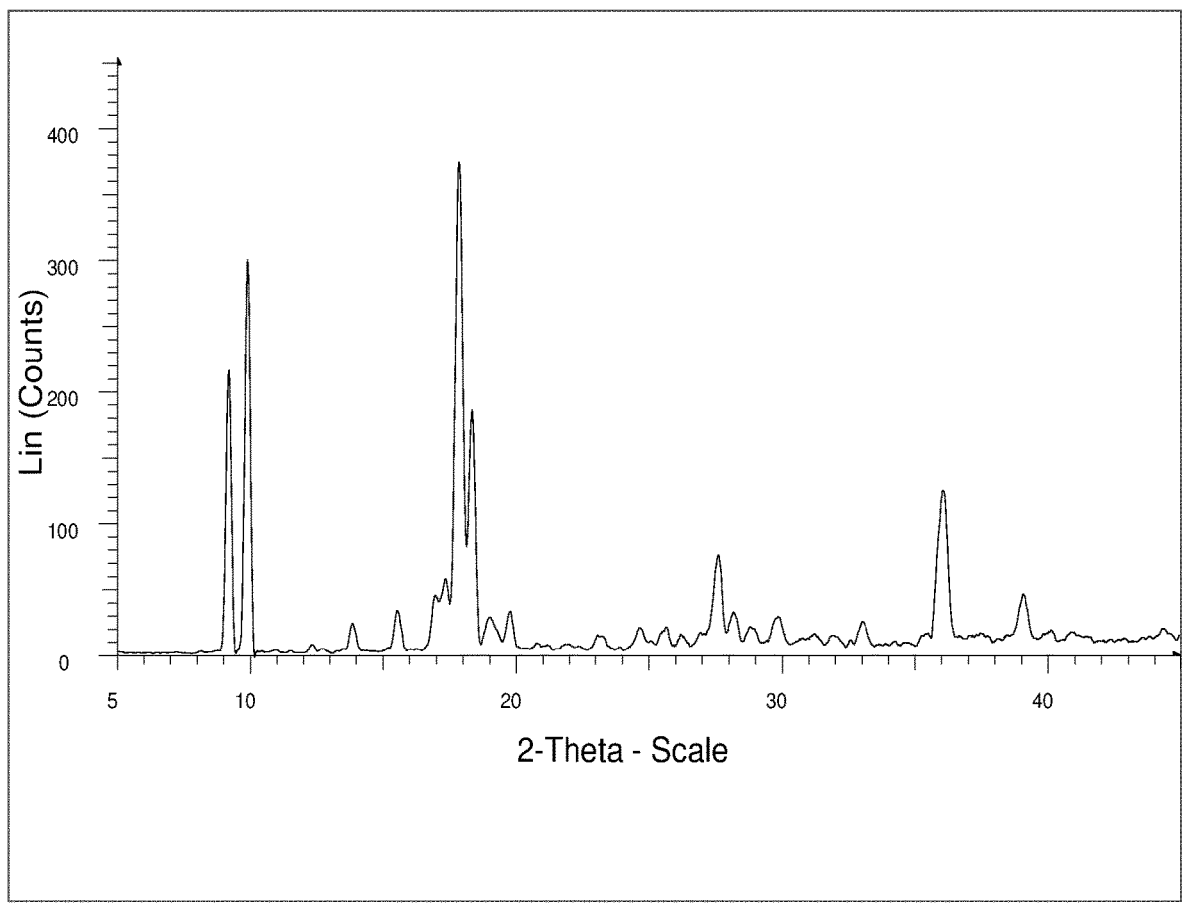
FIG. 1 shows an XRPD pattern of crystalline Form A of the compound of Formula IA.

Reference will now be made in detail to certain embodiments of the invention, examples of which are illustrated in the accompanying structures and formulae. While the invention will be described in conjunction with the enumerated embodiments, it will be understood that they are not intended to limit the invention to those embodiments. Rather, the invention is intended to cover all alternatives, modifications and equivalents that may be included within the scope of the present invention as defined by the claims. The present invention is not limited to the methods and materials described herein but include any methods and materials similar or equivalent to those described herein that could be used in the practice of the present invention. In the event that one or more of the incorporated literature references, patents or similar materials differ from or contradict this application, including but not limited to defined terms, term usage, described techniques or the like, this application controls.

Definitions and General Terminology

For purposes of this disclosure, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry", Thomas Sorrell, University Science Books, Sausalito: 1999, and "March's Advanced Organic Chemistry", 5$^{th}$ Ed., Smith, M. B. and March, J., eds. John Wiley & Sons, New York: 2001, which are herein incorporated by reference in their entirety.

The term "ring atom" refers to an atom such as C, N, O or S that is part of a ring (rings include, for example, a cycloaliphatic ring (e.g. a cycloalkyl ring), a heterocyclic ring, an aryl ring (e.g., a phenyl ring) or a heteroaryl ring).

A "substitutable ring atom" is a ring carbon or nitrogen atom bonded to at least one hydrogen atom. The hydrogen can be optionally replaced with a suitable substituent group. "Substitutable ring atom" does not include ring carbon or nitrogen atoms wherein the structure depicts that they are already attached to one or more moieties or substituents other than hydrogen and no hydrogens are available for substitution. When a certain ring is optionally substituted, it will be understood that it may be substituted at one or some or all of its substitutable ring atoms, depending on the number of substituents allowed.

In general, the term "substituted" refers to the replacement of one or more hydrogen radicals of a given structure with another specified radical substituent, different from hydrogen (some non-limiting examples would be a hydroxy, a phenyl, or an alkyl radical). If a structure or moiety is "optionally substituted" it may be substituted or unsubstituted.

When one or more position(s) of a structure can be substituted with one or more than one substituent selected from a specified group or list, the substituent or substituents at each position may be "independently selected" to be equal or the same at each position and for each instance, unless otherwise specified. For example, if a phenyl is substituted with two instances of R$^{100}$, and each R$^{100}$ is independently selected from halogen and methyl, that means that each instance of R$^{100}$ is separately selected from halogen or methyl; for instance, one R$^{100}$ may be fluoro and one may be methyl, or both may be chloro, etc. Similarly, if a substitutable atom is bonded to more than one hydrogen (e.g., CH$_3$ or NH$_2$), the substitutents may be "independently selected" to be equal or the same at each position and for each instance, unless otherwise specified. For example, if a methyl (e.g., CH$_3$) is substituted with two instances of R$^{100}$, and each R$^{100}$ is independently selected from halogen and methyl, that means that each instance of R$^{100}$ is separately selected from halogen or methyl; for instance, one R$^{100}$ may be fluoro and one may be methyl (e.g., CHF(CH$_3$), or both may be chloro (e.g., CHCl$_2$), etc.

Selection of substituents and combinations envisioned by this disclosure are only those that result in the formation of stable or chemically feasible compounds. Such choices and combinations will be apparent to those of ordinary skill in the art and may be determined without undue experimentation. The term "stable", as used herein, refers to compounds that are not substantially altered when subjected to conditions to allow for their production, detection, and, in some embodiments, their recovery, purification, and use for one or more of the purposes disclosed herein. A chemically feasible compound is a compound that can be prepared by a person skilled in the art based on the disclosures herein, supplemented, if necessary, by relevant knowledge of the art.

The phrase "up to", as used herein, refers to zero or any integer number that is equal or less than the number following the phrase. For example, "up to 3" means any one of 0, 1, 2, or 3. As described herein, a specified number range of atoms or of substituents includes any integer therein. For example, a group having from 1-4 atoms could have 1, 2, 3 or 4 atoms. When any variable occurs more than one time at any position, its definition on each occurrence is independent from every other occurrence. When a group is substituted with 0 instances of a certain variable, this means the group is unsubstituted.

Unless only one of the isomers is drawn or named specifically, structures depicted herein are also meant to include all stereoisomeric (e.g., enantiomeric, diastereomeric, atropoisomeric and cis-trans isomeric) forms of the structure; for example, the R and S configurations for each asymmetric center, Ra and Sa configurations for each asymmetric axis, (Z) and (E) double bond configurations, and cis and trans isomers. Therefore, single stereochemical isomers as well as racemates, and mixtures of enantiomers, diastereomers, and cis-trans isomers of the present compounds are within the scope of the present disclosure. Unless otherwise stated, all tautomeric forms of the compounds of the present disclosure are also within the scope of the invention.

In one embodiment, the present disclosure may include replacement of hydrogen with deuterium (i.e., $^2$H), which may afford certain therapeutic advantages resulting from greater metabolic stability (e.g., increased in vivo half-life or reduced dosage requirements) and hence may be preferred in some circumstances. Deuterium labeled compounds of the present invention can generally be prepared by following procedures analogous to those disclosed in the Schemes and/or in the Examples herein below, by substituting a deuterated reagent for a non-deuterated reagent.

The term "aliphatic", as in, for example, "aliphatic group" or "aliphatic chain", means an unbranched or branched hydrocarbon (formed by only carbon and hydrogen) chain that is completely saturated or that contains one or more units of unsaturation. Suitable aliphatic groups include, but are not limited to, linear or branched, alkyl, alkenyl, or alkynyl groups. Specific examples of aliphatic groups include, but are not limited to: methyl, ethyl, propyl, butyl, isopropyl, isobutyl, vinyl, sec-butyl, tert-butyl, butenyl, propargyl, acetylene and the like. An aliphatic group will be represented by the term "C$_{x-y}$ aliphatic"; wherein x and y are the minimum and the maximum number of carbon atoms forming the aliphatic chain. An aliphatic group will be represented by the term "C$_x$ aliphatic" to indicate that it is formed by x number of carbon atoms.

The term "alkyl" as in, for example, "alkyl chain" or "alkyl group", as used herein, refers to a saturated unbranched (e.g., linear) or branched monovalent hydrocarbon radical. A C$_x$ alkyl is an alkyl chain containing x carbon atoms, wherein x is an integer different from 0. A "C$_{x-y}$ alkyl", wherein x and y are two different integers, both different from 0, is an alkyl chain containing between x and y number of carbon atoms, inclusive. For example, a C$_{1-6}$ alkyl is an alkyl as defined above containing any number of between 1 and 6 carbon atoms. Examples of alkyl groups include, but are not limited to, methyl (i.e., C$_1$ alkyl), ethyl (i.e., $C_2$ alkyl), n-propyl (a $C_3$ alkyl), isopropyl (a different $C_3$ alkyl), n-butyl, isobutyl, s-butyl, t-butyl, pentyl, hexyl, heptyl, octyl and the like.

The term "alkenyl" (as in "alkenyl chain" or "alkenyl group"), refers to an unbranched (e.g., linear) or branched monovalent hydrocarbon radical with at least one site of unsaturation that is a carbon-carbon, $sp^2$ double bond, wherein the alkenyl radical includes radicals having "cis" and "trans" orientations, or using an alternative nomenclature, "E" and "Z" orientations. Examples of alkenyls include, but are not limited to, vinyl, allyl and the like. A $C_x$ alkenyl is an alkenyl chain containing x carbon atoms, wherein x is an integer different from 0 or 1. Alternatively, an alkenyl group will be represented by the term "$C_{x-y}$ alkenyl"; wherein x and y are the minimum and the maximum number of carbon atoms forming the alkenyl chain.

The term "alkynyl" (as in "alkynyl chain" or "alkynyl group"), refers to an unbranched (e.g., linear) or branched monovalent hydrocarbon radical with at least one site of unsaturation that is a carbon-carbon sp triple bond. Examples include, but are not limited to, ethynyl, propynyl, and the like. A $C_x$ alkynyl is an alkynyl chain containing x carbon atoms, wherein x is an integer different from 0 or 1. Alternatively, an alkynyl group will be represented by the term "$C_{x-y}$ alkynyl"; wherein x and y are the minimum and the maximum number of carbon atoms forming the alkynyl chain.

The term "cycloaliphatic", as in "cycloaliphatic ring" or "cycloaliphatic group" refers to a ring system formed only by carbon and hydrogen atoms that is completely saturated or that contains one or more units of unsaturation but which is not aromatic. A $C_x$ cycloaliphatic is a cycloaliphatic ring containing x carbon atoms, wherein x is an integer different from 0. Alternatively, a cycloaliphatic ring will be represented by the term "$C_{x-y}$ cycloaliphatic"; wherein x and y are the minimum and the maximum number of carbon atoms forming the cycloaliphatic ring. Suitable cycloaliphatic groups include, but are not limited to, cycloalkyl, cycloalkenyl, and cycloalkynyl. Examples of aliphatic groups include cyclopropyl, cyclobutyl, cyclopentyl, cyclopentenyl, cyclohexyl, cyclohexenyl, cycloheptyl, cycloheptenyl, norbornyl, cyclooctyl, cyclononyl, cyclodecyl, cycloundecyl, cyclododecyl, and the like. The term "cycloaliphatic", also includes polycyclic ring systems (e.g., bicyclic, tricyclic or tetracyclic)). The polycyclic ring system may be a bridged, a fused, or a spiro system.

"Bridged" ring systems comprise two rings which share two non-adjoining ring atoms.

"Fused" ring systems comprise two rings which share two adjoining ring atoms.

"Spiro" ring systems comprise two rings which share one adjoining ring atom.

The term "cycloalkyl", as in "cycloalkyl ring" or "cycloalkyl group", as used herein, refers to a ring system formed only by carbon and hydrogen atoms which is completely saturated. Suitable cycloalkyl groups include, but are not limited to, cyclopropyl, cyclobutyl, cyclopentyl, cyclohexyl, cycloheptyl, cycloheptenyl, norbornyl, cyclooctyl, cyclononyl, cyclodecyl, cycloundecyl, cyclododecyl, and the like. A cycloalkyl ring will be represented by the term "$C_{x-y}$ cycloalkyl"; wherein x and y are the minimum and the maximum number of carbon atoms forming the cycloalkyl ring. The term "cycloalkyl" also includes polycyclic ring systems (e.g., bicyclic, tricyclic or tetracyclic). The polycyclic ring system may be a bridged, a fused, or a spiro system.

As used herein, the term "aryl" (as in "aryl ring" or "aryl group"), refers to a ring system formed only by carbon atoms that is aromatic. The term also includes polycyclic ring systems (e.g., bicyclic, tricyclic, tetracyclic, etc.). Examples of aryl rings include, but are not limited to, phenyl, naphthyl, indenyl, fluorenyl, and anthracenyl.

The term "heteroatom" refers to one or more of oxygen, sulfur, nitrogen, phosphorus, or silicon, including any oxidized form of nitrogen, sulfur, phosphorus, or silicon, and including the quaternized form of any basic nitrogen.

A ring that includes atoms other than just carbon is termed a "heterocyclyl" (or "heterocycle" or "heterocyclic"), as in "heterocyclyl group" or "heterocyclyl ring" or a heteroaryl" (or "heteroaromatic"), as in "heteroaryl group" or "heteroaryl ring". Heterocyclyl and heteroaryl rings include at least one ring atom other than carbon to form the ring. The non-carbon ring atom can be any suitable atom, but often is selected from nitrogen, oxygen, or sulfur. Heterocyclyl rings are completely saturated (e.g., piperidinyl) or contain one or more units of unsaturation but is not aromatic (e.g., 1,2,3,4-tetrahydropyridinyl or 1,2-dihydropyridinyl). Heteroaryl rings are aromatic (e.g., pyridinyl). The terms heterocyclyl and heteroaryl also include polycyclic ring systems (e.g., bicyclic, tricyclic or tetracyclic). The polycyclic ring system may be a bridged, a fused, or a spiro system.

Heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, and 5-imidazolidinyl. Examples of bicyclic heterocyclic ring systems include, but are not limited to: 2-oxa-bicyclo[2.2.2]octyl, 1-aza-bicyclo[2.2.2]octyl.

Heteroaryl rings include, but are not limited to the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl. Examples of bicyclic heteroaryl rings include, but are not limited to: indazole, pyrazolopyrimidine, imidazopyridine, etc.

As used herein, the term "alkoxy" refers to an alkyl group, as previously defined, attached to the molecule through an oxygen atom. An alkoxy group may be represented by —O—($C_{x-y}$ alkyl), wherein x and y represent the minimum and maximum number of carbons of the alkyl chain.

As used herein, the terms "halogen" or "halo" mean F, Cl, Br, or I.

The terms "haloalkyl", "haloalkenyl", "haloaliphatic", and "haloalkoxy" mean alkyl, alkenyl, aliphatic or alkoxy, as the case may be, substituted with one or more halogen atoms. For example a $C_{1-3}$ haloalkyl could be, for example —CFHCH$_2$CHF$_2$ and a $C_{1-2}$ haloalkoxy could be, for example —OC(Br)HCHF$_2$. This term includes perhalogenated alkyl groups, such as —CCl$_3$ and —CF$_2$CClF$_2$.

The term "fluoroalkyl" means alkyl substituted with one or more fluorine atoms.

This term includes perfluorinated alkyl groups, such as —$CF_3$ and —$CF_2CF_3$.

As used herein, the term "cyano" refers to —CN or —C≡N.

As used herein, an "amino" group refers to —$NH_2$.

The term "hydroxyl" or "hydroxy" refers to —OH.

As used herein, a "carbonyl", used alone or in connection with another group refers to —C(O)— or —C(=O)—

As used herein, an "oxo" refers to =O. When an 'oxo' group is listed as a possible substituent on a ring or another moiety or group (e.g. an alkyl chain) it will be understood that the bond between the oxygen in said oxo group and the ring, or moiety or group it is attached to will be a double bond.

The compounds of the invention are defined herein by their chemical structures and/or chemical names. Where a compound is referred to by both a chemical structure and a chemical name, and the chemical structure and chemical name conflict, the chemical structure is determinative of the compound's identity.

Substituents, such as for example, $R^1$, $R^2$, and $R^3$, etc., are generally defined when introduced and retain that definition throughout the specification and in all independent claims, unless otherwise specified.

As used herein, "amide coupling agent" or "amide coupling reagent" means a compound that reacts with the hydroxyl moiety of a carboxy moiety thereby rendering it susceptible to nucleophilic attack. Exemplary amide coupling agents include DIC (diisopropylcarbodiimide), EDCI (1-ethyl-3-(3-dimethylaminopropyl)carbodiimide), DCC (dicyclohexylcarbodiimide), BOP (benzotriazol-1-yloxy-tris(dimethylamino)-phosphonium hexafluorophosphate), pyBOP ((benzotriazol-1-yloxy)tripyrrolidinophosphonium hexafluorophosphate), etc.

The term "solvent" as used herein refers to an individual solvent or to a mixture of solvents that result in the desired properties of the solvent mixture. For instance, an aprotic organic solvent could be toluene, or it could be a mixture of toluene and another aprotic solvent such as DMF. Thus, as used herein the term aprotic organic solvent could also encompass a toluene/DMF mixture. As another example, a protic solvent could encompass water or a mixture of water and methanol.

As used herein, a "protic solvent" is a solvent that has a hydrogen atom bound to a polar group, such as oxygen (as in a hydroxyl group) or nitrogen (as in an amine group). In general terms, any solvent that contains labile H+ is called a protic solvent. The molecules of such solvents readily donate protons (H+) to reagents. Conversely, "aprotic solvents" cannot easily donate hydrogen. Aprotic solvents are usually classified as either polar aprotic or non-polar (or apolar) aprotic depending on the values of their dielectric constants. Protic solvents are usually polar protic solvents and have high dielectric constants and high polarity.

Some common characteristics of protic solvents are the ability to display hydrogen bonding, having acidic hydrogens (although they may be very weakly acidic such as ethanol) and that they are able to dissolve salts. Examples include water, most alcohols, formic acid, hydrogen fluoride, nitromethane, acetic acid and ammonia.

Some common characteristics of aprotic solvents are that they can accept hydrogen bonds, do not have acidic hydrogen and are able to dissolve salts. These criteria are relative and very qualitative. A range of acidities are recognized for aprotic solvents. Their ability to dissolve salts depends strongly on the nature of the salt.

Polar aprotic solvents are solvents that will dissolve many salts. They lack an acidic hydrogen. Consequently, they are not hydrogen bond donors. These solvents generally have intermediate dielectric constants and polarity. Although it discourages the use of the term "polar aprotic", IUPAC describes such solvents as having both high dielectric constants and high dipole moments, an example being acetonitrile. Other solvents meeting IUPAC's criteria include N,N-dimethylformamide (DMF), N,N-dimethylacetamide (DMA), N-methylpyrrolidone (NMP), hexamethylphosporamide (HMPA), tetrahydrofuran, ethyl acetate, acetone, acetonitrile (MeCN), and dimethylsulfoxide (DMSO). Apolar or non-polar aprotic solvents usually have small dielectric constants. Some examples of non-polar aprotic solvents are hexane and other alkanes, benzene, toluene, 1, 4-dioxane, chloroform, ethers such as diethyl ether, dichloromethane, dichloroethane, etc.

The term "equivalent", as used herein, when discussing an amount of a reagent used, refers to "molar equivalent". For instance, one equivalent of reagent A for each equivalent of reagent B, means one mol of reagent A for each mol of reagent B is used in the reaction. A mol is defined as the number that results when the total weight of a substance used is divided by the molecular weight of said substance, both weights being in the same units (for example, grams).

The compounds of the invention are defined herein by their chemical structures and/or chemical names. Where a compound is referred to by both a chemical structure and a chemical name, and the chemical structure and chemical name conflict, the chemical structure is determinative of the compound's identity.

Embodiments

Novel processes for preparing compounds of Formula I are described herein.

In a first embodiment, compounds of Formula I are compounds of Formula II. In a second embodiment, compounds of Formula I are compounds of Formula III. In a third embodiment, compounds of Formula I are compounds of Formula IV.

A first process for making a compound of Formula II, a compound of Formula III or a compound of Formula IV comprises the steps of:

i) coupling an appropriate amount of intermediate amide (1) with intermediate pyrimidine (2), in a suitable aprotic organic solvent, at a suitable temperature, in the presence of an appropriate amount of a suitable base, to afford, after quenching with an acid, a solution of intermediate (3)

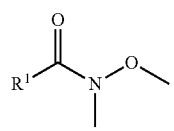

(1)

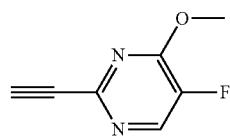

(2)

-continued

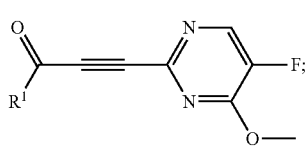
(3)

and ii) at pH>5, optionally after addition of an appropriate amount of N,O-dimethylhydroxylamine or a salt (e.g., HCl salt) thereof, in a suitable solvent, at a suitable temperature, allowing the mixture to react to afford intermediate (4)

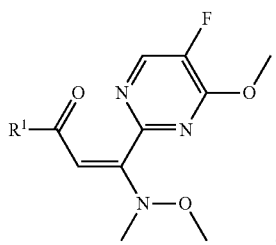
(4)

A second process for making a compound of Formula II, a compound of Formula III or a compound of Formula IV, comprises the steps of:
i) coupling an appropriate amount of intermediate amide (1) with intermediate pyrimidine (2), in a suitable aprotic organic solvent, at a suitable temperature, in the presence of an appropriate amount of a suitable base, to afford, after quenching with an acid, a solution of intermediate (3);
ii) at pH>5, optionally after addition of an appropriate amount of N,O-dimethylhydroxylamine or a salt (e.g., HCl salt) thereof, in a suitable solvent, at a suitable temperature, allowing the mixture to react to afford intermediate (4); and
iii) condensing intermediate (4) with an appropriate amount of a hydrazine of formula $R^2$—$CH_2$—NH—$NH_2$ or a salt (e.g., HCl salt) thereof, optionally in the presence of an appropriate amount of a suitable base, in a suitable protic or aprotic solvent, at a suitable temperature, affording a compound of Formula II.

A third process for making a compound of Formula II, a compound of Formula III or a compound of Formula IV, comprises the steps of:
i) coupling an appropriate amount of intermediate amide (1) with intermediate pyrimidine (2), in a suitable aprotic organic solvent, at a suitable temperature, in the presence of an appropriate amount of a suitable base, to afford, after quenching with an acid, a solution of intermediate (3);
ii) at pH>5, optionally after addition of an appropriate amount of N,O-dimethylhydroxylamine or a salt (e.g., HCl salt) thereof, in a suitable solvent, at a suitable temperature, allowing the mixture to react to afford intermediate (4);
iiia) condensing the compound of formula (4) with an appropriate amount of hydrazine, in a suitable protic or aprotic solvent, at a suitable temperature, affording a compound of formula (24); and
iiib) alkylating the compound of formula (24) with an appropriate amount of an alkylating agent of formula (22), optionally in the presence of an appropriate amount of a suitable base, in a suitable protic or aprotic solvent, at a suitable temperature, affording the compound of Formula II.

A fourth process for making a compound of Formula II, a compound of Formula III or a compound of Formula IV comprises the steps of:
a) reacting dibromopyrimidine (5) with an appropriate amount of a suitable base, in methanol or a methoxide salt in a suitable aprotic solvent, at a suitable temperature, to provide, after work up, a solution of bromopyrimidine intermediate (6) in a suitable aprotic solvent

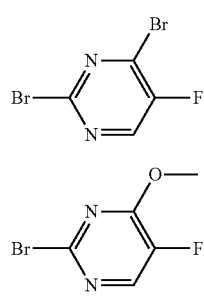
(5)

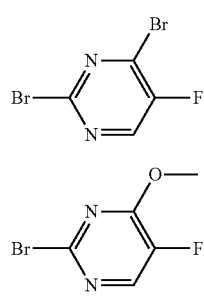
(6)

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst; to afford, after workup, a solution of intermediate (7) in a suitable solvent

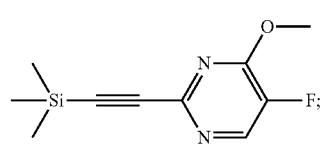
(7)

c) de-silylating intermediate (7) with an appropriate amount of a suitable de-methylation reactant, a suitable acid or a suitable base, in a suitable solvent, at a suitable temperature, to provide pyrimidine intermediate (2);
i) coupling an appropriate amount of intermediate amide (1) with pyrimidine (2), in a suitable aprotic organic solvent, at a suitable temperature, in the presence of an appropriate amount of a suitable base, to afford, after quenching with an acid, a solution of intermediate (3);
ii) at pH>5, optionally after addition of an appropriate amount of N,O-dimethylhydroxylamine or a salt (e.g., HCl salt) thereof, in a suitable solvent, at a suitable temperature, allowing the mixture to react to afford intermediate (4); and
iii) condensing intermediate (4) with an appropriate amount of a hydrazine of formula $R^2$—$CH_2$—NH—$NH_2$ or a salt (e.g., HCl salt) thereof, optionally in the presence of an appropriate amount of a suitable base, in a suitable protic or aprotic solvent, at a suitable temperature, affording a compound of Formula II.

A fifth process for making a compound of Formula II, a compound of Formula III or a compound of Formula IV comprises the steps of:
a) reacting dibromopyrimidine (5) with an appropriate amount of a suitable base, in methanol or a methoxide salt in a suitable aprotic solvent, at a suitable temperature, to provide, after work up, a solution of bromopyrimidine intermediate (6) in a suitable aprotic solvent

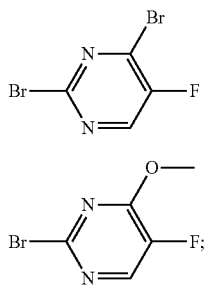
(5)

(6)

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst; to afford, after workup, a solution of intermediate (7) in a suitable solvent

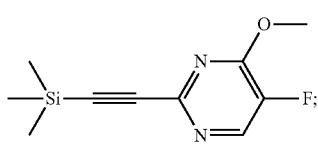
(7)

c) de-silylating intermediate (7) with an appropriate amount of a suitable de-methylation reactant, a suitable acid or a suitable base, in a suitable solvent, at a suitable temperature, to provide pyrimidine intermediate (2);

i) coupling an appropriate amount of intermediate amide (1) with pyrimidine (2), in a suitable aprotic organic solvent, at a suitable temperature, in the presence of an appropriate amount of a suitable base, to afford, after quenching with an acid, a solution of intermediate (3);

ii) at pH>5, optionally after addition of an appropriate amount of N,O-dimethylhydroxylamine or a salt (e.g., HCl salt) thereof, in a suitable solvent, at a suitable temperature, allowing the mixture to react to afford intermediate (4);

iiia) condensing the compound of formula (4) with an appropriate amount of hydrazine, in a suitable protic or aprotic solvent, at a suitable temperature, affording a compound of formula (24); and iiib) alkylating the compound of formula (24) with an appropriate amount of an alkylating agent of formula (22), optionally in the presence of an appropriate amount of a suitable base, in a suitable protic or aprotic solvent, at a suitable temperature, affording the compound of Formula II.

A sixth process for making a compound of Formula II, a compound of Formula III or a compound of Formula IV comprises the steps of:

a) reacting dibromopyrimidine (5) with an appropriate amount of a suitable base, in methanol or a methoxide salt in a suitable aprotic solvent, at a suitable temperature, to provide, after workup, a solution of a bromopyrimidine intermediate (6) in a suitable aprotic solvent;

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst; to afford after workup, a solution of intermediate (7) in a suitable solvent;

c) de-silylating intermediate (7) with an appropriate amount of a suitable fluoride reactant, a suitable acid or a suitable base, in a suitable solvent, at a suitable temperature, to provide pyrimidine intermediate (2);

d) amidating carboxylic acid (8) by reacting it with an appropriate amount of oxalyl chloride or an equivalent amide coupling reagent, in a suitable aprotic organic solvent, at a suitable temperature, in the presence of an appropriate amount of a suitable catalyst; followed by an appropriate amount of N,O-dimethylhydroxylamine or a salt (e.g. HCl salt) thereof, in the presence of an appropriate excess of a suitable base, at a suitable temperature, in a suitable solvent to afford amide (1)

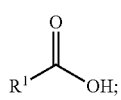
(8)

i) coupling an appropriate amount of intermediate amide (1) with intermediate pyrimidine (2), in a suitable aprotic organic solvent, at a suitable temperature, in the presence of an appropriate amount of a suitable base, to afford, after quenching with an acid, a solution of intermediate (3);

ii) at pH>5, optionally after addition of an appropriate amount of N,O-dimethylhydroxylamine or a salt (e.g., HCl salt) thereof, in a suitable solvent, at a suitable temperature, allowing the mixture to react to afford intermediate (4); and iii) condensing intermediate (4) with an appropriate amount of a hydrazine of formula $R^2$—$CH_2$—NH—$NH_2$ or a salt (e.g., HCl salt) thereof, optionally in the presence of an appropriate amount of a suitable base, in a suitable protic solvent, at a suitable temperature, affording a compound of Formula II.

A seventh process for making a compound of Formula II, a compound of Formula III or a compound of Formula IV comprises the steps of:

a) reacting dibromopyrimidine (5) with an appropriate amount of a suitable base, in methanol or a methoxide salt in a suitable aprotic solvent, at a suitable temperature, to provide, after workup, a solution of a bromopyrimidine intermediate (6) in a suitable aprotic solvent;

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst; to afford after workup, a solution of intermediate (7) in a suitable solvent;

c) de-silylating intermediate (7) with an appropriate amount of a suitable fluoride reactant, a suitable acid or a suitable base, in a suitable solvent, at a suitable temperature, to provide pyrimidine intermediate (2);

d) amidating carboxylic acid (8) by reacting it with an appropriate amount of oxalyl chloride or an equivalent amide coupling reagent, in a suitable aprotic organic solvent, at a suitable temperature, in the presence of an appropriate amount of a suitable catalyst; followed by an appropriate amount of N,O-dimethylhydroxylamine or a salt (e.g. HCl salt) thereof, in the presence of an appropriate excess of a suitable base, at a suitable temperature, in a suitable solvent to afford amide (1)

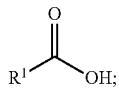

(8)

i) coupling an appropriate amount of intermediate amide (1) with intermediate pyrimidine (2), in a suitable aprotic organic solvent, at a suitable temperature, in the presence of an appropriate amount of a suitable base, to afford, after quenching with an acid, a solution of intermediate (3);

ii) at pH>5, optionally after addition of an appropriate amount of N,O-dimethylhydroxylamine or a salt (e.g., HCl salt) thereof, in a suitable solvent, at a suitable temperature, allowing the mixture to react to afford intermediate (4);

iiia) condensing the compound of formula (4) with an appropriate amount of hydrazine, in a suitable protic or aprotic solvent, at a suitable temperature, affording a compound of formula (24); and iiib) alkylating the compound of formula (24) with an appropriate amount of an alkylating agent of formula (22), optionally in the presence of an appropriate amount of a suitable base, in a suitable protic or aprotic solvent, at a suitable temperature, affording the compound of Formula II.

An eighth process for making a compound of Formula III, or a compound of Formula IV comprises the steps of:

a) reacting dibromopyrimidine (5) with an appropriate amount of a suitable base, in methanol or a methoxide salt in a suitable aprotic solvent, at a suitable temperature, to provide, after workup, a solution of a bromopyrimidine intermediate (6) in a suitable aprotic solvent;

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst; to afford, after workup, a solution of intermediate (7) in a suitable solvent;

c) de-silylating intermediate (7) with an appropriate amount of a suitable fluoride reactant, a suitable acid or a suitable base, in a suitable solvent, at a suitable temperature, to provide pyrimidine intermediate (2);

d) amidating carboxylic acid (8) by reacting it with an appropriate amount of oxalyl chloride or an equivalent amide coupling reagent, in a suitable aprotic organic solvent, at a suitable temperature, in the presence of an appropriate amount of a suitable catalyst; followed by an appropriate amount of N,O-dimethylhydroxylamine or salt (e.g. HCl salt) thereof, in the presence of an appropriate excess of a suitable base, at a suitable temperature, in a suitable solvent to afford amide (1);

i) coupling an appropriate amount of intermediate amide (1) with intermediate pyrimidine (2), in a suitable aprotic organic solvent, at a suitable temperature, in the presence of an appropriate amount of a suitable base, to afford, after quenching with an acid, a solution of intermediate (3);

ii) at pH>5, optionally after addition of an appropriate amount of N, O-dimethylhydroxylamine or a salt (e.g., HCl salt) thereof, in a suitable solvent, at a suitable temperature, allowing the mixture to react to afford intermediate (4);

iii) condensing intermediate (4) with an appropriate amount of a hydrazine of formula $R^2$—$CH_2$—NH—$NH_2$ or a salt (e.g., HCl salt) thereof, optionally in the presence of an appropriate amount of a suitable base, in a suitable protic or aprotic solvent, at a suitable temperature, affording a compound of Formula II;

iv) de-methylating the compound of Formula II by reacting it with an appropriate amount of a suitable de-methylation reagent, in a suitable solvent, at a suitable temperature, to afford alcohol (9)

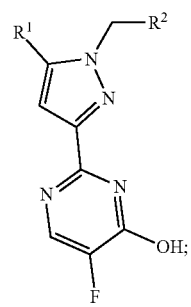

(9)

and v) chlorinating alcohol (9) with an appropriate amount of phosphoryl chloride and, optionally, an appropriate amount of a suitable base, at a suitable temperature, optionally in a suitable aprotic organic solvent to afford the chloropyrimidine of Formula III.

A ninth process for making a compound of Formula III, or a compound of Formula IV comprises the steps of:

a) reacting dibromopyrimidine (5) with an appropriate amount of a suitable base, in methanol or a methoxide salt in a suitable aprotic solvent, at a suitable temperature, to provide, after workup, a solution of a bromopyrimidine intermediate (6) in a suitable aprotic solvent;

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst; to afford, after workup, a solution of intermediate (7) in a suitable solvent;

c) de-silylating intermediate (7) with an appropriate amount of a suitable fluoride reactant, a suitable acid or a suitable base, in a suitable solvent, at a suitable temperature, to provide pyrimidine intermediate (2);

d) amidating carboxylic acid (8) by reacting it with an appropriate amount of oxalyl chloride or an equivalent amide coupling reagent, in a suitable aprotic organic solvent, at a suitable temperature, in the presence of an appropriate amount of a suitable catalyst; followed by an appropriate amount of N,O-dimethylhydroxylamine or salt (e.g. HCl salt) thereof, in the presence of an appropriate excess of a suitable base, at a suitable temperature, in a suitable solvent to afford amide (1);

i) coupling an appropriate amount of intermediate amide (1) with intermediate pyrimidine (2), in a suitable aprotic organic solvent, at a suitable temperature, in the presence of an appropriate amount of a suitable base, to afford, after quenching with an acid, a solution of intermediate (3);

ii) at pH>5, optionally after addition of an appropriate amount of N, O-dimethylhydroxylamine or a salt (e.g., HCl salt) thereof, in a suitable solvent, at a suitable temperature, allowing the mixture to react to afford intermediate (4);

iiia) condensing the compound of formula (4) with an appropriate amount of hydrazine, in a suitable protic or aprotic solvent, at a suitable temperature, affording a compound of formula (24);

iiib) alkylating the compound of formula (24) with an appropriate amount of an alkylating agent of formula (22), optionally in the presence of an appropriate amount of a suitable base, in a suitable protic or aprotic solvent, at a suitable temperature, affording the compound of Formula II;

iv) de-methylating the compound of Formula II by reacting it with an appropriate amount of a suitable de-methylation reagent, in a suitable solvent, at a suitable temperature, to afford alcohol (9)

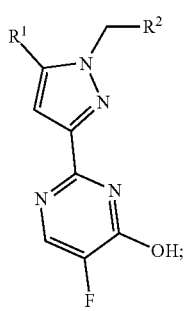

(9)

and v) chlorinating alcohol (9) with an appropriate amount of phosphoryl chloride and, optionally, an appropriate amount of a suitable base, at a suitable temperature, optionally in a suitable aprotic organic solvent to afford the chloropyrimidine of Formula III.

A tenth process for making a compound of Formula IV, comprises the steps of:

a) reacting dibromopyrimidine (5) with an appropriate amount of a suitable base, in in methanol or a suitable methoxide salt in a suitable aprotic solvent, at a suitable temperature, to provide, after workup, a solution of a bromopyrimidine intermediate (6) in a suitable aprotic solvent;

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst; to afford, after workup, a solution of intermediate (7) in a suitable solvent;

c) de-silylating intermediate (7) with an appropriate amount of a suitable fluoride reactant, a suitable acid or a suitable base, in a suitable solvent, at a suitable temperature, to provide pyrimidine intermediate (2);

d) amidating carboxylic acid (8) by reacting it with an appropriate amount of oxalyl chloride or an equivalent amide coupling reagent, in a suitable aprotic organic solvent, at a suitable temperature, in the presence of an appropriate amount of a suitable catalyst; followed by an appropriate amount of N,O-dimethylhydroxylamine or a salt (e.g. HCl salt) thereof, in the presence of an appropriate excess of a suitable base, at a suitable temperature, in a suitable solvent to afford amide (1);

i) coupling an appropriate amount of intermediate amide (1) with intermediate pyrimidine (2), in a suitable aprotic organic solvent, at a suitable temperature, in the presence of an appropriate amount of a suitable base, to afford, after quenching with an acid, a solution of intermediate (3);

ii) at pH>5, optionally after addition of an appropriate amount of N, O-dimethylhydroxylamine or a salt (e.g., HCl salt) thereof, in a suitable solvent, at a suitable temperature, allowing the mixture to react to afford intermediate (4);

iii) condensing intermediate (4) with an appropriate amount of a hydrazine of formula $R^2$—$CH_2$—NH—$NH_2$ or a salt (e.g., HCl salt) thereof, optionally in the presence of an appropriate amount of a suitable base, in a suitable protic or aprotic solvent, at a suitable temperature, affording a compound of Formula II;

iv) de-methylating the compound of Formula II by reacting it with an appropriate amount of a suitable de-methylation reagent, in a suitable solvent, at a suitable temperature, to afford alcohol (9);

v) chlorinating alcohol (9) with an appropriate amount of phosphoryl chloride and, optionally, an appropriate amount of a suitable base, at a suitable temperature, optionally in a suitable aprotic organic solvent to afford the chloropyrimidine of Formula III; and vi) reacting an appropriate amount of an amine (10) with the chloropyrimidine of Formula III, optionally in the presence of an appropriate amount of a suitable base, in a suitable solvent, at a suitable temperature, to yield an amino-pyrimidine of Formula IV

(10)

An eleventh process for making a compound of Formula IV, comprises the steps of:

a) reacting dibromopyrimidine (5) with an appropriate amount of a suitable base, in in methanol or a suitable methoxide salt in a suitable aprotic solvent, at a suitable temperature, to provide, after workup, a solution of a bromopyrimidine intermediate (6) in a suitable aprotic solvent;

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst; to afford, after workup, a solution of intermediate (7) in a suitable solvent;

c) de-silylating intermediate (7) with an appropriate amount of a suitable fluoride reactant, a suitable acid or a suitable base, in a suitable solvent, at a suitable temperature, to provide pyrimidine intermediate (2);

d) amidating carboxylic acid (8) by reacting it with an appropriate amount of oxalyl chloride or an equivalent amide coupling reagent, in a suitable aprotic organic solvent, at a suitable temperature, in the presence of an appropriate amount of a suitable catalyst; followed by an appropriate amount of N,O-dimethylhydroxylamine or a salt (e.g. HCl salt) thereof, in the presence of an appropriate excess of a suitable base, at a suitable temperature, in a suitable solvent to afford amide (1);

i) coupling an appropriate amount of intermediate amide (1) with intermediate pyrimidine (2), in a suitable aprotic organic solvent, at a suitable temperature, in the presence of an appropriate amount of a suitable base, to afford, after quenching with an acid, a solution of intermediate (3);

ii) at pH>5, optionally after addition of an appropriate amount of N,O-dimethylhydroxylamine or a salt (e.g., HCl salt) thereof, in a suitable solvent, at a suitable temperature, allowing the mixture to react to afford intermediate (4);

iiia) condensing the compound of formula (4) with an appropriate amount of hydrazine, in a suitable protic or aprotic solvent, at a suitable temperature, affording a compound of formula (24);

iiib) alkylating the compound of formula (24) with an appropriate amount of an alkylating agent of formula (22), optionally in the presence of an appropriate amount of a suitable base, in a suitable protic or aprotic solvent, at a suitable temperature, affording the compound of Formula II;

iv) de-methylating the compound of Formula II by reacting it with an appropriate amount of a suitable de-methylation reagent, in a suitable solvent, at a suitable temperature, to afford alcohol (9);

v) chlorinating alcohol (9) with an appropriate amount of phosphoryl chloride and, optionally, an appropriate amount of a suitable base, at a suitable temperature, optionally in a suitable aprotic organic solvent to afford the chloropyrimidine of Formula III; and vi) reacting an appropriate amount of an amine (10) with the chloropyrimidine of Formula III, optionally in the presence of an appropriate amount of a suitable base, in a suitable solvent, at a suitable temperature, to yield an amino-pyrimidine of Formula IV

(10)

For a compound of Formula I, the following definitions apply:

$R^1$ is phenyl, or a 5 to 6-membered heteroaryl ring; optionally substituted with up to three instances independently selected from the group consisting of halogen or methyl; wherein said 5 or 6-membered heteroaryl ring contains up to 3 ring atoms selected from the group consisting of N, S or O;

$R^2$ is phenyl or a 6-membered heteroaryl, optionally substituted with up to three instances of $R^5$; wherein said 6-membered heteroaryl ring contains up to 2 nitrogen ring atoms;

$R^4$ is chloro, —OMe or —$NR^6R^7$;

each $R^5$ is independently methyl, methoxy or halogen;

$R^6$ is hydrogen or $C_{1-4}$ alkyl substituted with 0 to 3 instances of $R^8$;

$R^7$ is hydrogen or $C_{1-4}$ alkyl substituted with 0 to 3 instances of $R^8$; and each $R^8$ is independently —OH, $C_{1-3}$ haloalkyl, halogen or —C(O)$NH_2$.

In some embodiments, for any one of the above eleven processes for the preparation of a compound of Formula II, Formula III or Formula IV, $R^1$ is phenyl. In other embodiments, $R^1$ is a 5 to 6-membered heteroaryl ring. In still other embodiments, $R^1$ is a 5-membered heteroaryl ring. In still other embodiments, $R^1$ is a 5-membered heteroaryl ring containing up to 2 ring heteroatoms selected from the group consisting of N and O. In still other embodiments, $R^1$ is a 5-membered heteroaryl ring containing up to 2 ring heteroatoms selected from the group consisting of N and O and it is unsubstituted.

In some embodiments, for any one of the above eleven processes for the preparation of a compound of Formula II, Formula III or Formula IV, $R^2$ is phenyl, optionally substituted with up to two instances of $R^5$. In other embodiments, $R^2$ is a 6-membered heteroaryl, optionally substituted with up to two instances of $R^5$; wherein said 6-membered heteroaryl ring contains up to 2 nitrogen ring atoms. In other embodiments, $R^2$ is phenyl, optionally substituted with up to one instance of $R^5$.

In some embodiments, for any one of the above eleven processes for the preparation of a compound of Formula II, Formula III or Formula IV, each $R^5$ is independently methyl or halogen. In other embodiments, each $R^5$ is independently halogen. In still other embodiments, each $R^5$ is fluoro.

In some embodiments, for any one of the above eleven processes for the preparation of a compound of Formula II, Formula III or Formula IV, $R^6$ is hydrogen or $C_{1-2}$ alkyl substituted with 0 to 3 instances of $R^8$. In other embodiments, $R^6$ is hydrogen. In still other embodiments, $R^6$ is $C_{1-2}$ alkyl substituted with 2 instances of $R^8$. In yet other embodiments, $R^6$ is $C_{1-2}$ alkyl substituted with 3 instances of $R^8$.

In some embodiments, for any one of the above eleven processes for the preparation of a compound of Formula II, Formula III or Formula IV, $R^7$ is hydrogen or $C_{1-2}$ alkyl substituted with 0 to 3 instances of $R^8$. In other embodiments, $R^7$ is hydrogen. In still other embodiments, $R^7$ is $C_{1-2}$ alkyl substituted with 2 instances of $R^8$. In yet other embodiments, $R^7$ is $C_{1-2}$ alkyl substituted with 3 instances of $R^8$.

In some embodiments, for any one of the above eleven processes for the preparation of a compound of Formula II, Formula III or Formula IV, each $R^8$ is independently —OH, trifluoromethyl, or —C(O)$NH_2$.

In some embodiments, for any one of the above eleven processes for the preparation of a compound of Formula II, Formula III or Formula IV, $R^1$ is a 5-membered heteroaryl ring containing up to 2 ring heteroatoms selected from the group consisting of N and O and it is unsubstituted; $R^2$ is phenyl, optionally substituted with one or two instances of $R^5$; each $R^5$ is fluoro; $R^6$ is hydrogen; $R^7$ is $C_{1-2}$ alkyl substituted with 3 instances of $R^8$ and each $R^8$ is independently —OH, trifluoromethyl, or —C(O)$NH_2$.

In a fourth embodiment, a compound of Formula I is a compound of Formula V. In a fifth embodiment, a compound of Formula I is a compound of Formula VI. In a sixth embodiment, a compound of Formula I is a compound of Formula VII.

A first process for making a compound of Formula V, a compound of Formula VI or a compound of Formula VII comprises the steps of:

i) coupling an appropriate amount of intermediate amide (1') with intermediate pyrimidine (2), in a suitable aprotic organic solvent, at a suitable temperature, in the presence of an appropriate amount of a suitable base, to afford, after quenching with acid, a solution of intermediate (3')

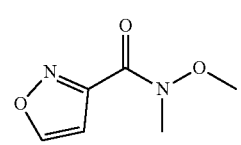

(1')

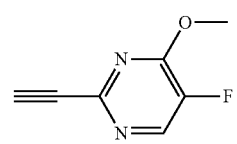

(2)

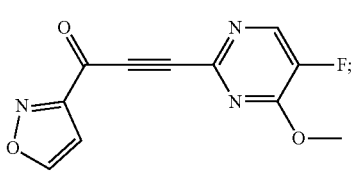
(3')

ii) at pH>5, optionally after addition of an appropriate amount of N,O-dimethylhydroxylamine or a salt (e.g., HCl salt) thereof, in a suitable solvent, at a suitable temperature, allowing the mixture to react to afford intermediate (4')

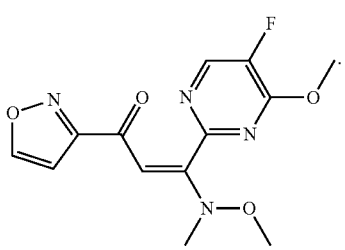
(4')

A second process for making a compound of Formula V, a compound of Formula VI or a compound of Formula VII, comprises the steps of:

i) coupling an appropriate amount of intermediate amide (1') with intermediate pyrimidine (2), in a suitable aprotic organic solvent, at a suitable temperature, in the presence of an appropriate amount of a suitable base, to afford, after quenching with acid, a solution of intermediate (3');

ii) at pH>5, optionally after addition of an appropriate amount of N,O-dimethylhydroxylamine or a salt (e.g. HCl salt) thereof, in a suitable solvent, at a suitable temperature, allowing the mixture to react to afford intermediate (4'); and iii) condensing intermediate (4') with an appropriate amount of a hydrazine of formula

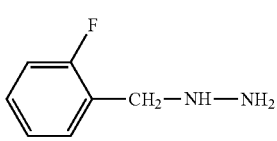

or a salt (e.g., HCl salt) thereof, optionally in the presence of an appropriate amount of a suitable base, in a suitable protic solvent, at a suitable temperature, affording a compound of Formula V.

A third process for making a compound of Formula V, a compound of Formula VI or a compound of Formula VII, comprises the steps of:

i) coupling an appropriate amount of intermediate amide (1') with intermediate pyrimidine (2), in a suitable aprotic organic solvent, at a suitable temperature, in the presence of an appropriate amount of a suitable base, to afford, after quenching with acid, a solution of intermediate (3');

ii) at pH>5, optionally after addition of an appropriate amount of N,O-dimethylhydroxylamine or a salt (e.g. HCl salt) thereof, in a suitable solvent, at a suitable temperature, allowing the mixture to react to afford intermediate (4');

iiia) condensing the compound of formula (4') with an appropriate amount of hydrazine, in a suitable protic or aprotic solvent, at a suitable temperature, affording a compound of formula (24'); and iiib) alkylating the compound of formula (24') with an appropriate amount of an alkylating agent of formula (23A), optionally in the presence of an appropriate amount of a suitable base, in a suitable protic or aprotic solvent, at a suitable temperature, affording the compound of Formula V.

A fourth process for making a compound of Formula V, a compound of Formula VI or a compound of Formula VII comprises the steps of:

a) reacting dibromopyrimidine (5) with an appropriate amount of a suitable base, in in methanol or a suitable methoxide salt in a suitable aprotic solvent, at a suitable temperature, to provide, after workup, a solution of a bromopyrimidine intermediate (6) in a suitable aprotic solvent

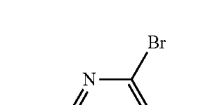
(5)

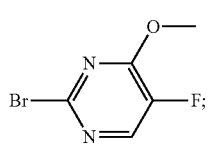
(6)

b) coupling bromopyrimidine intermediate (6) with an appropriate amount of ethynyltrimethylsilane, in a suitable aprotic organic solvent, at a suitable temperature, in the presence of an appropriate amount of a suitable base; in the presence of an appropriate amount of an optional suitable Cu(I) catalyst and an appropriate amount of a suitable Pd catalyst to afford, after workup, a solution of intermediate (7) in a suitable solvent

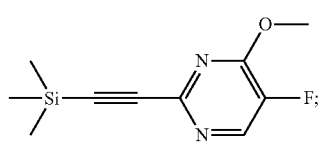
(7)

c) de-silylating intermediate (7) with an appropriate amount of a suitable fluoride reactant, a suitable acid or a suitable base, in a suitable solvent, at a suitable temperature, to provide pyrimidine intermediate (2);

i) coupling an appropriate amount of intermediate amide (1') with intermediate pyrimidine (2), in a suitable aprotic organic solvent, at a suitable temperature, in the presence of an appropriate amount of a suitable base, to afford, after quenching with an acid, a solution of intermediate (3');

ii) at pH>5, optionally after addition of an appropriate amount of N,O-dimethylhydroxylamine or a salt (e.g., HCl salt) thereof, in a suitable solvent, at a suitable temperature, allowing the mixture to react to afford intermediate (4'); and iii) condensing intermediate (4') with an appropriate amount of a hydrazine of formula

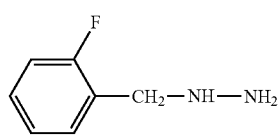

or a salt (e.g. HCl salt) thereof, optionally in the presence of an appropriate amount of a suitable base, in a suitable protic or aprotic solvent, at a suitable temperature, affording a compound of Formula V.

A fifth process for making a compound of Formula V, a compound of Formula VI or a compound of Formula VII comprises the steps of:

a) reacting dibromopyrimidine (5) with an appropriate amount of a suitable base, in in methanol or a suitable methoxide salt in a suitable aprotic solvent, at a suitable temperature, to provide, after workup, a solution of a bromopyrimidine intermediate (6) in a suitable aprotic solvent

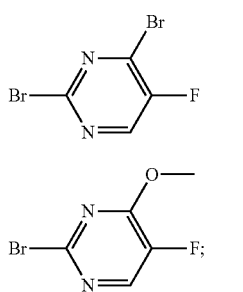

(5)

(6)

b) coupling bromopyrimidine intermediate (6) with an appropriate amount of ethynyltrimethylsilane, in a suitable aprotic organic solvent, at a suitable temperature, in the presence of an appropriate amount of a suitable base; in the presence of an appropriate amount of an optional suitable Cu(I) catalyst and an appropriate amount of a suitable Pd catalyst to afford, after workup, a solution of intermediate (7) in a suitable solvent

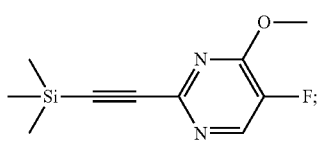

(7)

c) de-silylating intermediate (7) with an appropriate amount of a suitable fluoride reactant, a suitable acid or a suitable base, in a suitable solvent, at a suitable temperature, to provide pyrimidine intermediate (2);

i) coupling an appropriate amount of intermediate amide (1') with intermediate pyrimidine (2), in a suitable aprotic organic solvent, at a suitable temperature, in the presence of an appropriate amount of a suitable base, to afford, after quenching with an acid, a solution of intermediate (3');

ii) at pH>5, optionally after addition of an appropriate amount of N, O-dimethylhydroxylamine or a salt (e.g., HCl salt) thereof, in a suitable solvent, at a suitable temperature, allowing the mixture to react to afford intermediate (4'); and iiia) condensing the compound of formula (4') with an appropriate amount of hydrazine, in a suitable protic or aprotic solvent, at a suitable temperature, affording a compound of formula (24'); and iiib) alkylating the compound of formula (24') with an appropriate amount of an alkylating agent of formula (23A), optionally in the presence of an appropriate amount of a suitable base, in a suitable protic or aprotic solvent, at a suitable temperature, affording the compound of Formula V.

A sixth process for making a compound of Formula V, a compound of Formula VI or a compound of Formula VII comprises the steps of:

a) reacting dibromopyrimidine (5) with an appropriate amount of a suitable base, in in methanol or a suitable methoxide salt in a suitable aprotic solvent, at a suitable temperature, to provide, after workup, a solution of a bromopyrimidine intermediate (6) in a suitable aprotic solvent;

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst; to afford, after workup, a solution of intermediate (7) in a suitable solvent;

c) de-silylating intermediate (7) with an appropriate amount of a suitable fluoride reactant, a suitable acid or a suitable base, in a suitable solvent, at a suitable temperature, to provide pyrimidine intermediate (2);

d) amidating carboxylic acid (8') by reacting it with an appropriate amount of oxalyl chloride or an equivalent amide coupling reagent, in a suitable aprotic organic solvent, at a suitable temperature, in the presence of an appropriate amount of a suitable catalyst; followed by an appropriate amount of N,O-dimethylhydroxylamine or a salt (e.g. HCl salt) thereof, in the presence of an appropriate excess of a suitable base, at a suitable temperature, in a suitable solvent to afford amide (1')

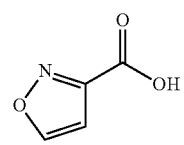

(8')

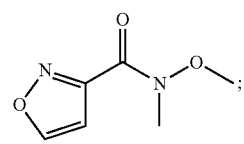

(1')

i) coupling an appropriate amount of intermediate amide (1') with intermediate pyrimidine (2), in a suitable aprotic organic solvent, at a suitable temperature, in the presence of an appropriate amount of a suitable base, to afford, after quenching with an acid, a solution of intermediate (3');

ii) at pH>5, optionally after addition of an appropriate amount of N,O-dimethylhydroxylamine or a salt (e.g., HCl salt) thereof, in a suitable solvent, at a suitable temperature, allowing the mixture to react to afford intermediate (4'); and iii) condensing intermediate (4') with an appropriate amount of a hydrazine of formula

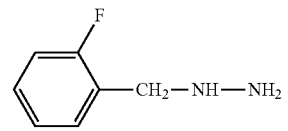

or a salt (e.g., HCl salt) thereof, optionally in the presence of an appropriate amount of a suitable base, in a suitable protic solvent, at a suitable temperature, affording a compound of Formula V.

A seventh process for making a compound of Formula V, a compound of Formula VI or a compound of Formula VII comprises the steps of:

a) reacting dibromopyrimidine (5) with an appropriate amount of a suitable base, in in methanol or a suitable methoxide salt in a suitable aprotic solvent, at a suitable temperature, to provide, after workup, a solution of a bromopyrimidine intermediate (6) in a suitable aprotic solvent;

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst; to afford, after workup, a solution of intermediate (7) in a suitable solvent;

c) de-silylating intermediate (7) with an appropriate amount of a suitable fluoride reactant, a suitable acid or a suitable base, in a suitable solvent, at a suitable temperature, to provide pyrimidine intermediate (2);

d) amidating carboxylic acid (8') by reacting it with an appropriate amount of oxalyl chloride or an equivalent amide coupling reagent, in a suitable aprotic organic solvent, at a suitable temperature, in the presence of an appropriate amount of a suitable catalyst; followed by an appropriate amount of N,O-dimethylhydroxylamine or a salt (e.g. HCl salt) thereof, in the presence of an appropriate excess of a suitable base, at a suitable temperature, in a suitable solvent to afford amide (1')

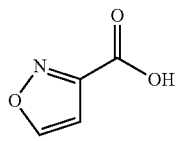

(8')

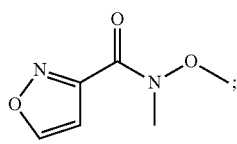

(1')

i) coupling an appropriate amount of intermediate amide (1') with intermediate pyrimidine (2), in a suitable aprotic organic solvent, at a suitable temperature, in the presence of an appropriate amount of a suitable base, to afford, after quenching with an acid, a solution of intermediate (3');

ii) at pH>5, optionally after addition of an appropriate amount of N,O-dimethylhydroxylamine or a salt (e.g., HCl salt) thereof, in a suitable solvent, at a suitable temperature, allowing the mixture to react to afford intermediate (4');

iiia) condensing the compound of formula (4') with an appropriate amount of hydrazine, in a suitable protic or aprotic solvent, at a suitable temperature, affording a compound of formula (24'); and iiib) alkylating the compound of formula (24') with an appropriate amount of an alkylating agent of formula (23A), optionally in the presence of an appropriate amount of a suitable base, in a suitable protic or aprotic solvent, at a suitable temperature, affording the compound of Formula V.

An eighth process for making a compound of Formula VI, or a compound of Formula VII comprises the steps of:

a) reacting dibromopyrimidine (5) with an appropriate amount of a suitable base, in in methanol or a suitable methoxide salt in a suitable aprotic solvent, at a suitable temperature, to provide, after workup, a solution of a bromopyrimidine intermediate (6) in a suitable aprotic solvent;

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst; to afford after workup, a solution of intermediate (7) in a suitable solvent;

c) de-silylating intermediate (7) with an appropriate amount of a suitable fluoride reactant, a suitable acid or a suitable base, in a suitable solvent, at a suitable temperature, to provide pyrimidine intermediate (2);

d) amidating carboxylic acid (8') by reacting it with an appropriate amount of oxalyl chloride or an equivalent amide coupling reagent, in a suitable aprotic organic solvent, at a suitable temperature, in the presence of an appropriate amount of a suitable catalyst; followed by an appropriate amount of N,O-dimethylhydroxylamine or salt (e.g. HCl salt) thereof, in the presence of an appropriate excess of a suitable base, at a suitable temperature, in a suitable solvent to afford amide (1');

i) coupling an appropriate amount of intermediate amide (1') with intermediate pyrimidine (2), in a suitable aprotic organic solvent, at a suitable temperature, in the presence of an appropriate amount of a suitable base, to afford, after quenching with acid, a solution of intermediate (3');

ii) at pH>5, optionally after addition of an appropriate amount of N,O-dimethylhydroxylamine or a salt (e.g., HCl salt) thereof, in a suitable solvent, at a suitable temperature, allowing the mixture to react to afford intermediate (4');

iii) condensing intermediate (4') with an appropriate amount of a hydrazine of formula

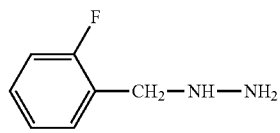

or a salt (e.g., HCl salt) thereof, optionally in the presence of an appropriate amount of a suitable base, in a suitable protic or aprotic solvent, at a suitable temperature, affording a compound of Formula V;

iv) de-methylating the compound of Formula V by reacting it with an appropriate amount of a de-methylating reagent, in a suitable solvent, at a suitable temperature, to afford alcohol (9')

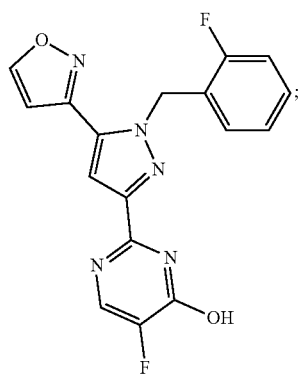

(9')

and v) chlorinating alcohol (9') with an appropriate amount of phosphoryl chloride and, optionally, an appropriate amount of a suitable base, at a suitable temperature, optionally in a suitable aprotic organic solvent to afford the chloropyrimidine of Formula VI.

A ninth process for making a compound of Formula VI, or a compound of Formula VII comprises the steps of:

a) reacting dibromopyrimidine (5) with an appropriate amount of a suitable base, in in methanol or a suitable methoxide salt in a suitable aprotic solvent, at a suitable temperature, to provide, after workup, a solution of a bromopyrimidine intermediate (6) in a suitable aprotic solvent;

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst; to afford after workup, a solution of intermediate (7) in a suitable solvent;

c) de-silylating intermediate (7) with an appropriate amount of a suitable fluoride reactant, a suitable acid or a suitable base, in a suitable solvent, at a suitable temperature, to provide pyrimidine intermediate (2);

d) amidating carboxylic acid (8') by reacting it with an appropriate amount of oxalyl chloride or an equivalent amide coupling reagent, in a suitable aprotic organic solvent, at a suitable temperature, in the presence of an appropriate amount of a suitable catalyst; followed by an appropriate amount of N,O-dimethylhydroxylamine or salt (e.g. HCl salt) thereof, in the presence of an appropriate excess of a suitable base, at a suitable temperature, in a suitable solvent to afford amide (1');

i) coupling an appropriate amount of intermediate amide (1') with intermediate pyrimidine (2), in a suitable aprotic organic solvent, at a suitable temperature, in the presence of an appropriate amount of a suitable base, to afford, after quenching with acid, a solution of intermediate (3');

ii) at pH>5, optionally after addition of an appropriate amount of N, O-dimethylhydroxylamine or a salt (e.g., HCl salt) thereof, in a suitable solvent, at a suitable temperature, allowing the mixture to react to afford intermediate (4');

iiia) condensing the compound of formula (4') with an appropriate amount of hydrazine, in a suitable protic or aprotic solvent, at a suitable temperature, affording a compound of formula (24');

iiib) alkylating the compound of formula (24') with an appropriate amount of an alkylating agent of formula (23A), optionally in the presence of an appropriate amount of a suitable base, in a suitable protic or aprotic solvent, at a suitable temperature, affording the compound of Formula V;

iv) de-methylating the compound of Formula V by reacting it with an appropriate amount of a de-methylating reagent, in a suitable solvent, at a suitable temperature, to afford alcohol (9')

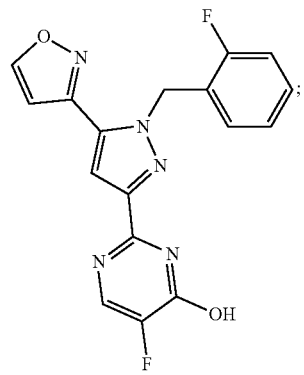

(9'A)

and v) chlorinating alcohol (9') with an appropriate amount of phosphoryl chloride and, optionally, an appropriate amount of a suitable base, at a suitable temperature, optionally in a suitable aprotic organic solvent to afford the chloropyrimidine of Formula VI.

A tenth process for making a compound of Formula VII, comprises the steps of:

a) reacting dibromopyrimidine (5) with an appropriate amount of a suitable base, in in methanol or a suitable methoxide salt in a suitable aprotic solvent, at a suitable temperature, to provide, after workup, a solution of a bromopyrimidine intermediate (6) in a suitable aprotic solvent;

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst to afford, after workup, a solution of intermediate (7) in a suitable solvent;

c) de-silylating intermediate (7) with an appropriate amount of a suitable fluoride reactant, a suitable acid or a suitable base, in a suitable solvent, at a suitable temperature, to provide pyrimidine intermediate (2);

d) amidating carboxylic acid (8') by reacting it with an appropriate amount of oxalyl chloride or an equivalent amide coupling reagent, in a suitable aprotic organic solvent, at a suitable temperature, in the presence of an appropriate amount of a suitable catalyst; followed by an appropriate amount of N,O-dimethylhydroxylamine or salt (e.g. HCl salt) thereof, in the presence of an appropriate excess of a suitable base, at a suitable temperature, in a suitable solvent to afford amide (1');

i) coupling an appropriate amount of intermediate amide (1') with intermediate pyrimidine (2), in a suitable aprotic organic solvent, at a suitable temperature, in the presence of an appropriate amount of a suitable base, to afford, after quenching with acid, a solution of intermediate (3');

ii) at pH>5, optionally after addition of an appropriate amount of N,O-dimethylhydroxylamine or a salt (e.g., HCl salt) thereof, in a suitable solvent, at a suitable temperature, allowing the mixture to react to afford intermediate (4');

iii) condensing intermediate (4') with an appropriate amount of a hydrazine of formula

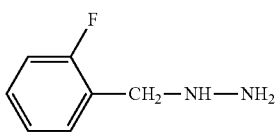

or a salt (e.g. HCl salt) thereof, optionally in the presence of an appropriate amount of a suitable base, in a suitable protic or aprotic solvent, at a suitable temperature, affording a compound of Formula V;

iv) de-methylating the compound of Formula V by reacting it with an appropriate amount of a de-methylating reagent, in a suitable solvent, at a suitable temperature, to afford alcohol (9');

v) chlorinating alcohol (9') with an appropriate amount of phosphoryl chloride and, optionally, an appropriate amount of a suitable base, at a suitable temperature, optionally in a suitable aprotic organic solvent to afford the chloropyrimidine of Formula VI; and vi) reacting an appropriate amount of an amine (10) with the chloropyrimidine of Formula VI, optionally in the presence of an appropriate amount of a suitable base, in a suitable solvent, at a suitable temperature, to yield an amino-pyrimidine of Formula VII.

An eleventh process for making a compound of Formula VII, comprises the steps of:

a) reacting dibromopyrimidine (5) with an appropriate amount of a suitable base, in in methanol or a suitable methoxide salt in a suitable aprotic solvent, at a suitable temperature, to provide, after workup, a solution of a bromopyrimidine intermediate (6) in a suitable aprotic solvent;

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst to afford, after workup, a solution of intermediate (7) in a suitable solvent;

c) de-silylating intermediate (7) with an appropriate amount of a suitable fluoride reactant, a suitable acid or a suitable base, in a suitable solvent, at a suitable temperature, to provide pyrimidine intermediate (2);

d) amidating carboxylic acid (8') by reacting it with an appropriate amount of oxalyl chloride or an equivalent amide coupling reagent, in a suitable aprotic organic solvent, at a suitable temperature, in the presence of an appropriate amount of a suitable catalyst; followed by an appropriate amount of N,O-dimethylhydroxylamine or salt (e.g. HCl salt) thereof, in the presence of an appropriate excess of a suitable base, at a suitable temperature, in a suitable solvent to afford amide (1');

i) coupling an appropriate amount of intermediate amide (1') with intermediate pyrimidine (2), in a suitable aprotic organic solvent, at a suitable temperature, in the presence of an appropriate amount of a suitable base, to afford, after quenching with acid, a solution of intermediate (3');

ii) at pH>5, optionally after addition of an appropriate amount of N, O-dimethylhydroxylamine or a salt (e.g., HCl salt) thereof, in a suitable solvent, at a suitable temperature, allowing the mixture to react to afford intermediate (4');

iiia) condensing the compound of formula (4') with an appropriate amount of hydrazine, in a suitable protic or aprotic solvent, at a suitable temperature, affording a compound of formula (24'); and iiib) alkylating the compound of formula (24') with an appropriate amount of an alkylating agent of formula (23A), optionally in the presence of an appropriate amount of a suitable base, in a suitable protic or aprotic solvent, at a suitable temperature, affording the compound of Formula V;

iv) de-methylating the compound of Formula V by reacting it with an appropriate amount of a de-methylating reagent, in a suitable solvent, at a suitable temperature, to afford alcohol (9');

v) chlorinating alcohol (9') with an appropriate amount of phosphoryl chloride and, optionally, an appropriate amount of a suitable base, at a suitable temperature, optionally in a suitable aprotic organic solvent to afford the chloropyrimidine of Formula VI; and vi) reacting an appropriate amount of an amine (10) with the chloropyrimidine of Formula VI, optionally in the presence of an appropriate amount of a suitable base, in a suitable solvent, at a suitable temperature, to yield an amino-pyrimidine of Formula VII.

In some embodiments, for any one of the above eleven processes for the preparation of a compound of Formula V, Formula VI or Formula VII, $R^6$ is hydrogen or $C_{1-2}$ alkyl substituted with 0 to 3 instances of $R^8$. In other embodiments, $R^6$ is hydrogen. In still other embodiments, $R^6$ is $C_{1-2}$ alkyl substituted with 2 instances of $R^8$. In yet other embodiments, $R^6$ is $C_{1-2}$ alkyl substituted with 3 instances of $R^8$.

In some embodiments, for any one of the above eleven processes for the preparation of a compound of Formula V, Formula VI or Formula VII, $R^7$ is hydrogen or $C_{1-2}$ alkyl substituted with 0 to 3 instances of $R^8$. In other embodiments, $R^7$ is hydrogen. In still other embodiments, $R^7$ is $C_{1-2}$ alkyl substituted with 2 instances of $R^8$. In yet other embodiments, $R^7$ is $C_{1-2}$ alkyl substituted with 3 instances of $R^8$.

In some embodiments, for any one of the above eleven processes for the preparation of a compound of Formula V, Formula VI or Formula VII, each $R^8$ is independently —OH, trifluoromethyl, or —C(O)NH$_2$.

In some embodiments, for any one of the above eleven processes for the preparation of a compound of Formula V, Formula VI or Formula VII, $R^6$ is hydrogen; $R^7$ is $C_{1-2}$ alkyl substituted with 3 instances of $R^8$ and each $R^8$ is independently —OH, trifluoromethyl, or —C(O)NH$_2$.

In a seventh embodiment, a compound of Formula I is the compound of Formula IA. In an eighth embodiment, a compound of Formula I is Formula IB. In a ninth embodiment, a compound of Formula I is a compound of Formula IC. In a tenth embodiment, a compound of Formula I is a compound of Formula ID.

A first process for making a compound of Formula IA, Formula IB, Formula IC or Formula ID comprises the steps of:

i) coupling an appropriate amount of intermediate amide (1') with intermediate pyrimidine (2), in a suitable aprotic organic solvent, at a suitable temperature, in the presence of an appropriate amount of a suitable base, to afford, after quenching with an acid, a solution of intermediate (3'); and ii) at pH>5, optionally after addition of an appropriate amount of N,O-dimethylhydroxylamine or a salt (e.g., HCl salt) thereof, in a suitable solvent, at a suitable temperature, allowing the mixture to react to afford intermediate (4').

A second process for making a compound of Formula IA, Formula IB, Formula IC or Formula ID, comprises the steps of:

i) coupling an appropriate amount of intermediate amide (1') with intermediate pyrimidine (2), in a suitable aprotic organic solvent, at a suitable temperature, in the presence of an appropriate amount of a suitable base, to afford, after quenching with an acid, a solution of intermediate (3');

ii) at pH>5, optionally after addition of an appropriate amount of N,O-dimethylhydroxylamine or a salt (e.g., HCl salt) thereof, in a suitable solvent, at a suitable temperature, allowing the mixture to react to afford intermediate (4'); and iii) condensing intermediate (4') with an appropriate amount of a hydrazine of formula

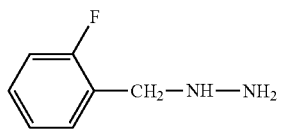

or a salt (e.g., HCl salt) thereof, optionally in the presence of an appropriate amount of a suitable base, in a suitable protic solvent, at a suitable temperature, affording a compound of Formula V.

A third process for making a compound of Formula IA, Formula IB, Formula IC or Formula ID, comprises the steps of:

i) coupling an appropriate amount of intermediate amide (1') with intermediate pyrimidine (2), in a suitable aprotic organic solvent, at a suitable temperature, in the presence of an appropriate amount of a suitable base, to afford, after quenching with an acid, a solution of intermediate (3');

ii) at pH>5, optionally after addition of an appropriate amount of N,O-dimethylhydroxylamine or a salt (e.g., HCl salt) thereof, in a suitable solvent, at a suitable temperature, allowing the mixture to react to afford intermediate (4');

iiia) condensing the compound of formula (4') with an appropriate amount of hydrazine, in a suitable protic or aprotic solvent, at a suitable temperature, affording a compound of formula (24'); and iiib) alkylating the compound of formula (24') with an appropriate amount of an alkylating agent of formula (23A), optionally in the presence of an appropriate amount of a suitable base, in a suitable protic or aprotic solvent, at a suitable temperature, affording the compound of Formula V.

A fourth process for making a compound of Formula IA, Formula IB, Formula IC or Formula ID, comprises the steps of:

a) reacting dibromopyrimidine (5) with an appropriate amount of a suitable base, in in methanol or a suitable methoxide salt in a suitable aprotic solvent, at a suitable temperature, to provide, after workup, a solution of a bromopyrimidine intermediate (6) in a suitable aprotic solvent;

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst to afford after workup, a solution of intermediate (7) in a suitable solvent;

c) de-silylating intermediate (7) with an appropriate amount of a suitable fluoride reactant, a suitable acid or a suitable base, in a suitable solvent, at a suitable temperature, to provide pyrimidine intermediate (2);

i) coupling an appropriate amount of intermediate amide (1') with intermediate pyrimidine (2), in a suitable aprotic organic solvent, at a suitable temperature, in the presence of an appropriate amount of a suitable base, to afford, after quenching with an acid, a solution of intermediate (3');

ii) at pH>5, optionally after addition of an appropriate amount of N,O-dimethylhydroxylamine or a salt (e.g., HCl salt) thereof, in a suitable solvent, at a suitable temperature, allowing the mixture to react to afford intermediate (4'); and iii) condensing intermediate (4') with an appropriate amount of a hydrazine of formula

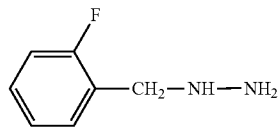

or a salt (e.g., HCl salt) thereof, optionally in the presence of an appropriate amount of a suitable base, in a suitable protic or aprotic solvent, at a suitable temperature, affording a compound of Formula V.

A fifth process for making a compound of Formula IA, Formula IB, Formula IC or Formula ID, comprises the steps of:

a) reacting dibromopyrimidine (5) with an appropriate amount of a suitable base, in in methanol or a suitable methoxide salt in a suitable aprotic solvent, at a suitable temperature, to provide, after workup, a solution of a bromopyrimidine intermediate (6) in a suitable aprotic solvent;

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst to afford after workup, a solution of intermediate (7) in a suitable solvent;

c) de-silylating intermediate (7) with an appropriate amount of a suitable fluoride reactant, a suitable acid or a suitable base, in a suitable solvent, at a suitable temperature, to provide pyrimidine intermediate (2);

i) coupling an appropriate amount of intermediate amide (1') with intermediate pyrimidine (2), in a suitable aprotic organic solvent, at a suitable temperature, in the presence of an appropriate amount of a suitable base, to afford, after quenching with an acid, a solution of intermediate (3');

ii) at pH>5, optionally after addition of an appropriate amount of N,O-dimethylhydroxylamine or a salt (e.g., HCl salt) thereof, in a suitable solvent, at a suitable temperature, allowing the mixture to react to afford intermediate (4'); and iiia) condensing the compound of formula (4') with an appropriate amount of hydrazine, in a suitable protic or aprotic solvent, at a suitable temperature, affording a compound of formula (24'); and iiib) alkylating the compound of formula (24') with an appropriate amount of an alkylating agent of formula (23A), optionally in the presence of an appropriate amount of a suitable base, in a suitable protic or aprotic solvent, at a suitable temperature, affording the compound of Formula V.

A sixth process for making a compound a compound of Formula IA, Formula IB, Formula IC or Formula ID, comprises the steps of:

a) reacting dibromopyrimidine (5) with an appropriate amount of a suitable base, in in methanol or a suitable methoxide salt in a suitable aprotic solvent, at a suitable temperature, to provide, after workup, a solution of a bromopyrimidine intermediate (6) in a suitable aprotic solvent;

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst to afford after workup, a solution of intermediate (7) in a suitable solvent;

c) de-silylating intermediate (7) with an appropriate amount of a suitable fluoride reactant, a suitable acid or a suitable base, in a suitable solvent, at a suitable temperature, to provide pyrimidine intermediate (2);

d) amidating carboxylic acid (8') by reacting it with an appropriate amount of oxalyl chloride or an equivalent amide coupling reagent, in a suitable aprotic organic solvent, at a suitable temperature, in the presence of an appropriate amount of a suitable catalyst; followed by an appropriate amount of N,O-dimethylhydroxylamine or salt (e.g. HCl salt) thereof, in the presence of an appropriate excess of a suitable base, at a suitable temperature, in a suitable solvent to afford amide (1');

i) coupling an appropriate amount of the intermediate amide (1') with intermediate pyrimidine (2), in a suitable aprotic organic solvent, at a suitable temperature, in the presence of an appropriate amount of a suitable base, to afford, after quenching with an acid, a solution of intermediate (3');

ii) at pH>5, optionally after addition of an appropriate amount of N,O-dimethylhydroxylamine or a salt (e.g., HCl salt) thereof, in a suitable solvent, at a suitable temperature, allowing the mixture to react to afford intermediate (4'); and iii) condensing intermediate (4') with an appropriate amount of a hydrazine of formula

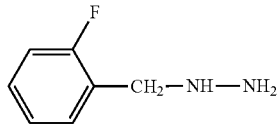

or a salt (e.g., HCl salt) thereof, optionally in the presence of an appropriate amount of a suitable base, in a suitable protic solvent, at a suitable temperature, affording a compound of Formula V.

A seventh process for making a compound a compound of Formula IA, Formula IB, Formula IC or Formula ID, comprises the steps of:

a) reacting dibromopyrimidine (5) with an appropriate amount of a suitable base, in in methanol or a suitable methoxide salt in a suitable aprotic solvent, at a suitable temperature, to provide, after workup, a solution of a bromopyrimidine intermediate (6) in a suitable aprotic solvent;

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst to afford after workup, a solution of intermediate (7) in a suitable solvent;

c) de-silylating intermediate (7) with an appropriate amount of a suitable fluoride reactant, a suitable acid or a suitable base, in a suitable solvent, at a suitable temperature, to provide pyrimidine intermediate (2);

d) amidating carboxylic acid (8') by reacting it with an appropriate amount of oxalyl chloride or an equivalent amide coupling reagent, in a suitable aprotic organic solvent, at a suitable temperature, in the presence of an appropriate amount of a suitable catalyst; followed by an appropriate amount of N,O-dimethylhydroxylamine or salt (e.g. HCl salt) thereof, in the presence of an appropriate excess of a suitable base, at a suitable temperature, in a suitable solvent to afford amide (1');

i) coupling an appropriate amount of the intermediate amide (1') with intermediate pyrimidine (2), in a suitable aprotic organic solvent, at a suitable temperature, in the presence of an appropriate amount of a suitable base, to afford, after quenching with an acid, a solution of intermediate (3');

ii) at pH>5, optionally after addition of an appropriate amount of N, O-dimethylhydroxylamine or a salt (e.g., HCl salt) thereof, in a suitable solvent, at a suitable temperature, allowing the mixture to react to afford intermediate (4');

iiia) condensing the compound of formula (4') with an appropriate amount of hydrazine, in a suitable protic or aprotic solvent, at a suitable temperature, affording a compound of formula (24'); and iiib) alkylating the compound of formula (24') with an appropriate amount of an alkylating agent of formula (23A), optionally in the presence of an appropriate amount of a suitable base, in a suitable protic or aprotic solvent, at a suitable temperature, affording the compound of Formula V.

An eighth process for making a compound of Formula IA, Formula IB, Formula IC or Formula ID, comprises the steps of:

a) reacting dibromopyrimidine (5) with an appropriate amount of a suitable base, in in methanol or a suitable methoxide salt in a suitable aprotic solvent, at a suitable temperature, to provide, after workup, a solution of a bromopyrimidine intermediate (6) in a suitable aprotic solvent;

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst to afford after workup, a solution of intermediate (7) in a suitable solvent;

c) de-silylating intermediate (7) with an appropriate amount of a suitable fluoride reactant, a suitable acid or a suitable base, in a suitable solvent, at a suitable temperature, to provide pyrimidine intermediate (2);

d) amidating carboxylic acid (8') by reacting it with an appropriate amount of oxalyl chloride or an equivalent amide coupling reagent, in a suitable aprotic organic solvent, at a suitable temperature, in the presence of an appropriate amount of a suitable catalyst; followed by an appropriate amount of N,O-dimethylhydroxylamine or salt (e.g. HCl salt) thereof, in the presence of an appropriate excess of a suitable base, at a suitable temperature, in a suitable solvent to afford amide (1');

i) coupling an appropriate amount of intermediate amide (1') with intermediate pyrimidine (2), in a suitable aprotic organic solvent, at a suitable temperature, in the presence of an appropriate amount of a suitable base, to afford, after quenching with an acid, a solution of intermediate (3');

ii) at pH>5, optionally after addition of an appropriate amount of N,O-dimethylhydroxylamine or a salt (e.g., HCl salt) thereof, in a suitable solvent, at a suitable temperature, allowing the mixture to react to afford intermediate (4');

iii) condensing intermediate (4') with an appropriate amount of a hydrazine of formula

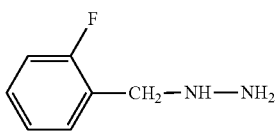

or salt (e.g., HCl salt) thereof, optionally in the presence of an appropriate amount of a suitable base, in a suitable protic or aprotic solvent, at a suitable temperature, affording a compound of Formula V;

iv) de-methylating the compound of Formula V by reacting it with an appropriate amount of a de-methylating reagent, in a suitable solvent, at a suitable temperature, to afford alcohol (9'); and v) chlorinating alcohol (9') with an appropriate amount of phosphoryl chloride and, optionally, an appropriate amount of a suitable base, at a suitable temperature, optionally in a suitable aprotic organic solvent to afford the chloropyrimidine of Formula VI.

A ninth process for making a compound of Formula IA, Formula IB, Formula IC or Formula ID, comprises the steps of:

a) reacting dibromopyrimidine (5) with an appropriate amount of a suitable base, in in methanol or a suitable methoxide salt in a suitable aprotic solvent, at a suitable temperature, to provide, after workup, a solution of a bromopyrimidine intermediate (6) in a suitable aprotic solvent;

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst to afford after workup, a solution of intermediate (7) in a suitable solvent;

c) de-silylating intermediate (7) with an appropriate amount of a suitable fluoride reactant, a suitable acid or a suitable base, in a suitable solvent, at a suitable temperature, to provide pyrimidine intermediate (2);

d) amidating carboxylic acid (8') by reacting it with an appropriate amount of oxalyl chloride or an equivalent amide coupling reagent, in a suitable aprotic organic solvent, at a suitable temperature, in the presence of an appropriate amount of a suitable catalyst; followed by an appropriate amount of N,O-dimethylhydroxylamine or salt (e.g. HCl salt) thereof, in the presence of an appropriate excess of a suitable base, at a suitable temperature, in a suitable solvent to afford amide (1');

i) coupling an appropriate amount of intermediate amide (1') with intermediate pyrimidine (2), in a suitable aprotic organic solvent, at a suitable temperature, in the presence of an appropriate amount of a suitable base, to afford, after quenching with an acid, a solution of intermediate (3');

ii) at pH>5, optionally after addition of an appropriate amount of N,O-dimethylhydroxylamine or a salt (e.g., HCl salt) thereof, in a suitable solvent, at a suitable temperature, allowing the mixture to react to afford intermediate (4');

iiia) condensing the compound of formula (4') with an appropriate amount of hydrazine, in a suitable protic or aprotic solvent, at a suitable temperature, affording a compound of formula (24');

iiib) alkylating the compound of formula (24') with an appropriate amount of an alkylating agent of formula (23A), optionally in the presence of an appropriate amount of a suitable base, in a suitable protic or aprotic solvent, at a suitable temperature, affording the compound of Formula V;

iv) de-methylating the compound of Formula V by reacting it with an appropriate amount of a de-methylating reagent, in a suitable solvent, at a suitable temperature, to afford alcohol (9'); and v) chlorinating alcohol (9') with an appropriate amount of phosphoryl chloride and, optionally, an appropriate amount of a suitable base, at a suitable temperature, optionally in a suitable aprotic organic solvent to afford the chloropyrimidine of Formula VI A tenth process for making a compound of Formula IA, comprises the steps of:

a) reacting dibromopyrimidine (5) with an appropriate amount of a suitable base, in in methanol or a suitable methoxide salt in a suitable aprotic solvent, at a suitable temperature, to provide, after workup, a solution of a bromopyrimidine intermediate (6) in a suitable aprotic solvent;

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst to afford after workup, a solution of intermediate (7) in a suitable solvent;

c) de-silylating intermediate (7) with an appropriate amount of a suitable fluoride reactant, a suitable acid or a suitable base, in a suitable solvent, at a suitable temperature, to provide pyrimidine intermediate (2);

d) amidating carboxylic acid (8') by reacting it with an appropriate amount of oxalyl chloride or an equivalent amide coupling reagent, in a suitable aprotic organic solvent, at a suitable temperature, in the presence of an appropriate amount of a suitable catalyst; followed by an appropriate amount of N,O-dimethylhydroxylamine or salt (e.g. HCl salt) thereof, in the presence of an appropriate excess of a suitable base, at a suitable temperature, in a suitable solvent to afford amide (1');

i) coupling an appropriate amount of intermediate amide (1') with intermediate pyrimidine (2), in a suitable aprotic organic solvent, at a suitable temperature, in the presence of an appropriate amount of a suitable base, to afford, after quenching with an acid, a solution of intermediate (3');

ii) at pH>5, optionally after addition of an appropriate amount of N, O-dimethylhydroxylamine or a salt (e.g., HCl salt) thereof, in a suitable solvent, at a suitable temperature, allowing the mixture to react to afford intermediate (4');

iii) condensing intermediate (4') with an appropriate amount of a hydrazine of formula

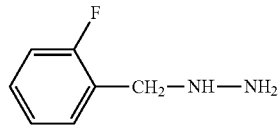

or a salt (e.g., HCl salt) thereof, optionally in the presence of an appropriate amount of a suitable base, in a suitable protic solvent, at a suitable temperature, affording a compound of Formula V;

iv) de-methylating the compound of Formula V by reacting it with an appropriate amount of a de-methylating reagent, in a suitable solvent, at a suitable temperature, to afford alcohol (9');

v) chlorinating alcohol (9') with an appropriate amount of phosphoryl chloride and, optionally, an appropriate amount of a suitable base, at a suitable temperature, optionally in a suitable aprotic organic solvent to afford the chloropyrimidine of Formula VI; and vi) reacting an appropriate amount of an amine (17) with the chloropyrimidine of Formula VI, optionally in the presence of an appropriate amount of a suitable base, in a suitable solvent, at a suitable temperature, to yield the compound of Formula IA

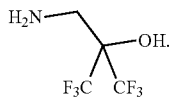
(17)

An eleventh process for making a compound of Formula IA, comprises the steps of:

a) reacting dibromopyrimidine (5) with an appropriate amount of a suitable base, in in methanol or a suitable methoxide salt in a suitable aprotic solvent, at a suitable temperature, to provide, after workup, a solution of a bromopyrimidine intermediate (6) in a suitable aprotic solvent;

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst to afford after workup, a solution of intermediate (7) in a suitable solvent;

c) de-silylating intermediate (7) with an appropriate amount of a suitable fluoride reactant, a suitable acid or a suitable base, in a suitable solvent, at a suitable temperature, to provide pyrimidine intermediate (2);

d) amidating carboxylic acid (8') by reacting it with an appropriate amount of oxalyl chloride or an equivalent amide coupling reagent, in a suitable aprotic organic solvent, at a suitable temperature, in the presence of an appropriate amount of a suitable catalyst; followed by an appropriate amount of N,O-dimethylhydroxylamine or salt (e.g. HCl salt) thereof, in the presence of an appropriate excess of a suitable base, at a suitable temperature, in a suitable solvent to afford amide (1');

i) coupling an appropriate amount of intermediate amide (1') with intermediate pyrimidine (2), in a suitable aprotic organic solvent, at a suitable temperature, in the presence of an appropriate amount of a suitable base, to afford, after quenching with an acid, a solution of intermediate (3');

ii) at pH>5, optionally after addition of an appropriate amount of N, O-dimethylhydroxylamine or a salt (e.g., HCl salt) thereof, in a suitable solvent, at a suitable temperature, allowing the mixture to react to afford intermediate (4');

iiia) condensing the compound of formula (4') with an appropriate amount of hydrazine, in a suitable protic or aprotic solvent, at a suitable temperature, affording a compound of formula (24');

iiib) alkylating the compound of formula (24') with an appropriate amount of an alkylating agent of formula (23A), optionally in the presence of an appropriate amount of a suitable base, in a suitable protic or aprotic solvent, at a suitable temperature, affording the compound of Formula V;

iv) de-methylating the compound of Formula V by reacting it with an appropriate amount of a de-methylating reagent, in a suitable solvent, at a suitable temperature, to afford alcohol (9');

v) chlorinating alcohol (9') with an appropriate amount of phosphoryl chloride and, optionally, an appropriate amount of a suitable base, at a suitable temperature, optionally in a suitable aprotic organic solvent to afford the chloropyrimidine of Formula VI; and vi) reacting an appropriate amount of an amine (17)

with the chloropyrimidine of Formula VI, optionally in the presence of an appropriate amount of a suitable base, in a suitable solvent, at a suitable temperature, to yield the compound of Formula IA.

In some embodiments of the above eleven processes for making the compound of Formula IA, the compound of Formula IA can be further purified. The preparation of purer compound of Formula IA involves the additional step of:

A') dissolving the compound of Formula IA obtained in step vi) in an appropriate amount of MeOH and stirring the resulting mixture at a temperature between 30° C. and 65° C. until all solids dissolve to obtain a methanol solution of Formula IA;

B') filtering the resulting methanol solution of the compound of Formula IA;

C') adding water while maintaining temperature between 50° C. and 60° C. to yield a slurry;

D') cooling the resulting slurry of the compound of Formula IA; and

E') filtering and drying the resulting re-crystallized compound of Formula IA.

A tenth process for making the compound of Formula IB, comprises the steps of:

a) reacting dibromopyrimidine (5) with an appropriate amount of a suitable base, in methanol or a suitable methoxide salt in a suitable aprotic solvent, at a suitable temperature, to provide, after workup, a solution of a bromopyrimidine intermediate (6) in a suitable aprotic solvent;

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst to afford after workup, a solution of intermediate (7) in a suitable solvent;

c) de-silylating intermediate (7) with an appropriate amount of a suitable fluoride reactant, a suitable acid or a suitable base, in a suitable solvent, at a suitable temperature, to provide pyrimidine intermediate (2);

d) amidating carboxylic acid (8') by reacting it with an appropriate amount of oxalyl chloride or an equivalent amide coupling reagent, in a suitable aprotic organic solvent, at a suitable temperature, in the presence of an appropriate amount of a suitable catalyst; followed by an appropriate amount of N,O-dimethylhydroxylamine or salt (e.g. HCl salt) thereof, in the presence of an appropriate excess of a suitable base, at a suitable temperature, in a suitable solvent to afford amide (1');

i) coupling an appropriate amount of intermediate amide (1') with intermediate pyrimidine (2), in a suitable aprotic organic solvent, at a suitable temperature, in the presence of an appropriate amount of a suitable base, to afford, after quenching with an acid, a solution of intermediate (3');

ii) at pH>5, optionally after addition of an appropriate amount of N, O-dimethylhydroxylamine or a salt (e.g. HCl salt) thereof, in a suitable solvent, at a suitable temperature, allowing the mixture to react to afford intermediate (4');

iii) condensing intermediate (4') with an appropriate amount of a hydrazine of formula

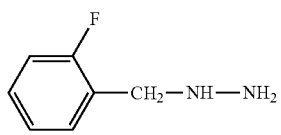

or a salt (e.g., HCl salt) thereof, optionally in the presence of an appropriate amount of a suitable base, in a suitable protic or aprotic solvent, at a suitable temperature, affording a compound of Formula V;

iv) de-methylating the compound of Formula V by reacting it with an appropriate amount of a de-methylating reagent, in a suitable solvent, at a suitable temperature, to afford alcohol (9');

v) chlorinating alcohol (9') with an appropriate amount of phosphoryl chloride and, optionally, an appropriate amount of a suitable base, at a suitable temperature, optionally in a suitable aprotic organic solvent to afford the chloropyrimidine of Formula VI; and vi) reacting an appropriate amount of an amine (13) with the chloropyrimidine of Formula VI, optionally in the presence of an appropriate amount of a suitable base, in a suitable solvent, at a suitable temperature, to yield the compound of Formula IB (13)

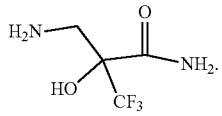

An eleventh process for making the compound of Formula IB, comprises the steps of:

a) reacting dibromopyrimidine (5) with an appropriate amount of a suitable base, in methanol or a suitable methoxide salt in a suitable aprotic solvent, at a suitable temperature, to provide, after workup, a solution of a bromopyrimidine intermediate (6) in a suitable aprotic solvent;

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst to afford after workup, a solution of intermediate (7) in a suitable solvent;

c) de-silylating intermediate (7) with an appropriate amount of a suitable fluoride reactant, a suitable acid or a suitable base, in a suitable solvent, at a suitable temperature, to provide pyrimidine intermediate (2);

d) amidating carboxylic acid (8') by reacting it with an appropriate amount of oxalyl chloride or an equivalent amide coupling reagent, in a suitable aprotic organic solvent, at a suitable temperature, in the presence of an appropriate amount of a suitable catalyst; followed by an appropriate amount of N,O-dimethylhydroxylamine or salt (e.g. HCl salt) thereof, in the presence of an appropriate excess of a suitable base, at a suitable temperature, in a suitable solvent to afford amide (1');

i) coupling an appropriate amount of intermediate amide (1') with intermediate pyrimidine (2), in a suitable aprotic organic solvent, at a suitable temperature, in the presence of an appropriate amount of a suitable base, to afford, after quenching with an acid, a solution of intermediate (3');

ii) at pH>5, optionally after addition of an appropriate amount of N,O-dimethylhydroxylamine or a salt (e.g. HCl salt) thereof, in a suitable solvent, at a suitable temperature, allowing the mixture to react to afford intermediate (4');

iiia) condensing the compound of formula (4') with an appropriate amount of hydrazine, in a suitable protic or aprotic solvent, at a suitable temperature, affording a compound of formula (24');

iiib) alkylating the compound of formula (24') with an appropriate amount of an alkylating agent of formula (23A), optionally in the presence of an appropriate amount of a suitable base, in a suitable protic or aprotic solvent, at a suitable temperature, affording the compound of Formula V;

iv) de-methylating the compound of Formula V by reacting it with an appropriate amount of a de-methylating reagent, in a suitable solvent, at a suitable temperature, to afford alcohol (9');

v) chlorinating alcohol (9') with an appropriate amount of phosphoryl chloride and, optionally, an appropriate amount of a suitable base, at a suitable temperature, optionally in a suitable aprotic organic solvent to afford the chloropyrimidine of Formula VI; and vi) reacting an appropriate amount of an amine (13) with the chloropyrimidine of Formula VI, optionally in the presence of an appropriate amount of a suitable base, in a suitable solvent, at a suitable temperature, to yield the compound of Formula IB (13)

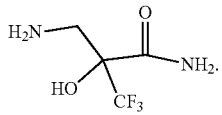

A tenth process for making the compound of Formula IC comprises the steps of:

a) reacting dibromopyrimidine (5) with an appropriate amount of a suitable base, in methanol or a suitable methoxide salt in a suitable aprotic solvent, at a suitable temperature, to provide, after workup, a solution of a bromopyrimidine intermediate (6) in a suitable aprotic solvent;

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst to afford after workup, a solution of intermediate (7) in a suitable solvent;

c) de-silylating intermediate (7) with an appropriate amount of a suitable fluoride reactant, a suitable acid or a suitable base, in a suitable solvent, at a suitable temperature, to provide pyrimidine intermediate (2);

d) amidating carboxylic acid (8') by reacting it with an appropriate amount of oxalyl chloride or an equivalent amide coupling reagent, in a suitable aprotic organic solvent, at a suitable temperature, in the presence of an appropriate amount of a suitable catalyst; followed by an appropriate amount of N,O-dimethylhydroxylamine or salt (e.g. HCl salt) thereof, in the presence of an appropriate excess of a suitable base, at a suitable temperature, in a suitable solvent to afford amide (1');

i) coupling an appropriate amount of intermediate amide (1') with intermediate pyrimidine (2), in a suitable aprotic organic solvent, at a suitable temperature, in the presence of an appropriate amount of a suitable base, to afford, after quenching with an acid, a solution of intermediate (3');

ii) at pH>5, optionally after addition of an appropriate amount of N, O-dimethylhydroxylamine or a salt (e.g., HCl salt) thereof, in a suitable solvent, at a suitable temperature, allowing the mixture to react to afford intermediate (4');

iii) condensing intermediate (4') with an appropriate amount of a hydrazine of formula

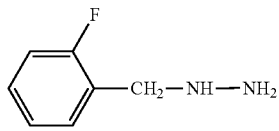

or a salt (e.g., HCl salt) thereof, optionally in the presence of an appropriate amount of a suitable base, in a suitable protic solvent, at a suitable temperature, affording a compound of Formula V;

iv) de-methylating the compound of Formula V by reacting it with an appropriate amount of a de-methylating reagent, in a suitable solvent, at a suitable temperature, to afford alcohol (9');

v) chlorinating alcohol (9') with an appropriate amount of phosphoryl chloride and, optionally, an appropriate amount of a suitable base, at a suitable temperature, optionally in a suitable aprotic organic solvent to afford the chloropyrimidine of Formula VI; and vi) reacting an appropriate amount of a chiral amine (19A) or its HCl salt (19) with the chloropyrimidine of Formula VI, optionally in the presence of an appropriate amount of a suitable base, in a suitable solvent, at a suitable temperature, to yield the compound of the compound Formula IC

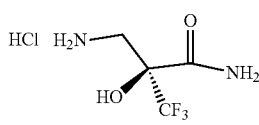

(19)

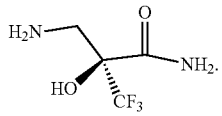

(19A)

An eleventh process for making the compound of Formula IC comprises the steps of:

a) reacting dibromopyrimidine (5) with an appropriate amount of a suitable base, in methanol or a suitable methoxide salt in a suitable aprotic solvent, at a suitable temperature, to provide, after workup, a solution of a bromopyrimidine intermediate (6) in a suitable aprotic solvent;

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst to afford after workup, a solution of intermediate (7) in a suitable solvent;

c) de-silylating intermediate (7) with an appropriate amount of a suitable fluoride reactant, a suitable acid or a suitable base, in a suitable solvent, at a suitable temperature, to provide pyrimidine intermediate (2);

d) amidating carboxylic acid (8') by reacting it with an appropriate amount of oxalyl chloride or an equivalent amide coupling reagent, in a suitable aprotic organic solvent, at a suitable temperature, in the presence of an appropriate amount of a suitable catalyst; followed by an appropriate amount of N,O-dimethylhydroxylamine or salt (e.g. HCl salt) thereof, in the presence of an appropriate excess of a suitable base, at a suitable temperature, in a suitable solvent to afford amide (1');

i) coupling an appropriate amount of intermediate amide (1') with intermediate pyrimidine (2), in a suitable aprotic organic solvent, at a suitable temperature, in the presence of an appropriate amount of a suitable base, to afford, after quenching with an acid, a solution of intermediate (3');

ii) at pH>5, optionally after addition of an appropriate amount of N,O-dimethylhydroxylamine or a salt (e.g., HCl salt) thereof, in a suitable solvent, at a suitable temperature, allowing the mixture to react to afford intermediate (4');

iiia) condensing the compound of formula (4') with an appropriate amount of hydrazine, in a suitable protic or aprotic solvent, at a suitable temperature, affording a compound of formula (24');

iiib) alkylating the compound of formula (24') with an appropriate amount of an alkylating agent of formula (23A), optionally in the presence of an appropriate amount of a suitable base, in a suitable protic or aprotic solvent, at a suitable temperature, affording the compound of Formula V;

iv) de-methylating the compound of Formula V by reacting it with an appropriate amount of a de-methylating reagent, in a suitable solvent, at a suitable temperature, to afford alcohol (9');

v) chlorinating alcohol (9') with an appropriate amount of phosphoryl chloride and, optionally, an appropriate amount of a suitable base, at a suitable temperature, optionally in a suitable aprotic organic solvent to afford the chloropyrimidine of Formula VI; and vi) reacting an appropriate amount of a chiral amine (19A) or its HCl salt (19) with the chloropyrimidine of Formula VI, optionally in the presence of an appropriate amount of a suitable base, in a suitable solvent, at a suitable temperature, to yield the compound of the compound Formula IC

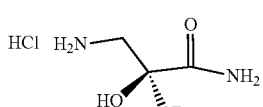

(19)

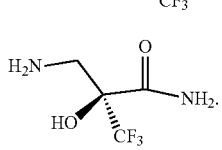

(19A)

A tenth process for making the compound of Formula ID, comprises the steps of:

a) reacting dibromopyrimidine (5) with an appropriate amount of a suitable base, in methanol or a suitable methoxide salt in a suitable aprotic solvent, at a suitable temperature, to provide, after workup, a solution of a bromopyrimidine intermediate (6) in a suitable aprotic solvent;

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst to afford after workup, a solution of intermediate (7) in a suitable solvent;

c) de-silylating intermediate (7) with an appropriate amount of a suitable fluoride reactant, a suitable acid or a suitable base, in a suitable solvent, at a suitable temperature, to provide pyrimidine intermediate (2);

d) amidating carboxylic acid (8') by reacting it with an appropriate amount of oxalyl chloride or an equivalent amide coupling reagent, in a suitable aprotic organic solvent, at a suitable temperature, in the presence of an appropriate amount of a suitable catalyst; followed by an appropriate amount of N,O-dimethylhydroxylamine or salt (e.g. HCl salt) thereof, in the presence of an appropriate excess of a suitable base, at a suitable temperature, in a suitable solvent to afford amide (1');

i) coupling an appropriate amount of intermediate amide (1') with intermediate pyrimidine (2), in a suitable aprotic organic solvent, at a suitable temperature, in the presence of an appropriate amount of a suitable base, to afford, after quenching with an acid, a solution of intermediate (3');

ii) at pH>5, optionally after addition of an appropriate amount of N, O-dimethylhydroxylamine or a salt (e.g. HCl salt) thereof, in a suitable solvent, at a suitable temperature, allowing the mixture to react to afford intermediate (4');

iii) condensing intermediate (4') with an appropriate amount of a hydrazine of formula

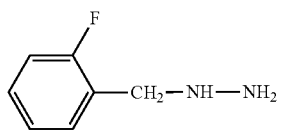

or its salt (e.g., HCl salt) thereof, optionally in the presence of an appropriate amount of a suitable base, in a suitable protic or aprotic solvent, at a suitable temperature, affording a compound of Formula V;

iv) de-methylating the compound of Formula V by reacting it with an appropriate amount of a de-methylating reagent, in a suitable solvent, at a suitable temperature, to afford alcohol (9');

v) chlorinating alcohol (9') with an appropriate amount of phosphoryl chloride and, optionally, an appropriate amount of a suitable base, at a suitable temperature, optionally in a suitable aprotic organic solvent to afford the chloropyrimidine of Formula VI; and vi) reacting an appropriate amount of a chiral amine (15A) or its HCl salt (15) with the chloropyrimidine of Formula VI, optionally in the presence of an appropriate amount of a suitable base, in a suitable solvent, at a suitable temperature, to yield the compound of Formula

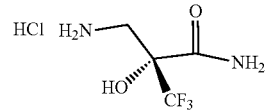

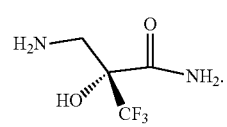

An eleventh process for making the compound of Formula ID, comprises the steps of:

a) reacting dibromopyrimidine (5) with an appropriate amount of a suitable base, in methanol or a suitable methoxide salt in a suitable aprotic solvent, at a suitable temperature, to provide, after workup, a solution of a bromopyrimidine intermediate (6) in a suitable aprotic solvent;

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst to afford after workup, a solution of intermediate (7) in a suitable solvent;

c) de-silylating intermediate (7) with an appropriate amount of a suitable fluoride reactant, a suitable acid or a suitable base, in a suitable solvent, at a suitable temperature, to provide pyrimidine intermediate (2);

d) amidating carboxylic acid (8') by reacting it with an appropriate amount of oxalyl chloride or an equivalent amide coupling reagent, in a suitable aprotic organic solvent, at a suitable temperature, in the presence of an appropriate amount of a suitable catalyst; followed by an appropriate amount of N,O-dimethylhydroxylamine or salt (e.g. HCl salt) thereof, in the presence of an appropriate excess of a suitable base, at a suitable temperature, in a suitable solvent to afford amide (1');

i) coupling an appropriate amount of intermediate amide (1') with intermediate pyrimidine (2), in a suitable aprotic organic solvent, at a suitable temperature, in the presence of an appropriate amount of a suitable base, to afford, after quenching with an acid, a solution of intermediate (3');

ii) at pH>5, optionally after addition of an appropriate amount of N,O-dimethylhydroxylamine or a salt (e.g. HCl salt) thereof, in a suitable solvent, at a suitable temperature, allowing the mixture to react to afford intermediate (4');

iiia) condensing the compound of formula (4') with an appropriate amount of hydrazine, in a suitable protic or aprotic solvent, at a suitable temperature, affording a compound of formula (24');

iiib) alkylating the compound of formula (24') with an appropriate amount of an alkylating agent of formula (23A), optionally in the presence of an appropriate amount of a suitable base, in a suitable protic or aprotic solvent, at a suitable temperature, affording the compound of Formula V;

iv) de-methylating the compound of Formula V by reacting it with an appropriate amount of a de-methylating reagent, in a suitable solvent, at a suitable temperature, to afford alcohol (9');

v) chlorinating alcohol (9') with an appropriate amount of phosphoryl chloride and, optionally, an appropriate amount of a suitable base, at a suitable temperature, optionally in a suitable aprotic organic solvent to afford the chloropyrimidine of Formula VI; and vi) reacting an appropriate amount of a chiral amine (15A) or its HCl salt (15) with the chloropyrimidine of Formula VI, optionally in the presence of an appropriate amount of a suitable base, in a suitable solvent, at a suitable temperature, to yield the compound of Formula ID

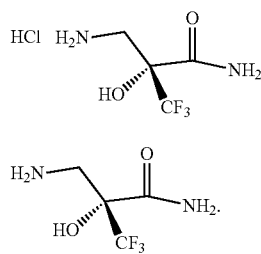

A twelfth process for making the compound of Formula IC comprises the steps of:

a) reacting dibromopyrimidine (5) with an appropriate amount of a suitable base, in methanol or a suitable methoxide salt in a suitable aprotic solvent, at a suitable temperature, to provide, after workup, a solution of a bromopyrimidine intermediate (6) in a suitable aprotic solvent;

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst; to afford after workup, a solution of intermediate (7) in a suitable solvent;

c) de-silylating intermediate (7) with an appropriate amount of a suitable fluoride reactant, a suitable acid or a suitable base, in a suitable solvent, at a suitable temperature, to provide pyrimidine intermediate (2);

d) amidating carboxylic acid (8') by reacting it with an appropriate amount of oxalyl chloride or an equivalent amide coupling reagent, in a suitable aprotic organic solvent, at a suitable temperature, in the presence of an appropriate amount of a suitable catalyst; followed by an appropriate amount of N,O-dimethylhydroxylamine or salt (e.g. HCl salt) thereof, in the presence of an appropriate excess of a suitable base, at a suitable temperature, in a suitable solvent to afford amide (1');

i) coupling an appropriate amount of intermediate amide (1') with intermediate pyrimidine (2), in a suitable aprotic organic solvent, at a suitable temperature, in the presence of an appropriate amount of a suitable base, to afford, after quenching with an acid, a solution of intermediate (3');

ii) at pH>5, optionally after addition of an appropriate amount of N, O-dimethylhydroxylamine or a salt (e.g. HCl salt) thereof, in a suitable solvent, at a suitable temperature, allowing the mixture to react to afford intermediate (4');

iii) condensing intermediate (4') with an appropriate amount of a hydrazine of formula

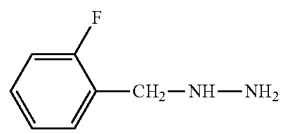

or a salt (e.g. HCl salt) thereof, optionally in the presence of an appropriate amount of a suitable base, in a suitable protic solvent, at a suitable temperature, affording a compound of Formula V;

iv) de-methylating the compound of Formula V by reacting it with an appropriate amount of a de-methylating reagent, in a suitable solvent, at a suitable temperature, to afford alcohol (9');

v) chlorinating alcohol (9') with an appropriate amount of phosphoryl chloride and, optionally, an appropriate amount of a suitable base, at a suitable temperature, optionally in a suitable aprotic organic solvent to afford the chloropyrimidine of Formula VI; and vi) reacting an appropriate amount of an (L)-malic acid salt (18) of an amine (21) with the chloropyrimidine of Formula VI, optionally in the presence of an appropriate amount of a suitable base, in a suitable solvent, at a suitable temperature, to yield the compound of Formula IC

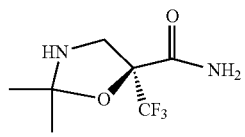

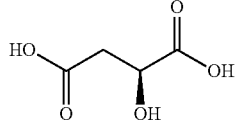

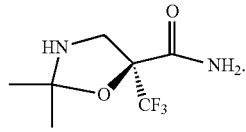

A thirteenth process for making the compound of Formula IC comprises the steps of:

a) reacting dibromopyrimidine (5) with an appropriate amount of a suitable base, in methanol or a suitable methoxide salt in a suitable aprotic solvent, at a suitable temperature, to provide, after workup, a solution of a bromopyrimidine intermediate (6) in a suitable aprotic solvent;

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst; to afford after workup, a solution of intermediate (7) in a suitable solvent;

c) de-silylating intermediate (7) with an appropriate amount of a suitable fluoride reactant, a suitable acid or a suitable base, in a suitable solvent, at a suitable temperature, to provide pyrimidine intermediate (2);

d) amidating carboxylic acid (8') by reacting it with an appropriate amount of oxalyl chloride or an equivalent amide coupling reagent, in a suitable aprotic organic solvent, at a suitable temperature, in the presence of an appropriate amount of a suitable catalyst; followed by an appropriate amount of N,O-dimethylhydroxylamine or salt (e.g. HCl salt) thereof, in the presence of an appropriate excess of a suitable base, at a suitable temperature, in a suitable solvent to afford amide (1');

i) coupling an appropriate amount of intermediate amide (1') with intermediate pyrimidine (2), in a suitable aprotic organic solvent, at a suitable temperature, in the presence of an appropriate amount of a suitable base, to afford, after quenching with an acid, a solution of intermediate (3');

ii) at pH>5, optionally after addition of an appropriate amount of N, O-dimethylhydroxylamine or a salt (e.g. HCl salt) thereof, in a suitable solvent, at a suitable temperature, allowing the mixture to react to afford intermediate (4');

iiia) condensing the compound of formula (4') with an appropriate amount of hydrazine, in a suitable protic or aprotic solvent, at a suitable temperature, affording a compound of formula (24');

iiib) alkylating the compound of formula (24') with an appropriate amount of an alkylating agent of formula (23A), optionally in the presence of an appropriate amount of a suitable base, in a suitable protic or aprotic solvent, at a suitable temperature, affording the compound of Formula V;

iv) de-methylating the compound of Formula V by reacting it with an appropriate amount of a de-methylating reagent, in a suitable solvent, at a suitable temperature, to afford alcohol (9');

v) chlorinating alcohol (9') with an appropriate amount of phosphoryl chloride and, optionally, an appropriate amount of a suitable base, at a suitable temperature, optionally in a suitable aprotic organic solvent to afford the chloropyrimidine of Formula VI; and vi) reacting an appropriate amount of an (L)-malic acid salt (18) of an amine (21) with the chloropyrimidine of Formula VI, optionally in the presence of an appropriate amount of a suitable base, in a suitable solvent, at a suitable temperature, to yield the compound of Formula IC

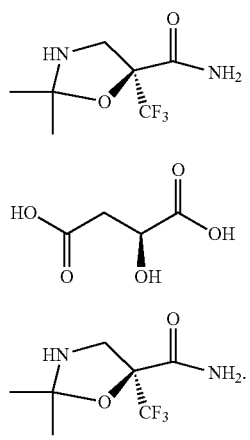

(18)

(21)

A twelfth process for making the compound of Formula ID comprises the steps of:

a) reacting dibromopyrimidine (5) with an appropriate amount of a suitable base, in methanol or a suitable methoxide salt in a suitable aprotic solvent, at a suitable temperature, to provide, after workup, a solution of a bromopyrimidine intermediate (6) in a suitable aprotic solvent;

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst; after workup, a solution of intermediate (7) in a suitable solvent;

c) de-silylating intermediate (7) with an appropriate amount of a suitable fluoride reactant, a suitable acid or a suitable base, in a suitable solvent, at a suitable temperature, to provide pyrimidine intermediate (2);

d) amidating carboxylic acid (8') by reacting it with an appropriate amount of oxalyl chloride or an equivalent amide coupling reagent, in a suitable aprotic organic solvent, at a suitable temperature, in the presence of an appropriate amount of a suitable catalyst; followed by an appropriate amount of N,O-dimethylhydroxylamine or salt (e.g. HCl salt) thereof, in the presence of an appropriate excess of a suitable base, at a suitable temperature, in a suitable solvent to afford amide (1');

i) coupling an appropriate amount of intermediate amide (1') with intermediate pyrimidine (2), in a suitable aprotic organic solvent, at a suitable temperature, in the presence of an appropriate amount of a suitable base, to afford, after quenching with an acid, a solution of intermediate (3');

ii) at pH>5, optionally after addition of an appropriate amount of N,O-dimethylhydroxylamine or a salt (e.g. HCl salt) thereof, in a suitable solvent, at a suitable temperature, allowing the mixture to react to afford intermediate (4');

iii) condensing intermediate (4') with an appropriate amount of a hydrazine of formula

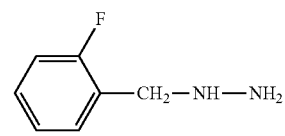

or a salt (e.g. HCl salt) thereof, optionally in the presence of an appropriate amount of a suitable base, in a suitable protic or aprotic solvent, at a suitable temperature, affording a compound of Formula V;

iv) de-methylating the compound of Formula V by reacting it with an appropriate amount of a de-methylating reagent, in a suitable solvent, at a suitable temperature, to afford alcohol (9');

v) chlorinating alcohol (9') with an appropriate amount of phosphoryl chloride and, optionally, an appropriate amount of a suitable base, at a suitable temperature, optionally in a suitable aprotic organic solvent to afford the chloropyrimidine of Formula VI; and vi) reacting an appropriate amount of a (D)-malic acid salt (14) of an amine (20) with the chloropyrimidine of Formula VI, optionally in the presence of an appropriate amount of a suitable base, in a suitable solvent, at a suitable temperature, to yield the compound of Formula ID

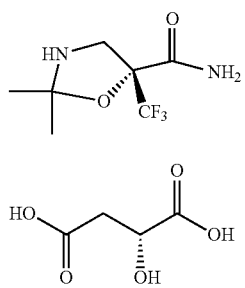

(14)

(20)

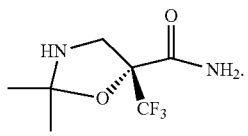

A thirteenth process for making the compound of Formula ID comprises the steps of:

a) reacting dibromopyrimidine (5) with an appropriate amount of a suitable base, in methanol or a suitable methoxide salt in a suitable aprotic solvent, at a suitable temperature, to provide, after workup, a solution of a bromopyrimidine intermediate (6) in a suitable aprotic solvent;

b) coupling bromopyrimidine intermediate (6) with an appropriate amount of ethynyltrimethylsilane, in a suitable aprotic organic solvent, at a suitable temperature, in the presence of an appropriate amount of a suitable base, in the presence of an appropriate amount of an optional suitable Cu(I) catalyst and an appropriate amount of a suitable Pd catalyst; after workup, a solution of intermediate (7) in a suitable solvent;

c) de-silylating intermediate (7) with an appropriate amount of a suitable fluoride reactant, a suitable acid or a suitable base, in a suitable solvent, at a suitable temperature, to provide pyrimidine intermediate (2);

d) amidating carboxylic acid (8') by reacting it with an appropriate amount of oxalyl chloride or an equivalent amide coupling reagent, in a suitable aprotic organic solvent, at a suitable temperature, in the presence of an appropriate amount of a suitable catalyst; followed by an appropriate amount of N,O-dimethylhydroxylamine or salt (e.g. HCl salt) thereof, in the presence of an appropriate excess of a suitable base, at a suitable temperature, in a suitable solvent to afford amide (1');

i) coupling an appropriate amount of intermediate amide (1') with intermediate pyrimidine (2), in a suitable aprotic organic solvent, at a suitable temperature, in the presence of an appropriate amount of a suitable base, to afford, after quenching with an acid, a solution of intermediate (3');

ii) at pH>5, optionally after addition of an appropriate amount of N, O-dimethylhydroxylamine or a salt (e.g. HCl salt) thereof, in a suitable solvent, at a suitable temperature, allowing the mixture to react to afford intermediate (4');

iiia) condensing the compound of formula (4') with an appropriate amount of hydrazine, in a suitable protic or aprotic solvent, at a suitable temperature, affording a compound of formula (24');

iiib) alkylating the compound of formula (24') with an appropriate amount of an alkylating agent of formula (23A), optionally in the presence of an appropriate amount of a suitable base, in a suitable protic or aprotic solvent, at a suitable temperature, affording the compound of Formula V;

iv) de-methylating the compound of Formula V by reacting it with an appropriate amount of a de-methylating reagent, in a suitable solvent, at a suitable temperature, to afford alcohol (9');

v) chlorinating alcohol (9') with an appropriate amount of phosphoryl chloride and, optionally, an appropriate amount of a suitable base, at a suitable temperature, optionally in a suitable aprotic organic solvent to afford the chloropyrimidine of Formula VI; and vi) reacting an appropriate amount of a (D)-malic acid salt (14) of an amine (20) with the chloropyrimidine of Formula VI, optionally in the presence of an appropriate amount of a suitable base, in a suitable solvent, at a suitable temperature, to yield the compound of Formula ID

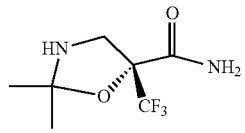

(14)

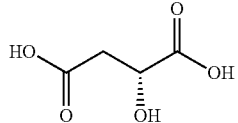

(20)

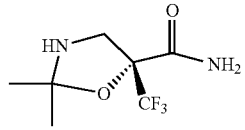

In some embodiments of the above processes for making the compound of Formula ID, the compound of Formula ID can be obtained as a specific polymorph (Form B). The preparation of polymorph Form B of the compound of Formula ID involves the additional steps of:

A") dissolving the compound of Formula ID obtained in step vi) in acetonitrile and water at an appropriate temperature between 70° C. and 75° C.;

B") filtering the solution of step A") to form a filtered solution of the compound;

C") heating the filtered solution at an appropriate temperature between 65° C. and 75° C. and adding water to form a slurry;

D") cooling the slurry of step C") to a temperature between 0° C. and 5° C. to yield crystalline Form B of the compound of Formula ID; and E") filtering, washing with a mixture of acetonitrile and water, and drying the crystalline Form B of Compound ID.

For step i) of any of the above processes towards the synthesis of a compound of Formula II, a compound of Formula III, a compound of Formula IV, a compound of Formula V, a compound of Formula VI, a compound of Formula VII, a compound of Formula IA, a compound of Formula IB, a compound of Formula IC or a compound of Formula ID and step i) in the $1^{st}$ to $38^{th}$ specific embodiments described above:

An appropriate amount of intermediate amide (1') or intermediate amide (1) is at least one equivalent of amide (1) or amide (1') per equivalent of intermediate pyrimidine (2). In some embodiments, an appropriate amount is between 0.95 and 1.2 equivalents of amide (1) or (1') per 1 equivalent of the pyrimidine (2). In other embodiments, it is between 1 and 1.1 equivalents. In other embodiments it is between 1 and 1.05 equivalents. In still other embodiments, it is one equivalent. In yet other embodiments, it is 1.05 equivalents.

A suitable aprotic organic solvent is, an anhydrous organic solvent, for example, THF or hexanes, or a mixture of THF and hexanes. Other suitable aprotic solvents are, for instance, 2-methyltetrahydrofuran or toluene.

A suitable temperature is below −40° C. In some embodiments, a suitable temperature is between −90° C. and −40° C. In some embodiments, a suitable temperature is one between −90° C. to −45° C. In other embodiments, a suitable temperature is one between −90° C. to −50° C. In some embodiments, a suitable temperature is between −90° C. to −60° C. In some embodiments, a suitable temperature is between −80° C. to −60° C. In some embodiments, a suitable temperature is between −78° C. to −60° C. In other embodiments, a suitable temperature is between −65° C. to −55° C. In still other embodiments, a suitable temperature is between −70° C. to −60° C. In yet other embodiments, a suitable temperature is below −55° C.

A suitable base is, for example, n-butyllithium. Other suitable bases are bis(trimethylsilyl)amide (HMDS), sodium bis(trimethylsilyl)amide (NaHMDS), lithium bis(trimethylsilyl)amide (LiHMDS), potassium bis(trimethylsilyl)amide (KHMDS), sodium hydride (NaH), iso-propylmagnsium chloride (iPrMgCl), methylmagnesium chloride (MeMgCl) and lithium diisopropylamide (LDA). Each of these bases is usually added to the reaction mixture in the form of a solution in an organic non-protic solvent. For example, n-butyllithium can be added as a solution in hexanes.

An appropriate amount of a suitable base is between 0.90 equivalent and 1.2 equivalents per each equivalent of intermediate (2). In some embodiments, it is between 0.9 equivalent and 1.5 equivalents. In some embodiments, it is between 0.9 equivalent and 1.3 equivalents. In other embodiments, it is between 1.1 equivalents and 1.5 equivalents. In still other embodiments, it is between 1.1 equivalents and 1.4 equivalents. In yet other embodiments it is between 1.1 equivalents and 1.3 equivalents. In yet other embodiments it is 1 equivalent.

In some embodiments, the reaction of intermediate amide (1) and pyrimidine (2) is quenched with an acid. In one embodiment, the acid is an aqueous acid, for example, hydrochloric acid. In another embodiment, the acid is non-aqueous acid, such as glacial acetic acid.

In some embodiments, the reaction mixture of intermediate amide (1) and pyrimidine (2) comprising the product intermediate (3) in taken directly to the step ii). In some embodiment, the product intermediate (3) is isolated before the reaction of step ii).

For step ii) of any of the above processes towards the synthesis of a compound of a compound of Formula II, a compound of Formula III, a compound of Formula IV, a compound of Formula V, a compound of Formula VI, a compound of Formula VII, a compound of Formula IA, a compound of Formula IB, a compound of Formula IC or a compound of Formula ID and step ii) in the $1^{st}$ to $38^{th}$ specific embodiments described above:

In some embodiments, N,O-dimethylhydroxylamine is added as the HCl salt.

An appropriate amount of N,O-dimethylhydroxylamine hydrochloride is between 0 and 1.5 equivalents of N,O-dimethylhydroxylamine hydrochloride per equivalent of intermediate pyrimidine (2). In some embodiments, an appropriate amount is between 0 and 1.0 equivalent. In some embodiments, an appropriate amount is between 0 and 1.4 equivalents. In some embodiments, an appropriate amount is between 0 and 1.2 equivalents. In other embodiments, it is between 0.1 and 0.9. In still other embodiments it is 0.6 or 0.5 equivalents. In other embodiments, no extra N,O-dimethylhydroxylamine is added in step ii).

A suitable solvent is a protic or non-protic solvent. Examples of protic solvents are, for example, water or an aqueous acid solution. A suitable solvent that is an aqueous acid solution is, for example, an HCl solution, an AcOH solution, or an $H_2SO_4$ solution. In some embodiments, no added acid needs to be used in this step and the quenching works when at least 1 equivalent of N,O-dimethylhydroxylamine hydrochloride is used alone, in the absence of added acid. In other embodiments the acidic quenching is carried out with one of the acidic aqueous solutions listed above and in the absence of added hydroxylamine hydrochloride. In some embodiments, the solvent is a mixture of an aqueous acidic solvent with a non-protic solvent. For example, the solvent can be a mixture of aqueous HCl with ethyl acetate. Other alternative solvents include, for instance 2-methylTHF, THF, MTBE, or mixtures of all the above suitable solvents thereof. In one embodiment, the solvent is an organic solvent or solvents, such as ethyl acetate, 2-methylTHF, THF, MTBE, or a mixture thereof. In another embodiment, the solvent is an acidic anhydrous organic solvent, such as glacial acetic acid. In another embodiment, the solvent is an organic solvent comprising anhydrous acid, such as glacial acetic acid.

A suitable temperature is between 0° C. and 30° C. In some embodiments, a suitable temperature is between 0° C. and 25° C. In other embodiments it is between 0° C. and 5° C. In other embodiments it is between 5° C. and 30° C. In other embodiments it is between 5° C. and 25° C. In other embodiments it is between 10° C. and 25° C. In other embodiments it is between 15° C. and 25° C.

In order to achieve a pH>5, the reaction mixture pH is adjusted after the solution obtained in step i), containing intermediate (3'), is added to the acidic reaction mixture, optionally containing N,O-dimethylhydroxylamine hydrochloride. The reaction mixture may be acidic because of the presence of N,O-dimethylhydroxylamine hydrochloride or the presence of an added aqueous acid or both. Alternatively, the acidic reaction mixture contains a non-aqueous acid in an organic solvent and optionally N,O-dimethylhydroxylamine hydrochloride. In one embodiment, the solution obtained in step i) is added to the acidic reaction mixture containing glacial acetic acid and N,O-dimethylhydroxylamine hydrochloride in ethyl acetate. In some embodiments, the solution obtained in step i), containing intermediate (3'), is added to an acidic reaction mixture and optionally N,O-dimethylhydroxylamine or a salt thereof (e.g. HCl salt) is added after acidic quenching has already occurred. The suitable pH>5 may be obtained by addition of an aqueous base, for example, a saturated sodium bicarbonate solution or a saturated potassium bicarbonate solution or a similar base. In some embodiments, the optional added N,O-dimethylhydroxylamine or a salt (e.g. HCl salt) thereof may be added after the base, in other embodiments it may be added before the base. In some embodiments, a suitable resulting pH is any pH above 5 and below 9. In other embodiments, a suitable pH is above 6 and below 9. In still other embodiments, a suitable pH is above 7 and below 9. In other embodiments, a suitable pH is between 6.5 and 9. In still other embodiments, the pH of the mixture is adjusted to a pH of between 7 and 8. In yet other embodiments, a suitable pH is between 6.5 and 8.5. In still other embodiments the suitable pH is between 6.75 and 8.25. In still other embodiments, a suitable pH is between 6.5 and 9.

For step iii) of any of the above processes towards the synthesis of a compound of a compound of Formula II, a compound of Formula III, a compound of Formula IV, a compound of Formula V, a compound of Formula VI, a compound of Formula VII, a compound of Formula IA, a compound of Formula IB, a compound of Formula IC or a compound of Formula ID and step iii) in the $2^{nd}$, $4^{th}$, $6^{th}$, $8^{th}$, $10^{th}$, $11^{th}$, $12^{th}$, $14^{th}$, $16^{th}$, $18^{th}$, $20^{th}$, $22^{nd}$, $23^{rd}$, $24^{th}$, $26^{th}$, $28^{th}$, $30^{th}$, $32^{nd}$, $34^{th}$, $36^{th}$, $37^{th}$ and $38^{th}$ specific embodiments described above:

- In some embodiments, the hydrazine is used in the form of a salt. In some embodiments, it is the hydrochloride salt.
- An appropriate amount of a hydrazine of formula $R^2$—$CH_2$—NH—$NH_2$ or a salt (e.g. HCl salt) thereof, is at least one equivalent of hydrazine per each equivalent of intermediate (4) or intermediate (4'). In some embodiments, an appropriate amount of hydrazine is between 1 equivalent and 2 equivalents. In other embodiments, it is between 1 equivalent and 1.5 equivalent. In still other embodiments, it is between 1 equivalent and 1.3 equivalents. In still other embodiments, it is between 1.1 equivalents and 1.4 equivalents. In still other embodiments it is between 1.1 equivalents and 1.3 equivalents. In yet other embodiments it is 1.2 equivalents.
- An optional suitable base is, for instance, potassium carbonate ($K_2CO_3$). Other optional suitable bases in this step are, for example, sodium acetate (NaOAc), sodium carbonate ($Na_2CO_3$), sodium hydrogen carbonate ($NaHCO_3$) and potassium bicarbonate ($KHCO_3$).
- An appropriate amount of a suitable base is an amount that will partially or totally neutralize the acid from the hydrazine hydrochloride, when the hydrochloride form of the hydrazine is used. For instance, 0.5 to 1.1 equivalents of base per each equivalent of hydrazine hydrochloride. In other embodiments, an appropriate amount is 0.5 to 0.9 equivalents. In still other embodiments, it is 0.65 equivalents. In yet other embodiments, it is 0.6 equivalents. In still other embodiments it is between 0.9 and 1.1 equivalents.
- A suitable solvent is, for instance, methanol, ethanol or isopropanol. Other solvents that may be used in this step are, for example dichloromethane, THF, $CH_3CN$, DMSO, DMF, $CHCl_3$, dioxane and DMA. When an optional suitable base is used, the base will be dissolved or suspended in water before mixing it with the hydrazine hydrochloride dissolved in the suitable protic or aprotic solvent. The mixture of the hydrazine hydrochloride and optional suitable base in a protic or aprotic solvent and water will then be mixed with a solution of the intermediate (4) or (4') in the suitable protic or aprotic solvent. Therefore, the reaction in this case will be run in a mixture of a protic or aprotic solvent and water.
- A suitable temperature is between 10° C. and 40° C. In other embodiments, a suitable temperature is between 15° C. and 30° C. In some embodiments, it is between 10° C. and 30° C. In other embodiments, it is between 15° C. and 30° C. In other embodiments, it is between 15° C. and 25° C. In still other embodiments, it is between 20° C. and 25° C.

For step iiia) of any of the above processes towards the synthesis of a compound of a compound of Formula II, a compound of Formula III, a compound of Formula IV, a compound of Formula V, a compound of Formula VI, a compound of Formula VII, a compound of Formula IA, a compound of Formula IB, a compound of Formula IC or a compound of Formula ID and step iiia) in the $3^{rd}$, $5^{th}$, $7^{th}$, $9^{th}$, $10^{th}$, $11^{th}$, $12^{th}$, $15^{th}$, $17^{th}$, $19^{th}$, $21^{st}$, $22^{nd}$, $23^{rd}$, $25^{th}$, $27^{th}$, $29^{th}$, $31^{st}$, $33^{rd}$, $35^{th}$, $36^{th}$, $37^{th}$ and $38^{th}$ specific embodiments described above:

- An appropriate amount of hydrazine (e.g. hydrazine hydrate), is at least one equivalent of hydrazine per each equivalent of intermediate (4) or intermediate (4'). In some embodiments, an appropriate amount of hydrazine is between 1 equivalent and 5 equivalents. In other embodiments, it is between 1 equivalent and 2 equivalents. In other embodiments, it is between 1.5 equivalent and 1.8 equivalent. In still other embodiments, it is between 1.5 equivalent and 1.7 equivalents. In still other embodiments, it is between 1.55 and 1.65 equivalents. In yet other embodiments it is 1.6 equivalents.
- In some embodiments, an optional suitable base is used in the reaction. An optional suitable base is, for instance, potassium carbonate ($K_2CO_3$). Other optional suitable bases in this step are, for example, sodium acetate (NaOAc), sodium carbonate ($Na_2CO_3$), sodium hydrogen carbonate ($NaHCO_3$) and potassium bicarbonate ($KHCO_3$).
- A suitable solvent is, for instance, methanol, ethanol or isopropanol. Other protic or aprotic solvents that may be used in this step are, for example dichloromethane, THF, dioxane, $CH_3CN$, $CHCl_3$, DMSO, DMF and DMA. In some embodiments, the reaction will be run in a mixture of a protic or aprotic solvent and water.
- A suitable temperature is between 5° C. and 100° C. In other embodiments, a suitable temperature is between 10° C. and 80° C. In some embodiments, it is between 10° C. and 50° C. In other embodiments, it is between 15° C. and 30° C. In other embodiments, it is between 15° C. and 35° C. In still other embodiments, it is between 20° C. and 30° C. In yet other embodiments, it is between 20° C. and 25° C.

For step iiib) of any of the above processes towards the synthesis of a compound of a compound of Formula II, a compound of Formula III, a compound of Formula IV, a compound of Formula V, a compound of Formula VI, a compound of Formula VII, a compound of Formula IA, a compound of Formula IB, a compound of Formula IC or a compound of Formula ID and step iiib) in the $3^{rd}$, $5^{th}$, $7^{th}$, $9^{th}$, $10^{th}$, $11^{th}$, $12^{th}$, $15^{th}$, $17^{th}$, $19^{th}$, $21^{st}$, $22^{nd}$, $23^{rd}$, $25^{th}$, $27^{th}$, $29^{th}$, $31^{st}$, $33^{rd}$, $35^{th}$, $36^{th}$, $37^{th}$ and $38^{th}$ specific embodiments described above:

- An appropriate amount of the alkylating agent of formula (22) or (23A), is at least one equivalent of the alkylating agent per each equivalent of intermediate (24) or intermediate (24'). In some embodiments, an appropriate amount of the alkylating reagent is between 1 equivalent and 5 equivalents. In other embodiments, it is between 1 equivalent and 2 equivalents. In other embodiments, it is between 1 equivalent and 1.5 equivalent.
- In some embodiments, the reaction is carried out in the presence of an appropriate amount of a suitable base. A suitable base, for instance, is alkoxide (e.g., lithim tert-butoxide (LTB), potassium tert-butoxide (KTB), sodium tert-butoxide (STB)), bis(trimethylsilylyl)amine (HMDS), sodium bis(trimethylsilyl)amide (NaHMDS), lithium bis(trimethylsilyl)amide (LiHMDS), potassium bis(trimethylsilyl)amide (KHMDS), NaH or lithium diisopropylamide (LDA). An appropriate amount of base is, for instance, between 1 and 1.5 equivalents of base.

A suitable solvent is, for instance, an ether, dioxane or THF. In some embodiments, the ether is dimethylethylether (DME). Other protic or aprotic solvents that may be used in this step are, for example dichloromethane, $CH_3CN$, DMA, DMF, DMSO and $CHCl_3$. In some embodiments the suitable solvent is selected froman ethereal solvent comprising an alkyl ether, dioxane, THF or DME. In other embodiments, it is selected from dichloromethane, $CH_3CN$, DMA, DMSO and $CHCl_3$ A suitable temperature is between −10° C. and 50° C. In other embodiments, a suitable temperature is between −10° C. and 30° C. In some embodiments, it is between 0° C. and 30° C. In other embodiments, it is between 15° C. and 30° C. In other embodiments, it is between 15° C. and 25° C. In still other embodiments, it is between 20° C. and 25° C. In yet other embodiments it is between −10° C. and 0° C. In yet other embodiments it is between −10° C. and 5° C.

In some embodiments, for the alkylating agent of formula (22) or (23A), X is —F, —Cl, —Br, —I, mesylate (—$OSO_2CH_3$), tosylate (—$OSO_2PhCH_3$), or triflate (—$OSO_2CF_3$). In some embodiments, X is —Br.

For step a) of any of the above processes for the synthesis of a compound of a compound of Formula II, a compound of Formula III, a compound of Formula IV, a compound of Formula V, a compound of Formula VI, a compound of Formula VII, a compound of Formula IA, a compound of Formula IB, a compound of Formula IC or a compound of Formula ID and step a) for the preparation of the compound of formula (6) described in the $10^{th}$, $11^{th}$, $12^{th}$, $22^{nd}$, $23^{rd}$, $36^{th}$, $37^{th}$ and $38^{th}$ specific embodiments described above:

A suitable methoxide salt is, for example, MeONa, MeOLi, MeOK, MeOCs, or similar methoxides, and MeOH or a suitable aprotic solvent is used as the solvent. In other embodiments, a suitable base is, for example, $K_2CO_3$, $Na_2CO_3$, $Cs_2CO_3$, $KHCO_3$ or similar bases, and then MeOH is used as the solvent. In one embodiment, the dibromopyrimidine compound of formula (5) is reacted with a methoxide salt (e.g., MeONa) in methanol.

An appropriate amount of the suitable base is at least one equivalent of the base for each equivalent of dibromopyrimidine (5). In other embodiments it is between 0.9 and 1.2 equivalents. In other embodiments, it is between 1 and 1.1 equivalents. In other embodiments it is 1.01 equivalents of the base for each equivalent of dibromopyrimidine (5). In other embodiments it is 1.02 equivalents of base for each equivalent of dibromopyrimidine (5).

A suitable aprotic solvent when MeOH is not the solvent is, for example THF or a similar solvent.

A suitable temperature is between −25° C. and 15° C. In some embodiments, a suitable temperature is between −20° C. and 10° C. In other embodiments, it is between −15° C. and 5° C. In still other embodiments, it is between −15° C. and 0° C. In still other embodiments, it is between −20° C. and 5° C. In still other embodiments, it is between −15° C. and 5° C. In yet other embodiments, it is between −15° C. and −5° C.

A suitable aprotic solvent in which the intermediate pyrimidine (6) in carried to the next step is, for example an ether. In one embodiment, the ether is methyl-tert-butyl ether. In other embodiments, a suitable aprotic solvent is, for example, $CH_2Cl_2$, EtOAc, THF, toluene or a similar solvent.

For step b) of any of the above processes towards the synthesis of a compound of Formula II, a compound of Formula III, a compound of Formula IV, a compound of Formula V, a compound of Formula VI, a compound of Formula VII, a compound of Formula IA, a compound of Formula IB, a compound of Formula IC or a compound of Formula ID and step b) for the preparation of the compound of formula (7) described in the $10^{th}$, $11^{th}$, $12^{th}$, $22^{nd}$, $23^{rd}$, $36^{th}$, $37^{th}$ and $38^{th}$ specific embodiments described above:

An appropriate amount of ethynyltrimethylsilane is at least one equivalent of ethynyltrimethylsilane per equivalent of intermediate (6) generated in the previous step. In some embodiments, an appropriate amount of ethynyltrimethylsilane is between 1.0 and 2.0. In other embodiments, it is between 1 and 1.8 equivalents. In other embodiments, it is between 1 and 1.6 equivalents. In still other embodiments it is between 1 and 1.5 equivalents. In still other embodiments it is between 1 and 1.3 equivalents. In other embodiments it is between 1.0 equivalents and 1.2 equivalents. In yet other embodiments it is 1.2 equivalents.

A suitable aprotic organic solvent is, for example, an ether. In one embodiment, the ether is methyl-tert-butyl ether. In other embodiments, a suitable aprotic solvent is for example EtOAc, THF, toluene, $CH_2Cl_2$ or a similar solvent.

A suitable temperature is between 15° C. and 40° C. In one embodiment, a suitable temperature is between 15° C. and 35° C. In other embodiments, it is between 15° C. and 30° C. In other embodiments, it is between 18° C. and 30° C. In still other embodiments, it is between 20° C. and 30° C. In yet other embodiments, a suitable temperature is 25° C.

A suitable base is, for example, triethylamine, Hunig's base, $Et_2NH$, $iPr_2NH$, piperidine, pyrrolidine, $K_2CO_3$, $Na_2CO_3$, $Cs_2CO_3$, $K_3PO_4$ or similar.

An appropriate amount of a suitable base is at least 1 equivalents of the suitable base for each equivalent of intermediate pyrimidine (6). In some embodiments it is between 1 and 10 equivalents. In other embodiments, it is between 1 and 5 equivalents. In other embodiments, it is between 1 and 3 equivalents. In still other embodiments it is between 1.5 and 2.5 equivalents. In still other embodiments, it is 2 equivalents. In yet other embodiments, the appropriate amount of a suitable base could be a large excess, for example, the base could be used as the solvent in the reaction.

A suitable optional Cu(I) salt is, for example, CuCl, CuBr, CuI or CuOTf. In some embodiments, the reaction can be carried out without copper catalyst (copper free conditions).

An appropriate amount the Cu(I) salt is a catalytic amount. A catalytic amount can be any amount below 1 equivalent of the Cu(I) salt for each equivalent of intermediate pyrimidine (6). In some embodiments, the catalytic amount is between above 0 and below 1 equivalents. In other embodiments, the catalytic amount is between above 0 and below 0.75 equivalents. In other embodiments it is between 0 and 0.5 equivalents, or between 0 and 0.25 equivalents, or between 0 and 0.1 equivalents, or between 0 and 0.01 equivalents. In still other embodiments, a catalytic amount of the Cu(I) salt is, for example between 0.0025 and 0.006 equivalents of Cu (I) salt per each equivalent of intermediate pyrimidine (6). In some embodiments, a catalytic amount of Cu (I) salt is between 0.003 and 0.006 equivalents. In other embodiments, it is between 0.004 and 0.006 equivalents. In other embodiments it is 0.005 equivalents.

A suitable Pd catalyst is, for example, $PdCl_2(PPh_3)_2$. Other suitable Pd catalyst include $Pd(OAc)_2$, $Pd(PPh_3)_4$, $PdCl_2(dppf)$, $Pd(dppe)Cl$ and $Pd(dppp)Cl_2$.

An appropriate amount of a suitable Pd catalyst is a catalytic amount. A catalytic amount of a Pd catalyst is, for example, between 0 and 0.2 equivalents of Pd per each equivalent of intermediate (6). In some embodiments, a catalytic amount is between 0 and 0.1 equivalents. In still other embodiments, it is between 0 and 0.01 equivalents. In still other embodiments, it is between 0.0010 and 0.0040 equivalents of Pd per each equivalent of intermediate pyrimidine (6). In another embodiment, a catalytic amount is between 0.0015 and 0.0030 equivalents. In other embodiments it is between 0.0020 and 0.0030 equivalents. In still other embodiments, it is 0.0025 equivalents.

A suitable solvent in which the intermediate pyrimidine (7) in carried to the next step is, for example an ether. In one embodiment, the ether is methyl-tert-butyl ether. In other embodiments, the suitable solvent is, for example, Hunig's base, $Et_2NH$, $iPr_2NH$, piperidine, pyrrolidine, THF, Toluene, $CH_2Cl_2$, $CH_3CN$, DMF, DMSO or similar solvents.

In one embodiment, the intermediate pyrimidine (6) is reacted with ethynyltrimethylsilane in methyl-tert-butyl ether in the presence of trimethylamine, $Pd(PPh_3)_2Cl_2$ catalyst and CuI.

For step c) of any of the above processes towards the synthesis of a compound of Formula II, a compound of Formula III, a compound of Formula IV, a compound of Formula V, a compound of Formula VI, a compound of Formula VII, a compound of Formula IA, a compound of Formula IB, a compound of Formula IC or a compound of Formula ID and step c) for the preparation of the compound of formula (2) described in the $10^{th}$, $11^{th}$, $12^{th}$, $22^{nd}$, $23^{rd}$, $36^{th}$, $37^{th}$ and $38^{th}$ specific embodiments described above:

The de-silylation may carried out with a suitable fluoride reactant, a suitable acid or a suitable base.

A suitable fluoride reactant is, for example, KF, TBAF, CsF or NaF, among others. In some embodiments, a suitable fluoride reactant is KF.

A suitable acid is, for example, HCl, HBr, $MeSO_3H$, HF, or similar aqueous acids.

A suitable base is, for example, MeONa, MeOK, $MeOCs$, $K_2CO_3$, $Na_2CO_3$, $Cs_2CO_3$, or similar bases.

De-silylation reactions are very common and many conditions are available in the literature to carry it out. Therefore, many other fluoride reactants, acids and bases could be used.

An appropriate amount of a suitable fluoride reactant, suitable acid or suitable base is a catalytic amount. A catalytic amount of the suitable fluoride reactant, suitable acid or suitable base is, for example, less than one equivalent of the suitable fluoride reactant, suitable acid or suitable base per each equivalent of intermediate (7). In one embodiment, a catalytic amount is between 0.01 equivalents and 1. In other embodiments, it is between 0.01 and 0.75. In other embodiments, it is between 0.01 and 0.5. In other embodiments, it is between 0.01 and 0.25. In still other embodiments, it is between 0.01 and 0.1. In still other embodiments, it is between 0.01 and 0.05. In another embodiment, it is between 0.015 and 0.03. In still other embodiments, it is between 0.015 and 0.025. In other embodiments it is 0.02 equivalents.

A suitable solvent is, for example MeOH, THF, $CH_3CN$, EtOAc, $CH_2Cl_2$, $CHCl_3$, or many others, depending on the fluoride reactant, acid or base used. In one embodiment, the suitable solvent is MeOH.

A suitable temperature is between 15° C. and 35° C. In one embodiment, a suitable temperature is between 15° C. and 30° C. In other embodiments, it is between 18° C. and 30° C.

For step d) of any of the above processes towards the synthesis of a compound of Formula II, a compound of Formula III, a compound of Formula IV, a compound of Formula V, a compound of Formula VI, a compound of Formula VII, a compound of Formula IA, a compound of Formula IB, a compound of Formula IC or a compound of Formula ID and the reaction step for the preparation of the compound of formula (1) described in the $11^{th}$, $12^{th}$, $23^{rd}$, $37^{th}$ and $38^{th}$ specific embodiment:

A suitable equivalent reagent to oxalyl chloride is, for instance thionyl chloride or 1-Ethyl-3-(3-dimethylaminopropyl)carbodiimide (EDAC).

An appropriate amount of oxalyl chloride or equivalent reagent is at least one equivalent of oxalyl chloride per equivalent of carboxylic acid (8) or (8'). In some embodiments, an appropriate amount is between 1 and 3 equivalents. In other embodiments, an appropriate amount is between 1 and 2 equivalents. In still other embodiments, an appropriate amount is between 1 and 1.5 equivalents. In yet other embodiments, an appropriate amount is between 1.1 and 1.3 equivalents. In yet other embodiments, an appropriate amount is 1.1 equivalents or 1.2 equivalents.

A suitable aprotic organic solvent is, for instance toluene. Other suitable solvents are, for example methylene chloride or tetrahydrofuran.

A suitable catalyst is DMF.

An appropriate amount of the suitable catalyst is a catalytic amount, i.e., less than one equivalent of catalyst per each equivalent of starting material (8) or starting material (8'). In some embodiments, an appropriate amount is between 0.01 and 0.09 equivalents. In other embodiments it is between 0.01 and 0.07 equivalents. In still other embodiments, it is between 0.02 and 0.07 equivalents. In still other embodiments it is between 0.04 and 0.06 equivalents. In yet other embodiments, it is 0.05 equivalents.

A suitable temperature for the reaction of starting material (8) or starting material (8') with oxalyl chloride or thionyl chloride is a temperature between 40° C. and 95° C. In some embodiments, it is between 40° C. and 80° C. In other embodiments it is between 40° C. and 55° C. In some embodiments, a suitable temperature is between 45° C. and 55° C.

In other embodiments, it is a temperature of between 45° C. and 50° C. In other embodiments, it is a temperature of between 50° C. and 60° C.

A suitable temperature for the reaction of starting material (8) or starting material (8') with EDAC is a temperature between −10° C. and 25° C. In some embodiments, a suitable temperature is between −10° C. and 20° C. In some embodiments, a suitable temperature is between −10° C. and 0° C. In some embodiments, a suitable temperature is between −10° C. and −5° C.

In some embodiments, the N,O-dimethylhydroxylamine is used as the HCl or hydrochloride salt.

An appropriate amount of N,O-dimethylhydroxylamine hydrochloride is at least one equivalent of N,O-dimethylhydroxylamine hydrochloride per each equivalent of starting material (8) or starting material (8'). In other embodiments, an appropriate amount of N,O-dimethylhydroxylamine hydrochloride is between 1 equivalent and 2 equivalents per each equivalent of starting material (8) or starting material (8'). In other embodiments, it is between 1 equivalent and 1.5 equivalents. In other embodiments, it is between 1 equivalent and 1.2 equivalents. In other embodiments, it is between 1.1 equivalents and 1.2 equivalents.

A suitable base is, for instance, $K_2CO_3$ or NaOH. Other suitable bases are, for example, $NaHCO_3$, $KHCO_3$, $Et_3N$, or Hunig's base.

An appropriate excess of said suitable base is at least 2 equivalents of base per equivalent of N,O-dimethylhydroxylamine hydrochloride used. In some embodiments, an appropriate amount is between 2 and 5 equivalents of base per equivalent of N, O-dimethylhydroxylamine hydrochloride. In other embodiments, it is 2 to 3 equivalents. In still other embodiments, it is between 2 and 4 equivalents.

A suitable solvent for the water/aprotic solvent mixture is, for instance, dichloromethane (DCM). Other suitable solvents are, for example, ethyl acetate, tetrahydrofuran and 2-methyltetrahydrofuran.

For step iv) towards the synthesis of a compound of Formula III, a compound of Formula IV, a compound of Formula VI, a compound of Formula VII, a compound of Formula IA, a compound of Formula IB, a compound of Formula IC or a compound of Formula ID and step iv) in the $4^{th}$ to $12^{th}$ and $16^{th}$ to $38^{th}$ specific embodiments described above:

The reaction can be carried out under suitable acidic, basic or neutral conditions.

A suitable aqueous acid is, for example, HCl. Other acids that could be used include, for instance, methylsulfonic acid ($MeSO_3H$) or HBr.

A suitable reagent that could be used under basic conditions is, for example, MeSNa.

A suitable reagent that could be used under neutral and anhydrous conditions is, for example, $BBr_3$.

De-methylation reactions such as step iv) are common and many different conditions may be found in the literature.

An appropriate amount of acid is between 3 and 6 equivalents of acid per equivalent of compound of Formula II or compound of Formula V. In some embodiments, an appropriate amount is between 4 and 6 equivalents. In other embodiments, it is between 4.5 equivalents and 6 equivalents. In still other embodiments, it is 4.90 to 5 equivalents. HCl can be provided, for instance, in the form of concentrated HCl (e.g., 37 wt % HCl).

A suitable protic solvent is, for instance, MeOH. Other suitable protic solvents are EtOH and iPrOH.

A suitable aprotic solvent is for example an ether or THF.

A suitable temperature is between 50° C. and 70° C. In some embodiments, a suitable temperature is between 55° C. and 65° C. In still other embodiments, a suitable temperature is between 60° C. and 65° C. In still other embodiments, a suitable temperature is between 62° C. and 65° C.

For step v) towards the synthesis of a compound of Formula III, a compound of Formula IV, a compound of Formula VI, a compound of Formula VII, a compound of Formula IA, a compound of Formula IB, a compound of Formula IC or a compound of Formula ID and step v) in the $6^{th}$ to $12^{th}$ and $18^{th}$ to $38^{th}$ specific embodiments described above:

An appropriate amount of $POCl_3$ is at least two equivalents of $POCl_3$ per each equivalent of intermediate (9) or intermediate (9') used. In some embodiments, an appropriate amount of $POCl_3$ is at least 4 equivalents. In some embodiments, an appropriate amount is at least 3 equivalents. In some embodiments, an appropriate amount is at least 2 equivalents. In some embodiments, an appropriate amount is at least 1 equivalent. In still other embodiments, an appropriate amount is between 1 and 4 equivalents of $POCl_3$ per each equivalent of intermediate (9) or intermediate (9').

A suitable temperature is between 50° C. and 90° C. In some embodiments, a suitable temperature is between 60° C. and 90° C. In some embodiments, a suitable temperature is between 65° C. and 90° C. In other embodiments, a suitable temperature is between 70° C. and 90° C. In still other embodiments, a suitable temperature is between 75° C. and 90° C. In yet other embodiments, a suitable temperature is between 75° C. and 85° C. In other embodiments, a suitable temperature is between 75° C. and 80° C.

A suitable aprotic organic solvent is, for instance, acetonitrile (CNMe). The reaction can also be carried out in neat $POCl_3$, in the absence of any solvents.

A suitable optional base is, for instance, N,N-dimethylaniline. The reaction also works in the absence of a base.

An appropriate amount of a suitable base, when one is used, is between 0.2 and 2 equivalents of base per each equivalent of intermediate (9) or intermediate (9') used. In some embodiments, an appropriate amount of base is between 1.3 and 1.6 equivalents. In some embodiments, an appropriate amount of base is between 1.2 and 1.8 equivalents. In other embodiments, it is 1 equivalent.

For step vi) towards the synthesis of a compound of Formula IV, a compound of Formula VII, a compound of Formula IA, a compound of Formula IB, a compound of Formula IC or a compound of Formula ID and step vi) in the $8^{th}$ to $12^{th}$ and $20^{th}$ to $38^{th}$ specific embodiments described above:

An appropriate amount of an amine (10), or an amine (13), or an amine malic acid salt (14) or an amine malic acid salt (18) or an amine (15A) or its corresponding HCl salt (15), or an amine (19A) or its corresponding HCl salt (19) is at least one equivalent of the amine or HCl or malic acid salt per each equivalent of compound of Formula VI or compound of Formula III. In some embodiments, an excess of amine may be used. In some embodiments, an amount between 1 and 5 equivalents of the amine can be used. In other embodiments, the appropriate amount is between 1 and 4 equivalents. In other embodiments, it is between 1 and 3 equivalents. In still other embodiments, it is between 1 and 2 equivalents. In still other embodiments it is between 1.1 and 1.5 equivalents. In yet other embodiments it is 1.1 to 1.3 equivalents.

A suitable optional base is, for instance, Hunig's base. Other suitable optional bases are, for example, $Et_3N$, $NaHCO_3$, and $KHCO_3$. An appropriate amount of an amine (10), or an amine (13), or an amine (15A) or an amine (19A) themselves may also be used as the base when they are in used in excess.

An appropriate amount of a suitable optional base is at least one equivalent of optional base per each equivalent of intermediate of Formula VI or intermediate of Formula III. In some embodiments, an appropriate amount is 2 equivalents.

A suitable solvent is dimethylsulfoxide (DMSO). Other suitable solvents are, for instance, N,N-dimethylformamide (DMF), N,N-dimethylacetamide (DMA), and tert-butanol (t-BuOH).

A suitable temperature is between 90° C. and 135° C. In some embodiments, a suitable temperature is between 120° C. and 130° C. In other embodiments, a suitable temperature is between 125° C. and 130° C. In other embodiments, a suitable temperature is between 90° C. and 105° C. In still other embodiments, it is between 95° C. and 104° C.

Novel intermediates that are useful in the processes described herein are also disclosed.

In one embodiment, the present invention is directed to a compound of formula (3) or (4). In one embodiment, for compound of formula (3) or (4), $R^1$ is a 5-membered heteroaryl ring. In another embodiment, for compound of formula (3) or (4), $R^1$ is an unsubstituted 5-membered heteroaryl ring containing up to 2 ring heteroatoms selected from the group consisting of N and O.

In another embodiment, the present invention is directed to a compound of formula (3') or (4').

In yet another embodiment, the present invention is directed to a compound of formula (14), (18), (15), (19), (20) or (21).

In one aspect, the present invention provides crystalline Form A of the compound of Formula IA. Form A can be prepared according the process described herein, for example, the process of the 13$^{th}$ specific embodiment, the first, second, third, fourth, fifth or sixth process for making the compound of Formula IA described above.

Form A is characterized by X-ray powder diffraction (XRPD) analysis. In one embodiment, Form A of the compound of Formula IA has XRPD pattern substantially similar to those shown in FIG. 1. In one embodiment, Form A has XRPD pattern as shown in FIG. 1. In another embodiment, Form A has XRPD peaks as indicated in the table below:

| Angle | d Value | intensity | Rel. Intensity |
| --- | --- | --- | --- |
| 4.218° | 20.92949 Å | 1531 | 34.8% |
| 9.082° | 9.72888 Å | 2846 | 64.7% |
| 9.787° | 9.02964 Å | 3669 | 83.4% |
| 10.885° | 8.12181 Å | 14.8 | 0.3% |
| 12.198° | 7.24980 Å | 65.7 | 1.5% |
| 13.758° | 6.43115 Å | 288 | 6.5% |
| 15.443° | 5.73323 Å | 379 | 8.6% |
| 16.880° | 5.24808 Å | 568 | 12.9% |
| 17.222° | 5.14486 Å | 750 | 17.0% |
| 17.743° | 4.99495 Å | 4401 | 100.0% |
| 18.213° | 4.86700 Å | 1862 | 42.3% |
| 18.923° | 4.68599 Å | 277 | 5.3% |
| 19.646° | 4.51517 Å | 282 | 6.4% |
| 20.726° | 4.28219 Å | 34.1 | 0.8% |
| 20.969° | 4.23314 Å | 16.4 | 0.4% |
| 21.816° | 4.07062 Å | 54.8 | 1.2% |
| 23.126° | 3.84299 Å | 106 | 2.4% |
| 24.585° | 3.61801 Å | 185 | 4.2% |
| 25.495° | 3.49102 Å | 114 | 2.5% |
| 26.106° | 3.41067 Å | 99.3 | 2.3% |
| 27.050° | 3.29372 Å | 112 | 2.5% |
| 27.499° | 3.24097 Å | 734 | 16.7% |
| 28.082° | 3.17498 Å | 233 | 5.3% |
| 28.827° | 3.09457 Å | 85.8 | 2.0% |
| 29.767° | 2.99895 Å | 243 | 5.5% |
| 30.683° | 2.91146 Å | 55.1 | 1.3% |
| 31.156° | 2.86841 Å | 113 | 2.6% |
| 31.871° | 2.80565 Å | 60.0 | 1.4% |
| 32.981° | 2.71369 Å | 138 | 3.1% |
| 35.312° | 2.53969 Å | 44.2 | 1.0% |
| 36.005° | 2.49240 Å | 1225 | 27.8% |
| 39.044° | 2.30515 Å | 270 | 6.1% |

In another embodiment, Form A is characterized as having one, two, three, four, five, six, seven or eight major peaks in XRPD pattern selected from 4.2, 9.1, 9.8, 17.2, 17.7, 18.2, 27.5, and 36.0 degree 2θ angles. In one embodiment, Form A is characterized as having one, two, three, four or five major XRPD peaks selected from 4.2, 9.1, 9.8, 17.7, 18.2, and 36.0 degree 2θ angles. In another embodiment, Form A has major XRPD peaks at 9.1, 9.8, 17.7, and 18.2 degree 2θ angles. In yet another embodiment, Form A has major XRPD peaks at 4.2, 9.1, 9.8, 17.7, 18.2, and 36.0 degree 2θ angles. In another embodiment, Form A has major XRPD peaks at 4.2, 9.1, 9.8, 17.2, 17.7, 18.2, 27.5, and 36.0 degree 2θ angles. It is to be understood that a specified 2θ angle means the specified value±0.1°.

As used herein, the term "major peaks" refers to an XRPD peak with relative intensity of greater than 10%. Relative intensity is calculated as a ratio of the peak intensity of the peak of interest versus the peak intensity of the largest peak.

Form A can also be characterized by differential scanning calorimetry (DSC). In one embodiment, Form A has an endothermic onset (i.e., a melting point) at a temperature between 140° C. and 180° C., between 155° C. and 170° C., between 160° C. and 170° C., between 160° C. and 165° C., between 162° C. and 164° C., or between 162.5° C. and 163.5° C. In one embodiment, the endothermic onset is at 163.1° C. It is to be understood that a specified temperature means the specified value±0.5° C.

In some embodiment, Form A is at least 70%, 80%, 90%, 95%, 98%, 99%, 99.5%, or 99.9% pure. The purity of Form A is determined by diving the weight of Form A of the compound of Formula IA in a composition comprising the compound of Formula IA over the total weight of the compound of Formula IA in the composition.

In some embodiments, a composition of the compound of Formula IA has at least 70%, 80%, 90%, 95%, 98%, 99%, 99.5%, or 99.9% by weight of the compound is the crystalline Form A of the compound.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), "contain" (and any form contain, such as "contains" and "containing"), and any other grammatical variant thereof, are open-ended linking verbs. As a result, a method that "comprises", "has", "includes" or "contains" one or more steps possesses those one or more steps, but is not limited to possessing only those one or more steps. Likewise, a step of a method that "comprises", "has", "includes" or "contains" one or more features possesses those one or more features, but is not limited to possessing only those one or more features.

All publications cited in this specification are herein incorporated by reference as if each individual publication were specifically and individually indicated to be incorporated by reference herein as though fully set forth.

Where one or more ranges are referred to throughout this specification, each range is intended to be a shorthand format for presenting information, where the range is understood to encompass each discrete point within the range as if the same were fully set forth herein.

EXAMPLES

The following preparative examples are set forth in order that this invention is more fully understood. These examples are for the purpose of illustration only and are not to be construed as limiting the scope of the invention in any way.

In-Process Control Methods

HPLC Analysis Method a (TFA Modified Mobile Phase)

Equipment:
- A. HPLC analyses were conducted using an Agilent 1100/1200 series HPLC system consisting of pump, ChemStation UV VWD or DAD detector, auto injector, and column heater, or equivalent. ChemStation Software installed on GX270 or equivalent. Column was HALO C18 150×4.6 mm.
- B. Column: HALO C18 150×4.6 mm 2.7 micron or equivalent
- C. Auto-sampler vials, silicon/Teflon septa, 12×32 mm
- D. 100-mL class A volumetric flasks
- E. Weighing funnels
- F. Spatulas
- G. Disposable glass Pasteur pipettes
- H. Balance capable of accurately weighing 0.01 mg
- I. 2×2-L solvent reservoir Reagents:
- A. Water, HPLC grade or equivalent
- B. Acetoniltrile (ACN), HPLC grade, or equivalent
- C. Trifluoroacetic acid (TFA) HPLC grade or equivalent
- D. Intermediate test sample.
- E. Intermediate authentic materials or reference standard if available.

Solvent and Diluent:
- A. Solvent A: 0.1% TFA in water (i.e. 1 mL in 1 L of water)
- B. Solvent B: 0.1% TFA in acetonitrile (i.e. 1 mL in 1 L of ACN)
- C. Diluent: acetonitrile/water Flow Rate: 1.0 mL/min Column Temperature: 40° C.

Time Table:

| Time (minute) | % Solvent A | % Solvent B |
|---|---|---|
| 0 | 85 | 15 |
| 10 | 5 | 95 |
| 15 | 5 | 95 |

Retention Times of Selected Compounds:

| Compound | Approximate Retention Time (Min) |
|---|---|
| (8') | 1.8 |
| Piperidine amide | 4.9 |
| (1') | 3.0 |
| (5) | 7.0 |
| (6) | 6.5 |
| (7) | 9.5 |
| (2) | 5.4 |
| Formula V | 8.7 |
| (9') | 6.9 |
| Formula VI | 9.3 |
| Formula IA | 8.8 |
| Formula ID | 6.9 |

HPLC Analysis Method B (Neutral Mobile Phase)

Equipment:
- A. HPLC analyses were conducted using an Agilent 1100/1200 series HPLC system consisting of pump, ChemStation UV VWD or DAD detector, auto injector, and column heater, or equivalent. ChemStation Software installed on GX270 or equivalent. Column was HALO C18 150×4.6 mm.
- B. Column: HALO C18 150×4.6 mm 2.7 micron or equivalent
- C. Auto-sampler vials, silicon/Teflon septa, 12×32 mm
- D. 100-mL class A volumetric flasks
- E. Weighing funnels
- F. Spatulas
- G. Disposable glass Pasteur pipettes
- H. Balance capable of accurately weighing 0.01 mg
- I. 2×2-L solvent reservoir Reagents:
- A. Water, HPLC grade or equivalent
- B. Acetoniltrile (ACN), HPLC grade, or equivalent
- C. Intermediate test sample.
- D. Intermediate authentic materials or reference standard if available.

Solvent and Diluent:
- A. Solvent A: Water
- B. Solvent B: Acetonitrile
- C. Diluent: acetonitrile/water Flow Rate: 1.0 mL/min Column Temperature: 40° C.

Time Table:

| Time (minute) | % Solvent A | % Solvent B |
|---|---|---|
| 0 | 85 | 15 |
| 10 | 5 | 95 |
| 15 | 5 | 95 |

Retention Times of Selected Compounds:

| Compound | Approximate Retention Time (Min) |
|---|---|
| (2) | 5.4 |
| (3') | 7.4 |
| (4') | 5.9 |
| (9') | 8.7 |

Nuclear Magnetic Resonance Spectroscopy $^1$H NMR spectra of all compounds were recorded on a BRUKER NMR spectrometer operating at 500 MHz at room temperature. Samples dissolved in CDCl$_3$ were referenced relative to residual solvent peak at 7.27 ppm. Samples dissolved in DMSO-d$_6$ were referenced relative to the residual solvent peak at 2.50 ppm. The resulting FIDs were transferred to a PC and processed using ACD/Labs NMR processing software.

X-Ray Powder Diffraction (XRPD):

X-Ray Powder Diffraction traces were obtained using a D8 Advance, Bruker apparatus; using one of two Methods: Scan 5-45° 2-theta, 0.02° step size, 1 sec per step; or Scan 3-40° 2-theta, 0.037° step size, 1.5 sec per step Example 1: Preparation of Compounds of Formula VI Step d): Coupling of Compound (8') and N,O-Dimethylhydroxylamine to provide N-methoxy-N-methylisoxazole-3-carboxamide (1')

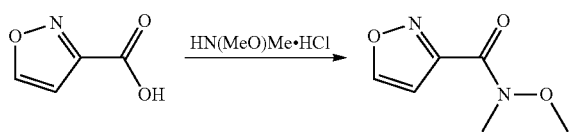

$C_4H_3NO_3$
MW: 113.07
(8')

$C_6H_8N_2O_3$
MW: 156.14
(1')

Isooxazole-3-carboxylic acid ((8'), 92 wt % assay based on $^1$H-NMR, 3.86 kg, 34.1 mol, 1.0 equiv), toluene (19.3 L) and DMF (0.131 L, 1.69 mol, 0.05 equiv) were mixed in a 30 L jacketed reaction vessel equipped with a nitrogen inlet-outlet, overhead stirrer, a thermocouple and an addition funnel. The resulting slurry was heated to 45 to 55° C. Oxalyl chloride (4.80 kg, 37.8 mol, 1.11 equiv) was charged via the addition funnel over the course of 4 hours 30 minutes, while maintaining the reaction temperature between 45 to 55° C. Vigorous gas evolution was observed. A brown mixture was obtained after the addition. The brown mixture was held at 45 to 55° C. for 30 minutes, then heated to 85 to 95° C. and stirred at 85 to 95° C. for 1 hour. During heating, the brown mixture turned into a black mixture. The black mixture was cooled to 20 to 25° C., over 4 hours and held at 20 to 25° C. for a minimum of 16 hours. The reaction was monitored by quenching a portion of the reaction mixture into piperidine and monitoring the formation of the piperidine amide by HPLC ((8'): piperidine amide area:area % was <1.9). After the reaction was complete by HPLC the dark mixture was in-line filtered via gas a dispersion tube (coarse frit) into a 20 L rotavapor flask. Toluene (3.9 L) was used to rinse the reactor and the rinse was in-line filtered into the 20 L rotavapor flask. The filtered reaction mixture was concentrated under reduced pressure until no more distillate was seen coming off.

Separately, potassium carbonate (7.06 kg, 51.1 mol, 1.5 equiv) and water (31 L) were stirred in a 100 L jacketed reactor. The reaction solution was cooled to −10 to 10° C. N,O-dimethylhydroxylamine hydrochloride (3.93 kg, 40.3 mol, 1.18 equiv) was charged to the reactor followed by dichloromethane (39 L). The reaction mixture was cooled to −10 to 0° C. The acyl chloride intermediate formed above (4.4 kg) was charged to a 100 L jacketed reactor containing N,O-dimethylhydroxylamine in dichloromethane, with stirring rate set at 210 RPM, while maintaining the reaction temperature between −10 to 0° C., over 30 minutes. The addition was a little exothermic, and a brown mixture was obtained after the addition. The reaction mixture was stirred at −10 to 0° C. for 20 minutes, then warmed to 15 to 25° C. and stirred for 10 minutes at this temperature. The layers were separated. The bottom organic layer was collected, and the top aqueous layer was extracted with dichloromethane (7.7 L). The combined organic layers were transferred to a 100 L jacketed reactor and washed with a 15 wt % aqueous sodium chloride solution (11.6 L). The layers were separated. The bottom organic layer was collected, and the top aqueous layer was extracted with dichloromethane (3.9 L). The combined organic layers were concentrated under reduced pressure until no more distillate was seen coming off. Tetrahydrofuran (7.7 L) was charged to this dark oil and the resulting mixture concentrated under reduced pressure to furnish intermediate (1') as a dark oil (4.6 kg, 83% corrected yield for THF, 4 wt % THF content by $^1$H-NMR, 0.01 wt % water content by Karl-Fisher (KF) analysis, 98.9% pure by HPLC). $^1$H-NMR (500 MHz, CDCl$_3$) δ ppm 8.48 (s, 1H); 6.71 (s, 1H); 3.78 (s, 3H); 3.38 (s, 3H).

Step a): Substitution of Compound (5) with Methoxide to Provide 2-bromo-5-fluoro-4-methoxypyrimidine (6)

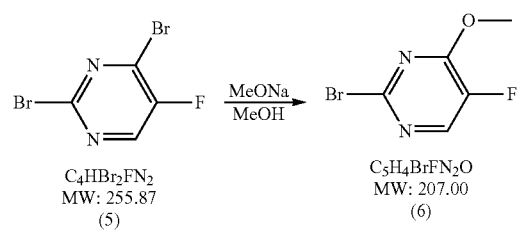

$C_4HBr_2FN_2$
MW: 255.87
(5)

$C_5H_4BrFN_2O$
MW: 207.00
(6)

2,4-Dibromo-5-fluoropyrimidine ((5), 6.42 kg, 25.1 mol, 1.0 equiv) and methanol (35.3 L) were mixed in a 30 L jacketed reaction vessel equipped with a nitrogen inlet-outlet, overhead stirrer, a thermocouple and an addition funnel. The reaction solution was cooled to −15 to −5° C. and a suspension was obtained. Sodium methoxide, 5.4 M solution in methanol (4.75 L, 25.7 mol, 1.02 equiv) was charged over 3 h via an addition funnel while maintaining the reaction temperature at −15 to −5° C. After the addition, the mixture was stirred at −15 to −5° C. for 30 minutes. The reaction was complete by HPLC method A ((5):(6) area:area %=not detected). 2 N HCl (0.26 L, 0.52 mol, 0.02 equiv) was charged over 2 min, while maintaining the temperature at −15 to −5° C. Water (12.8 L) was then charged over 2 minutes, while maintaining the temperature at −15 to 25° C. The pH of the reaction mixture was ~3-4 by pH paper. The reaction mixture was concentrated under reduced pressure until most methanol had distilled out.

Methyl t-butyl ether (51.4 L) was charged to the concentrated reaction mixture and the layers were allowed to separate over 1 hour. The organic layer was filtered via gas dispersion tube (coarse frit) and concentrated under reduced pressure to a volume of 19.3 L. Water was azeotropically removed under reduced pressure via continuously feeding methyl t-butyl ether (24.0 L). The final volume was 18.0 L and the azeotropic removal of water was complete by KF analysis (0.24 wt % water content, acceptance criteria: <0.4 wt % water content). Intermediate (6) in methyl t-butyl ether was obtained as a light brown solution and used directly in the next step. $^1$H-NMR (500 MHz, CDCl$_3$) δ ppm 8.08 (s, 1H); 4.04 (s, 3H).

Step b): Coupling of Compound (6) and Ethynyltrimethylsilane to Provide 5-fluoro-4-methoxy-2-((trimethylsilyl)ethynyl)pyrimidine (7)

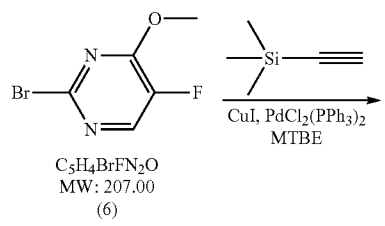

C$_5$H$_4$BrFN$_2$O
MW: 207.00
(6)

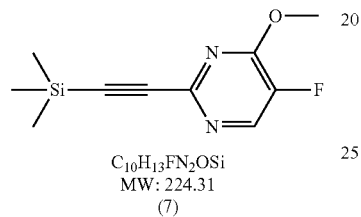

C$_{10}$H$_{13}$FN$_2$OSi
MW: 224.31
(7)

The above solution of intermediate (6) in methyl t-butyl ether (18.0 L, 25.1 mol, 1.0 equiv) was charged to the 100 L jacketed reaction vessel and methyl t-butyl ether (16.0 L) was added to bring the volume to 34.0 L. Triethylamine (5.1 kg, 50.4 mol, 2.0 equiv) was then charged to the 100 L jacketed reaction vessel. The reaction mixture was deoxygenated via 4 to 5 vacuum/nitrogen cycles at 15 to 30° C. (400 mbar for 5 minutes followed by nitrogen fill). Copper iodide (24.0 g, 0.126 mol, 0.005 equiv) and bis(triphenylphosphine)palladium(II) dichloride (44.2 g, 0.063 mol, 0.0025 equiv) were charged to the reaction mixture. The reaction mixture was deoxygenated via 2 to 3 vacuum/nitrogen cycles at 15 to 30° C. (400 mbar for 5 minutes followed by nitrogen fill). Ethynyltrimethylsilane (3.0 kg, 30.5 mol, 1.2 equiv) was charged via an addition funnel over the course of 2.5 hours, while maintaining the reaction temperature between 18 to 30° C. The reaction mixture was stirred at 20 to 30° C. for 16 h, and a suspension was obtained. The reaction was complete by HPLC method A ((6):(7) area:area %=not detected).

The reaction mixture was cooled to 5 to 15° C. Then 2 N HCl (16.0 L, 32.0 mol, 1.3 equiv) was charged over 4 minutes, while maintaining the reaction temperature below 25° C. (batch temperature increased from 6° C. to 22° C.). The layers were allowed to separate over 20 min. The pH of the aqueous layer was ~1-2 by pH paper and it was discarded. SiliaMetSDimercaptotriazine (411 g, 0.21 mol, 0.008 equiv) was charged to the reaction mixture. The reaction mixture was heated to 45 to 55° C. and held for 2 hours at 45 to 55° C., then cooled to 20 to 25° C. The reaction mixture was filtered through Hyflo SuperCel (0.66 kg) and methyl t-butyl ether (12.9 L) was used to rinse the 100 L jacketed reaction vessel and the rinse transferred to the filter to wash the cake. The filtrate was concentrated under reduced pressure to a volume of 19.2 L. Methyl t-butyl ether was solvent exchanged to methanol under reduced pressure via continuously feeding methanol (25.6 L) and the final volume after solvent exchange was 19.2 L. Intermediate (7) in methanol was obtained as a light brown solution and used directly in the next step. $^1$H-NMR (500 MHz, CDCl$_3$) δ ppm 8.09 (s, 1H); 3.94 (s, 3H); 0.12 (s, 9H).

Step c): De-Silylation of Compound (7) to Provide 2-ethynyl-5-fluoro-4-methoxypyrimidine (2)

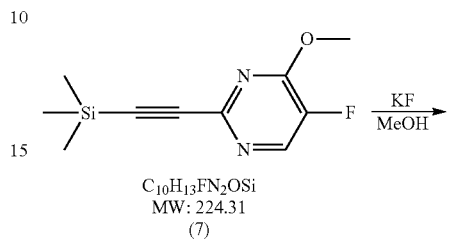

C$_{10}$H$_{13}$FN$_2$OSi
MW: 224.31
(7)

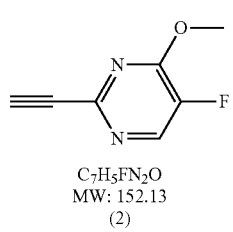

C$_7$H$_5$FN$_2$O
MW: 152.13
(2)

The above intermediate (7) solution in methanol (19.2 L, 25.1 mol, 1.0 equiv) was charged to a 100 L jacketed reaction vessel and methanol (9.0 L) was added to bring the volume to 28.2 L. Potassium fluoride (29.5 g, 0.508 mol, 0.02 equiv) was charged to the reaction mixture. The reaction mixture was stirred at 18 to 30° C. for 1 hour, at which point the reaction was complete by HPLC Method A ((7):(2) area/area %=not detected). Water (22.5 L) was then charged to the reaction mixture over 10 min, while maintaining the temperature at 15 to 30° C. The reaction mixture was concentrated under reduced pressure until most methanol distilled out to give a slurry in water.

Methyl t-butyl ether (32.1 L) was charged to the slurry and the layers were allowed to separate over 30 minutes. The top organic layer was collected, and the bottom aqueous layer was extracted with methyl t-butyl ether (12.8 L). The combined organic layers were concentrated under reduced pressure to a volume of 19.3 L. The concentrate was filtered through a silica pad (960 g) and the silica pad was rinsed with additional methyl t-butyl ether (12.8 L). The filtrate was collected and concentrated under reduced pressure to a volume of 19.3 L. Methyl t-butyl ether was solvent exchanged to heptane under reduced pressure via continuously feeding heptane (33.4 L). The final volume after solvent exchange was 22.5 L. The resulting slurry was cooled to 0 to 5° C., over 30 minutes and held at 0 to 5° C. for 1 hour. The slurry was filtered, and the filter cake was washed with heptane (6.4 L). The wet cake was dried under vacuum at 20 to 25° C., for 4 hours until constant weight to furnish intermediate (2) as a light brown solid (3.33 kg, 88% yield from (5) over 3 steps). $^1$H-NMR (500 MHz, CDCl$_3$) δ ppm 8.28 (d, J=2.44 Hz, 1H,); 4.11 (s, 3H); 3.06 (s, 1H).

Steps i) and ii): Coupling of Compounds (2) and (1') to Provide (E)-3-(5-fluoro-4-methoxypyrimidin-2-yl)-1-(isoxazol-3-yl)-3-(methoxy(methyl)amino)prop-2-en-1-one (4')

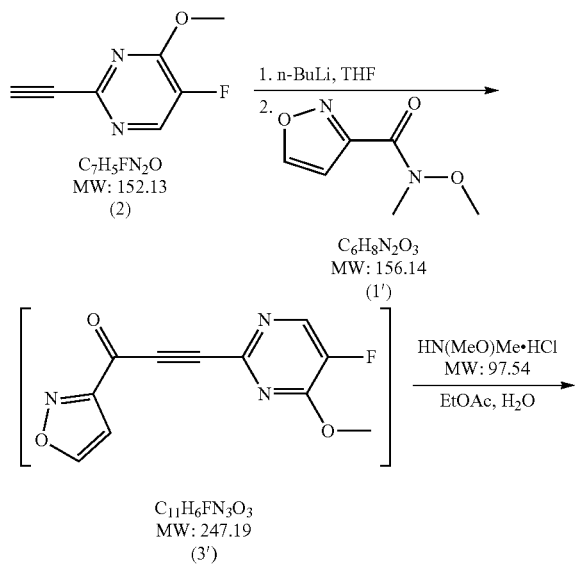

Compound (2) (1.826 kg, 12.0 mol, 1.0 equiv) and anhydrous THF (11.0 L) were mixed in a 50 L round bottom flask equipped with a mechanical stirrer and a thermocouple. The reaction solution was cooled to −78 to −60° C. n-Butyllithium, 2.5 M solution in hexanes (4.8 L, 12.0 mol, 1.0 equiv) was charged over 1 hour 30 minutes via cannula while maintaining the reaction temperature at −78 to −60° C., and a brown suspension was obtained. After the addition, the suspension was stirred at below −60° C. for 30 minutes. Then compound (1') (2.06 kg, 95 wt %, 12.6 mol, 1.05 equiv) was charged over 40 minutes, while maintaining the reaction temperature below −55° C. (batch temperature increased from −73° C. to −60° C.). The reaction mixture was stirred at −65 to −55° C. for 1 hour and then warmed to −50 to −45° C. and held at −50 to −45° C. for 30 minutes, and a dark solution was obtained.

Separately, N,O-Dimethylhydroxylamine hydrochloride (0.586 kg, 6.0 mol, 0.5 equiv) and 1 N HCl (9.6 L, 9.6 mol, 0.8 equiv) were mixed in a 100 L jacketed reaction vessel equipped with a nitrogen inlet-outlet, overhead stirrer, and a thermocouple. The reaction solution was cooled to 0 to 5° C. The above dark reaction solution from the 50 L round bottom flask was transferred to the 100 L jacketed reaction vessel over 15 minutes with vigorously mixing. Ethyl acetate (18.3 L) was used to rinse the 50 L round bottom flask and the rinse transferred to the 100 L jacketed reaction vessel. Saturated sodium bicarbonate solution (9.2 L) was charged to the 100 L jacketed reaction vessel to adjust the batch pH to ~7-8. After stirring for 2 hours at 15 to 25° C., the reaction was complete by HPLC Method B ((3'):(4') area:area %=not detected). The top ethyl acetate layer was collected and washed with 10 wt % sodium chloride solution (11.0 L). The organic layer was filtered via gas dispersion tube (coarse frit) and concentrated under reduced pressure to a volume of 9.1 L. Ethyl acetate was azeotropically removed under reduced pressure via continuously feeding methanol (18.3 L). The final volume after solvent exchange was 9.1 L and a slurry was obtained. The resulting slurry was cooled to 0 to 5° C. and stirred at 0 to 5° C. for 30 minutes. The resulting slurry was filtered, and the filter cake was washed with pre-cooled 0 to 5° C. methanol (2.7 L). The filter cake was dried under high vacuum at 35 to 45° C. for 8 hours until constant weight to furnish (4') as a light brown solid (2.73 kg, 74% yield, 99% pure by HPLC). $^1$H-NMR (500 MHz, CD$_3$OD) δ ppm 8.68 (d, J=1.53 Hz, 1H); 8.50 (d, J=3.05 Hz, 1H); 6.61 (d, J=1.68 Hz, 1H); 6.44 (s, 1H); 4.08 (s, 3H); 3.82 (s, 3H); 3.14 (s, 3H).

Step iii): Cyclization of Compound (4') and 2-fluorobenzylhydrazine to Provide 3-(3-(5-fluoro-4-methoxypyrimidin-2-yl)-1-(2-fluorobenzyl)-1H-pyrazol-5-yl)isoxazole (Formula V)

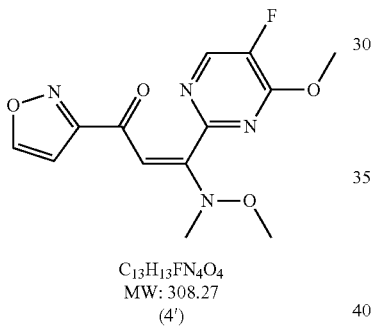

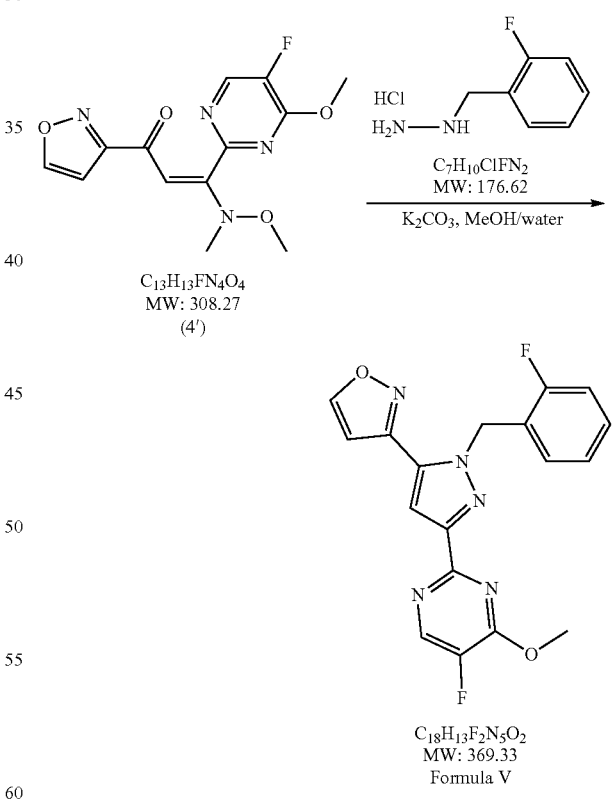

2-Fluorobenzylhydrazine hydrochloride (3.37 kg, 19.1 mol, 1.2 equiv) and methanol (9.8 L) were mixed in a 50 L round bottom flask equipped with an overhead stirrer and a thermocouple. The reaction mixture was stirred at 10 to 25° C. until most solids dissolved. Separately, potassium carbonate (1.32 kg, 9.6 mol, 0.6 equiv) was charged to a suitable reaction vessel and dissolved in water (3.4 L). The potassium carbonate solution was charged to the 50 L round bottom flask containing 2-fluorobenzylhydrazine hydrochloride solution between 10 to 25° C., over 5 minutes, and a slurry was obtained.

Separately, compound (4') (4.89 kg, 15.9 mol, 1.0 equiv) and methanol (24.5 L) were mixed in a 100 L jacketed reaction vessel equipped with a nitrogen inlet-outlet, an overhead stirrer, a thermocouple and an addition funnel. The above 2-fluorobenzylhydrazine in methanol slurry was transferred to the reaction mixture in the 100 L jacketed reaction vessel over 5 minutes, while maintaining the temperature at 15 to 30° C. After stirring for 10 hours at 20 to 25° C., a suspension was obtained. The reaction was complete by HPLC Method B ((4'):Formula V area:area %=not detected). Concentrated hydrochloric acid (1.31 L, 37 wt %, 15.9 mol, 1.0 equiv) was charged to the reaction mixture over 2 minutes, and the batch temperature increased from 21° C. to 29° C. The mixture was cooled to 20 to 25° C., over 30 minutes and stirred at 20 to 25° C. for 1 hour. Water (24.5 L) was charged via addition funnel over 30 minutes, while maintaining the temperature at 20 to 25° C. The resulting slurry was stirred at 20 to 25° C. for 30 minutes and filtered. The filter cake was washed with a mixture of methanol (14.7 L) and water (14.7 L). The filter cake was dried under high vacuum at 45 to 55° C. for 16 hours until constant weight to furnish Formula V as an off-white solid (5.83 kg, 99% yield, 99% pure by HPLC). $^1$H-NMR (500 MHz, CDCl$_3$) δ ppm 8.47 (d, J=1.68 Hz, 1H); 8.41 (d, J=2.59 Hz, 1H); 7.36 (s, 1H); 7.17-7.24 (m, 1H); 6.95-7.07 (m, 2H); 6.83-6.90 (m, 1H); 6.60 (d, J=1.68 Hz, 1H); 5.99 (s, 2H); 4.19 (s, 3H).

Step iiia) Naked Pyrazole Formation

Compound (4') (50.16 g, 163 mmol) was charged to a 3 L 4-neck flask fitted with an overhead stirrer and a thermocouple. Methanol (750 mL) and water (250 mL) were added and the mixture cooled to 10° C. Hydrazine hydrate (55 wt % in water) (23.7 g, 260 mmol, 1.6 eq) was added dropwise and the reaction allowed to warm to room temperature and stirred overnight. A further 250 mL of water was added dropwise and the resulting solids isolated by filtration and washed with 2×250 mL of a 3:1 MeOH:Water mixture. The solids were partially dried under vacuum on the filter and then in an oven at 35° C. under vacuum/nitrogen stream overnight to give Compound (24') as a pale-yellow solid, 38.50 g, 91%.

Step iiib): Alkylation of Naked Pyrazole

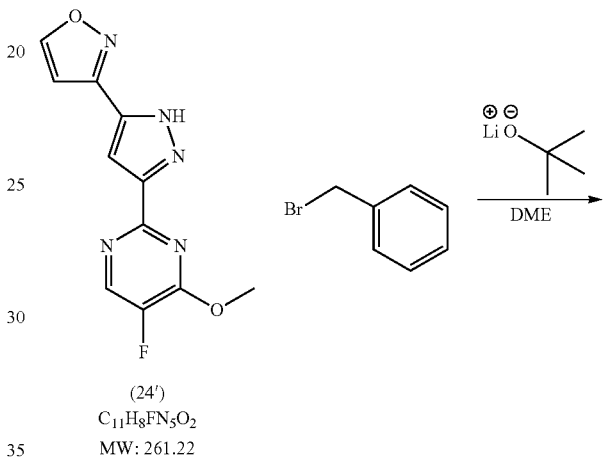

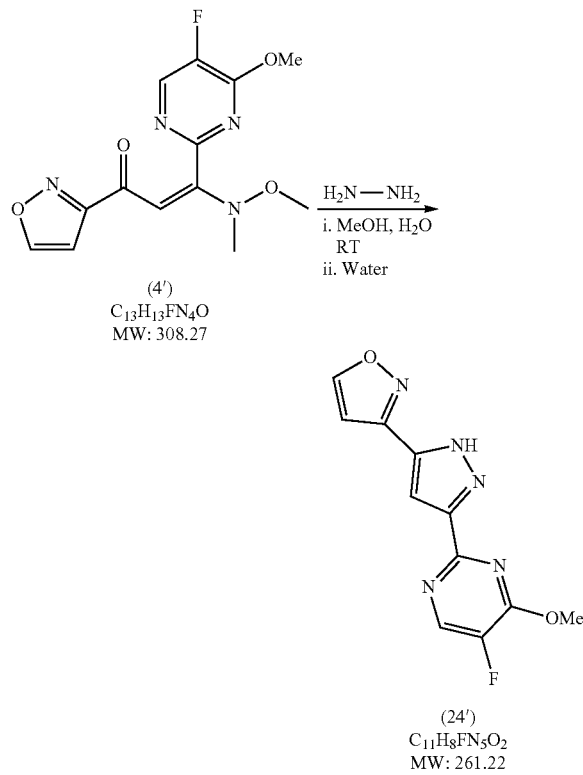

Compound (24') (3.5 g, 13.4 mmol) was dissolved in DME (130 mL) at room temperature and lithium tert-butoxide (2.14 g, 26.8 mmol) was added. After stirring for 15 minutes, benzyl bromide (4.58 g, 26.8 mmol) was added and the mixture heated at 60° C. for 16 hours and then cooled to room temperature. The mixture was diluted with ethyl acetate (45 mL) and then washed with water (3×10 mL). The organic layer was dried with magnesium sulfate and concentrated. The resulting oil was purified by silica gel chromatography to afford the desired compound (2.29 g, 46%).

Step iv): Demethylation of Formula V to Provide 5-fluoro-2-(1-(2-fluorobenzyl)-5-(isoxazol-3-yl)-1H-pyrazol-3-yl)pyrimidin-4-ol (9')

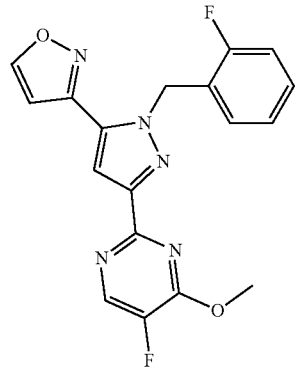

C$_{18}$H$_{13}$F$_2$N$_5$O$_2$
MW: 369.33
Formula V

HCl, MeOH →

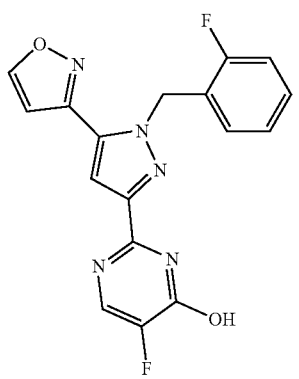

C$_{17}$H$_{11}$F$_2$N$_5$O$_2$
MW: 355.30
(9')

Formula V (5.76 kg, 15.6 mol, 1.0 equiv), methanol (46.1 L) and concentrated hydrochloric acid (3.90 L, 37 wt. %, 47.4 mol, 3.0 equiv) were charged to a 100 L jacketed reaction vessel equipped with a nitrogen inlet-outlet, thermocouple, condenser, and an overhead stirrer. The mixture was heated to 63 to 65° C. and stirred at 63 to 65° C. for a minimum of 24 hours, and a slurry was obtained. The reaction was complete by HPLC Method A (Formula V:(9') area/area %=0.8). The slurry was cooled to 20 to 25° C., over 1 hour, and held at 20 to 25° C. for 1 hour. The resulting slurry was filtered, and the filter cake was washed with methanol (17.3 L). The wet cake was dried under high vacuum at 35 to 45° C. for 16 hours until constant weight to furnish (9') as an off-white solid (5.35 kg, 97% yield, 99% pure by HPLC). $^1$H-NMR (500 MHz, DMSO-d$_6$) δ ppm 12.90-13.61 (br. s., 1H); 9.11 (d, J=1.68 Hz, 1H); 8.16 (s, 1H); 7.64 (s, 1H); 7.29-7.42 (m, 1H); 7.17-7.28 (m, 2H); 7.08-7.15 (m, 1H); 6.97 (s, 1H); 5.91 (s, 3H).

Step v): Chlorination of Compound (9') to Provide 3-(3-(4-chloro-5-fluoropyrimidin-2-yl)-1-(2-fluorobenzyl)-1H-pyrazol-5-yl)isoxazole (Formula VI)

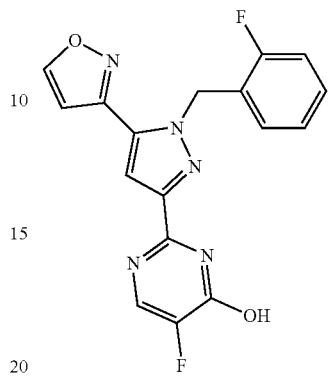

C$_{17}$H$_{11}$F$_2$N$_5$O$_2$
MW: 355.30
(9')

POCl$_3$, CH$_3$CN
———————→
N,N-dimethylaniline

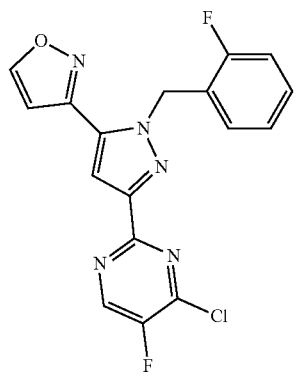

C$_{17}$H$_{10}$ClF$_2$N$_5$O
MW: 373.75
Formula VI

Intermediate (9') (3.975 kg, 11.2 mol, 1.0 equiv), acetonitrile (35.8 L) and N,N-dimethylaniline (0.28 L, 0.27 kg, 2.23 mol, 0.2 equiv) were mixed in a 100 L jacketed reaction vessel with a nitrogen inlet, thermocouple, addition funnel, condenser, and an overhead stirrer. The slurry was heated to 70 to 80° C. Phosphorous oxychloride (1.55 L, 2.55 kg, 16.6 mol, 1.5 equiv) was then charged via an addition funnel over 1 hour, while maintaining the reaction temperature at 70 to 80° C. The mixture was stirred at 75 to 80° C. for a minimum of 4 hours and a green solution was obtained. The reaction was complete by HPLC Method A ((9'):Formula VI area/area %=0.4). Then the mixture was cooled to −5 to 5° C., over 1 hour. Water (17.9 L) was charged over 40 minutes via an addition funnel, while maintaining the reaction temperature at −5 to 5° C. The resulting slurry was stirred at 0 to 5° C. for 30 minutes and filtered. The filter cake was washed with a mixture of acetonitrile (8.0 L) and water (8.0 L), and then with water (8.0 L). The filter cake was dried under high vacuum at 35 to 45° C. for 16 hours until constant weight to furnish Formula VI as an off-white solid (4.04 kg, 97% yield, 99% pure by HPLC). $^1$H NMR (500 MHz, CDCl$_3$) δ ppm 8.65 (s, 1H); 8.48 (d, J=1.68 Hz, 1H); 7.44 (s, 1H); 7.21-7.25 (m, 1H); 6.97-7.06 (m, 2H); 6.83-6.87 (m, 1H); 6.61 (d, J=1.68 Hz, 1H); 6.03 (s, 2H).

149

Example 2: Preparation of Formula IA

Step I): amination of Compound (16) to provide 2-(aminomethyl)-1,1,1,3,3,3-hexafluoropropan-2-ol (17)

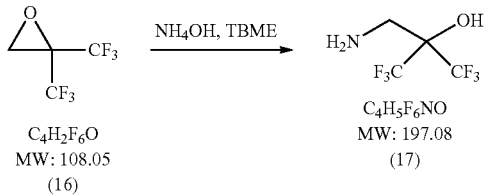 [SMILES: FC(F)(F)C1(C(F)(F)F)CO1 ; NCC(O)(C(F)(F)F)C(F)(F)F]

C$_4$H$_2$F$_6$O
MW: 108.05
(16)

C$_4$H$_5$F$_6$NO
MW: 197.08
(17)

Ammonium hydroxide (28-30% (as NH$_3$) solution in water, 1.75 L, 26.8 mol, 9.6 equiv) and methyl t-butyl ether (1.75 L) were charged to a 10 L jacketed reaction vessel equipped with a nitrogen inlet-outlet, thermocouple, condenser, and an overhead stirrer. (Note: The condenser temperature was set to be −20° C. and to minimize the evaporation loss of both ammonia gas and (16)). 2,2-Bis(trifluoromethyl)oxirane ((16), 500 g, 2.78 mol, 1.0 equiv) was charged to the vigorously stirred reaction mixture (300 RPM) over 40 minutes, while maintaining the reaction temperature at 20 to 30° C. The mixture was stirred at 20 to 30° C. for 3 hours after addition. The mixture was allowed to separate, and the bottom aqueous layer was extracted with methyl t-butyl ether 4 times (4×1.75 L). The combined organic layers were concentrated under reduced pressure (jacket temperature not more than 20° C. and the vacuum torr 100) to bring the volume to 1.5 L. n-Heptane (1.8 L) was added and the mixture was concentrated under reduced pressure (jacket temperature not more than 20° C. and the vacuum torr 100) to bring the volume to 1.5 L. The slurry was cooled to 0 to 5° C. and stirred at 0 to 5° C. for 30 minutes. The resulting slurry was filtered, and the filter cake was washed with n-heptane (500 mL). The solid was air dried in a hood at 20 to 25° C. for 10 hours until constant weight to provide intermediate (17) as a white solid (383 g, 70% yield, 99% pure by GC). $^1$H NMR (500 MHz, MeOD) δ ppm 3.09 (s, 2H).

Step vi): Coupling of Formula VI and Compound (17) to Provide 1,1,1,3,3,3-hexafluoro-2-(((5-fluoro-2-(1-(2-fluorobenzyl)-5-(isoxazol-3-yl)-1H-pyrazol-3-yl)pyrimidin-4-yl)amino)methyl)propan-2-ol (Formula IA)

C$_{17}$H$_{10}$ClF$_2$N$_5$O
MW: 373.75
Formula VI

+

C$_4$H$_5$F$_6$NO
MW: 197.08
(17)

C$_{21}$H$_{14}$F$_8$N$_6$O$_2$
MW: 534.37
Formula IA

Intermediates Formula VI (2.80 kg, 7.49 mol, 1.0 equiv) and (17) (1.76 kg, 8.93 mol, 1.2 equiv), dimethyl sulfoxide (5.6 L) and Hunig's base (1.3 L, 7.46 mol, 1.0 equiv) were charged to a 30 L jacketed reaction vessel equipped with a nitrogen inlet-outlet, thermocouple, condenser, and overhead stirrer. The reaction mixture was heated to 125 to 130° C. and held at 125 to 130° C. for a minimum of 4 hours. The reaction was complete by HPLC (Formula VI:Formula IA area/area %=1.7). The reaction mixture was cooled to 15 to 25° C.

The above reaction mixture was transferred to a 100 L jacketed reaction vessel equipped with a nitrogen inlet-outlet, thermocouple, condenser, and overhead stirrer. Toluene (11.2 L), n-heptane (22.4 L) and Hunig's base (0.64 L, 3.68 mol, 0.5 equiv) were then charged to reaction mixture. The reaction mixture was heated to 40 to 50° C. Water (4.2 L) was added to the vigorously stirred reaction mixture (300 RPM) at 40 to 50° C., over 2 hours, and the reaction mixture was stirred at 40 to 50° C. for 30 minutes to form the seed bed. More water (7.0 L) was added to the vigorously stirred slurry (300 RPM) at 40 to 50° C., over 2 hours. The slurry was cooled to 20 to 25° C., over 1 hour and stirred at 20 to 25° C. for 20 minutes. The resulting slurry was filtered, and the filter cake was washed with a pre-mixed solution of n-heptane and toluene (5.6 L/2.8 L), then with a pre-mixed solution of water and methanol (5.6 L/2.8 L). The filter cake was then dried under vacuum at 35 to 45° C. for 16 hours until constant weight to furnish Formula IA as an off-white solid (4.05 kg, contaminated with 7 wt % DMSO by HNMR, assay adjusted 94% yield, 98% pure by HPLC). $^1$H NMR (500 MHz, DMSO-d6) δ ppm 9.11 (d, J=1.96 Hz, 1H); 8.66 (s, 1H); 8.37 (d, J=3.13 Hz, 1H); 8.11 (t, J=5.87 Hz, 1H); 7.48 (s, 1H); 7.30-7.37 (m, 1H); 7.17-7.24 (m, 1H); 7.21 (d, J=1.7 Hz, 1H); 7.06-7.13 (m, 1H); 7.00-7.06 (m, 1H); 5.87 (s, 2H); 4.11 (d, J=5.87 Hz, 2H).

Step II): Recrystallization of the Compound of Formula IA to Provide Purer Compound of Formula IA (Corresponds to Steps A'), B'), C'), D') and E') in the Process of Preparing Compound of Formula IA or in the 13$^{th}$ Specific Embodiment Described Above)

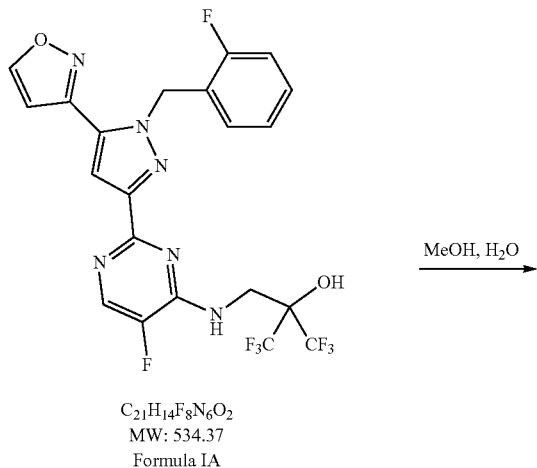

$C_{21}H_{14}F_8N_6O_2$
MW: 534.37
Formula IA

MeOH, H$_2$O

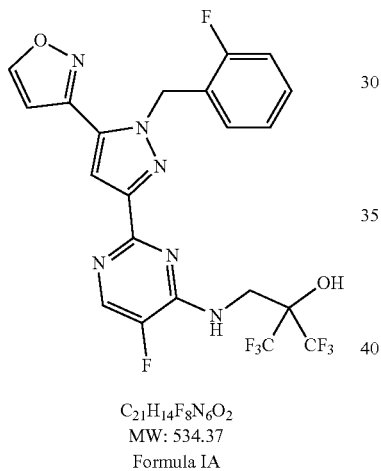

$C_{21}H_{14}F_8N_6O_2$
MW: 534.37
Formula IA

Compound of Formula IA, obtained above (1$^{st}$ Portion, 4.76 kg, 8.91 mol) and methanol (19.0 L) were charged to a 30 L jacketed reaction vessel. The reaction mixture was stirred at low speed and heated to 40 to 50° C. until most solids dissolved. The solution in the 30 L jacketed reaction vessel was in-line filtered via gas dispersion tube (coarse frit) into a 100 L jacketed reaction vessel. Methanol (4.8 L) was used to rinse the 30 L jacketed reaction vessel and the rinse was transferred to the 100 L jacketed reaction vessel.

Compound of Formula IA, obtained above (2$^{nd}$ portion, 4.96 kg, 9.28 mol) and methanol (19.9 L) were charged to a 30 L jacketed reaction vessel. The reaction mixture was stirred at low speed and heated to 40 to 50° C. until most solids dissolved. The solution in the 30 L jacketed reaction vessel was in-line filtered via gas dispersion tube (coarse frit) into the 100 L jacketed reaction vessel. Methanol (5.0 L) was used to rinse the 30 L jacketed reaction vessel and the rinse was transferred to the 100 L jacketed reaction vessel.

Methanol (12.0 L) was added to the 100 L jacketed reaction vessel to bring the volume to 68.0 L. The reaction mixture was then heated to 55 to 65° C., and water (29.2 L) was charged over 1 hour 30 minutes, while maintaining the batch temperature at 50 to 60° C. The resulting slurry was cooled to 20 to 25° C., over 2 hours and held at 20 to 25° C. for 1 hour. The slurry was filtered, and the filter cake was washed with a pre-mixed solution of methanol and water (19.5 L/19.5 L). The filter cake was then dried under vacuum at 40 to 50° C. for 24 hours to furnish the compound of Formula IA as a white solid (8.93 kg, 92% yield, 99% pure by HPLC). $^1$H NMR (500 MHz, DMSO-d$_6$) δ ppm 9.11 (d, J=1.96 Hz, 1H); 8.66 (s, 1H); 8.37 (d, J=3.13 Hz, 1H); 8.11 (t, J=5.87 Hz, 1H); 7.48 (s, 1H); 7.30-7.37 (m, 1H); 7.17-7.24 (m, 1H); 7.21 (d, J=1.7 Hz, 1H); 7.06-7.13 (m, 1H); 7.00-7.06 (m, 1H); 5.87 (s, 2H); 4.11 (d, J=5.87 Hz, 2H).

Characterization of Crystalline Form a of the Compound of Formula IA

Crystallinity of the compound of Formula IA prepared according to procedure described above was determined by XRPD. The XPRD pattern is provided in FIG. 1.

Figure 2:
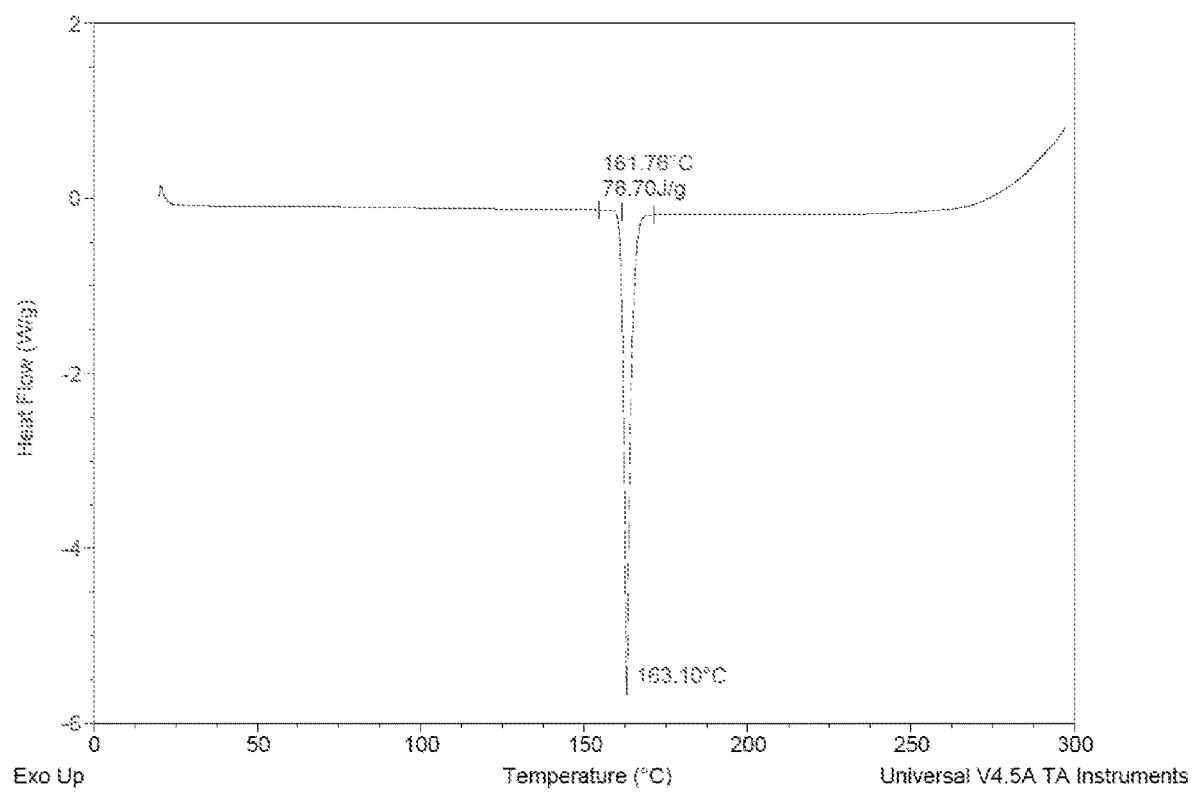
FIG. 2 shows a DSC profile of crystalline Form A of the compound of Formula IA.

The melting range by differential scanning calorimetry (DSC) was also determined. DSC analysis was performed in a sealed pan with the temperature increased at a rate of 10° C./min up to 300° C. The DSC profile is shown in FIG. 2 and indicates a melting point of 163.1° C.

Example 3: Preparation of the Compound of Formula ID

Step A): cyanation of Compound (10) to provide racemic mixture 2-(bromomethyl)-3,3,3-trifluoro-2-((trimethylsilyl)oxy)propanenitrile (11)

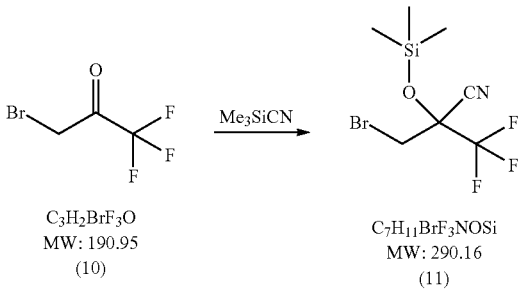

$C_3H_2BrF_3O$
MW: 190.95
(10)

Me$_3$SiCN $C_7H_{11}BrF_3NOSi$
MW: 290.16
(11)

Trimethylsilanecarbonitrile (3.41 kg, 34.4 mmol, 0.97 equiv) and triethylamine (0.100 L, 0.073 kg, 0.72 mol, 0.02 equiv) were mixed in a 30 L jacketed reactor. The mixture was cooled to 10-15° C. 3-Bromo-1,1,1-trifluoropropan-2-one ((10), 6.74 kg, 35.3 mol, 1.0 equiv) was charged via an addition funnel over 1 hour 40 minutes, while maintaining the reaction temperature between 0 to 20° C. The reaction mixture was stirred at 20 to 25° C. for 1 hour. $^1$H-NMR of the reaction sample indicated the reaction was complete ((10):(11) area:area %=<1) to furnish intermediate (11) as dense oil. This intermediate (11) (racemic mixture) was used directly in next step. $^1$H-NMR (500 MHz, CDCl$_3$) δ ppm 3.68 (d, J=11.14 Hz, 1H); 3.57 (d, J=11.14 Hz, 1H), 0.34-0.37 (m, 9H).

Step B): Conversion of Nitrile Racemic Mixture (11) to Amide to Provide Racemic Mixture 2-(bromomethyl)-3,3,3-trifluoro-2-hydroxypropanamide (12)

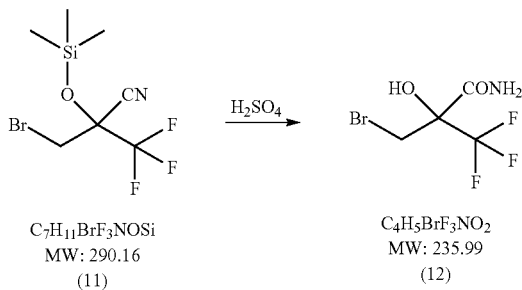

Concentrated sulfuric acid (8.6 L, 158 mol, 4.5 equiv) was stirred in a 100 L jacketed reactor. The sulfuric acid was heated to 40 to 45° C., then the above intermediate (11) (racemic) was added via an addition funnel over 1 hour while keeping the temperature below 75° C. The reaction mixture was stirred at 65 to 75° C. for 2 hours and then allowed to cool to 20 to 25° C. The reaction mixture was further cooled to −15 to −5° C. and diluted with ethyl acetate (40.4 L) via an addition funnel over 2 hours (very exothermic) while keeping the temperature between −15 to −5° C. Water (33.7 L) was added via an addition funnel for 1 hour 30 minutes (very exothermic) while keeping the temperature between −15 to −5° C. The reaction mixture was warmed to and held at 0 to 5° C. The layers were separated and 15% aqueous sodium chloride (20 L) was added to the organic layer, followed with 20% aqueous sodium bicarbonate (20 L) while maintaining the temperature between 5 to 20° C., over 5 minutes. The mixture was stirred for 10 minutes and the layers were separated. The organic layer was washed with 15% aqueous sodium chloride (20 L). The organic layer was transferred via in-line filter via gas dispersion tube (coarse frit) to a 20 L rotavapor and concentrated under reduced pressure until no more distillate was observed, to obtain 10.0 kg of crude intermediate (12) (racemic) as a light yellow oil, which has 77 wt % of intermediate (12) (racemic) based on $^1$H-NMR assay. This oil was dissolved in methanol (6.7 L) and concentrated to furnish 9.13 kg of intermediate (12) (racemic). (7.73 kg adjusted weight). This oil was used directly in the next step. $^1$H-NMR (500 MHz, CDCl$_3$) δ 6.61-6.94 (m, 1H); 5.92-6.26 (m, 1H); 3.93-4.00 (m, 1H); 3.68 (d, J=11.14 Hz, 1H).

Step C): Amination of Racemic Mixture (12) to Provide Racemic Mixture 2-(aminomethyl)-3,3,3-trifluoro-2-hydroxypropanamide (13)

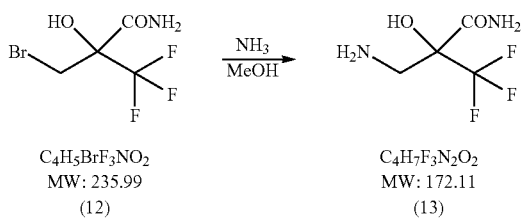

7 N ammonia in methanol (57.5 L, 403 mol, 12.3 equiv) was stirred in a 100 L reactor. The solution was cooled to −10 to 10° C. Then the above obtained intermediate (12) (racemic, 7.73 kg, 32.8 mol, 1.0 equiv) was added via an addition funnel over 3 minutes. The reaction mixture was warmed to 20 to 30° C., over 1 hour and held at this temperature for 16 hours. The reaction mixture was cooled to 0 to 10° C. and sodium methoxide (5.8 L, 5.4 M, 31.3 mol, 0.95 equiv) was added over 2 minutes. The reaction mixture was then split into 4 equal portions and processed. Each portion was concentrated under reduced pressure to a volume of 7.7 L and ethyl acetate (11.6 L) was continuously charged while distilling to azeotropically remove methanol to a volume of 7.7 L as a slurry. This process was repeated for the rest of the three portions. All the ethyl acetate slurries from 4 the portions were transferred to a 100 L jacketed reactor and more ethyl acetate was added to make up the volume to 74 L. Water (7.7 L) was added and the reaction mixture was stirred vigorously for 20 to 30 minutes and then allowed to separate for minimum of 12 hours.

The ethyl acetate layer was then split into 4 equal portions and processed. Each portion was concentrated under reduced pressure to a volume of 7.7 L. This process was repeated for the rest of the three portions. All 4 portions were transferred to the 100 L jacketed reactor and ethyl acetate was added to make up the volume to 46.4 L. The reaction mixture was heated to 55 to 60° C. and heptane (38.7 L) was added over 50 minutes, while maintaining the temperature above 50° C. The resulting slurry was cooled to 20 to 25° C., over 2 hours, then held at 20 to 25° C. for 1 hour 30 minutes, and filtered onto an 18 inches Buchner funnel. Ethyl acetate (3.9 L) and heptane (7.7 L) were charged to the reactor, the mixture stirred for 2 minutes, and transferred to the filter to wash the cake. The wet cake was dried on the filter for 2 hours and then dried under vacuum at 25 to 30° C., for 36 hours until constant weight to furnish the intermediate (13) (racemic) as an off-white solid (3.21 kg, 53% yield). $^1$H-NMR (500 MHz, MeOH-d$_4$) δ ppm 2.94 (d, J=13.73 Hz, 1H); 3.24 (d, J=13.58 Hz, 1H).

Step D): Chiral Resolution of Racemic Mixture (13) as the D-Malic Acid Salt (14) of (R)-2,2-dimethyl-5-(trifluoromethyl)oxazolidine-5-carboxamide (20)

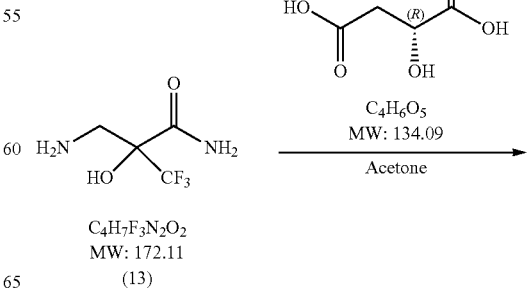

-continued

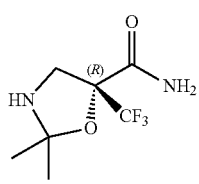

(20)

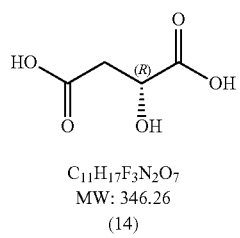

C₁₁H₁₇F₃N₂O₇
MW: 346.26
(14)

Intermediate (13) (racemic) (2.0 kg, 11.6 mol, 1.0 equiv) and acetone (10.0 L) were mixed in a 22 L round bottom flask equipped with a mechanical stirrer, an addition funnel and a digital thermometer. The reaction mixture was stirred at low speed at 20 to 25° C. to obtain a solution.

Separately, (D)-(+)-malic acid (1.56 kg, 11.6 mol, 1.0 equiv) and acetone (30 L) were stirred in a 100 L jacketed reactor. The reaction solution was heated to 33 to 38° C. Then 20% of above intermediate (13) solution in acetone was charged to the 100 L jacketed reactor in one portion followed by a slurry of intermediate (14) (0.52 g) in acetone (20 mL) as seeds. The remaining 80% of (13) solution in acetone was then charged to the 100 L jacketed reactor over a minimum of 1 hour, while maintaining the reaction temperature between 33 to 38° C. The reaction mixture was cooled to 28 to 32° C. evenly over a minimum of 2 hour and stirred at 28 to 32° C. for a minimum of 12 hours. The resulting slurry was filtered at 28 to 32° C., and the filter cake was washed with acetone (16.0 L) (Note: Care was taken to ensure that the filter cake did not dry at the beginning of filtration). The filter cake was then dried under vacuum at 30° C. for 8 hours until constant weight to furnish salt (14) as an off-white solid (1.53 kg, 38% yield, RR:SR=97:3 by chiral GC). ¹H-NMR (500 MHz, D₂O) δ ppm 4.33 (br, s, 1H); 3.61 (br, d, J=13.58 Hz, 1H); 3.40-3.47 (m, 1H); 2.76 (br, d, J=15.87 Hz, 1H); 2.53-2.63 (m, 1H); 2.16 (br, s, 4H).

Step E): Coupling of Formula VI and Malic Acid Salt (14) to Provide (R)-3,3,3-trifluoro-2-(((5-fluoro-2-(1-(2-fluorobenzyl)-5-(isoxazol-3-yl)-1H-pyrazol-3-yl)pyrimidin-4-yl)amino)methyl)-2-hydroxypropanamide (Formula ID)

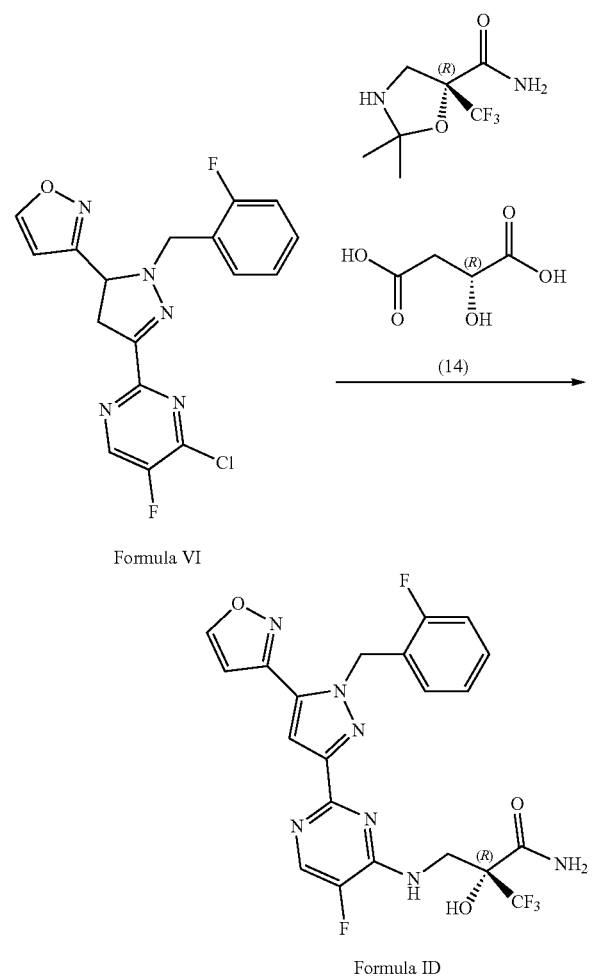

Formula VI

Formula ID

The (D)-malic acid salt (14) (0.81 kg, 2.34 moles, 1.25 equiv) and water (0.98 L) were charged to a 30 L jacketed reaction vessel. The reaction mixture was stirred at low speed and the jacket was heated to 65 to 70° C. and held at this temperature for 30 min. Acetone generated during the reaction was removed by applying a gentle vacuum. The reaction mixture was cooled to 20 to 40° C. and Formula VI (0.70 kg, 1.87 moles, 1.0 equiv), DMSO (9.8 L) and Hunig's base (0.82 L, 4.71 moles, 2.5 equiv) were charged. The reaction mixture was heated to 88 to 93° C., over 2 h and held at 88 to 93° C. for 20 h. The reaction was completed by HPLC (Formula VI:Formula ID area/area %=0.5). Then the mixture was cooled to 50 to 60° C. Another portion of Hunig's base (1.96 L, 11.3 moles, 6.0 equiv) was charged followed by water (4.9 L) over 15 min at 50 to 60° C. The reaction mixture was stirred for 15 min at 50 to 60° C. to form the seed bed. Water (7.0 L) was added via addition funnel at 50 to 60° C., over 30 min, and the mixture was held at 50 to 60° C. for 30 min. The resulting slurry was filtered at 50 to 60° C., and the filter cake was washed with a pre-mixed solution of methanol and water (3.5 L/3.5 L). The filter cake was then dried under vacuum at 50° C. for 16 h until constant weight to furnish Formula ID as an off-white solid (0.83 kg, 87% yield). ¹H-NMR (500 MHz, DMSO-d₆) δ ppm 9.10 (s, 1H); 8.33 (d, J=2.90 Hz, 1H); 7.93 (s, br, 1H); 7.90 (s, 1H); 7.78 (s, br, 1H); 7.69 (s, br, 1H); 7.52 (s, 1H); 7.33 (q, J=7.02 Hz, 1H); 7.17-7.25 (m, 1H); 7.17-7.25 (m, 1H); 7.10 (t, J=7.48 Hz, 1H); 6.98 (t, J=7.55 Hz, 1H); 5.90 (s, 2H); 3.92-4.05 (m, 2H).

Step F): Hydrolysis of Oxazolidine Salt Malic Acid Salt (14) to Provide the HCl Salt (15) of (R)-2-(aminomethyl)-3,3,3-trifluoro-2-hydroxypropanamide (15A)

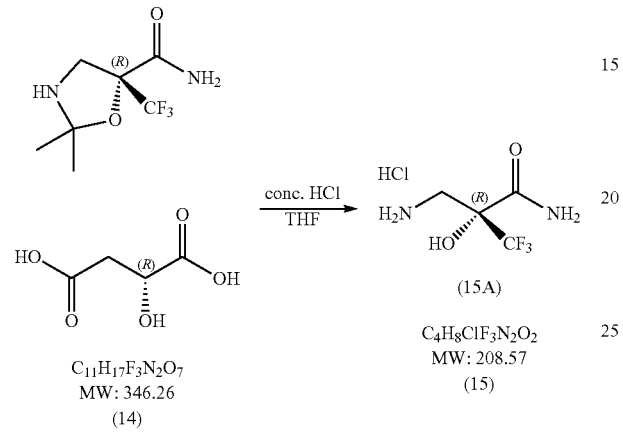

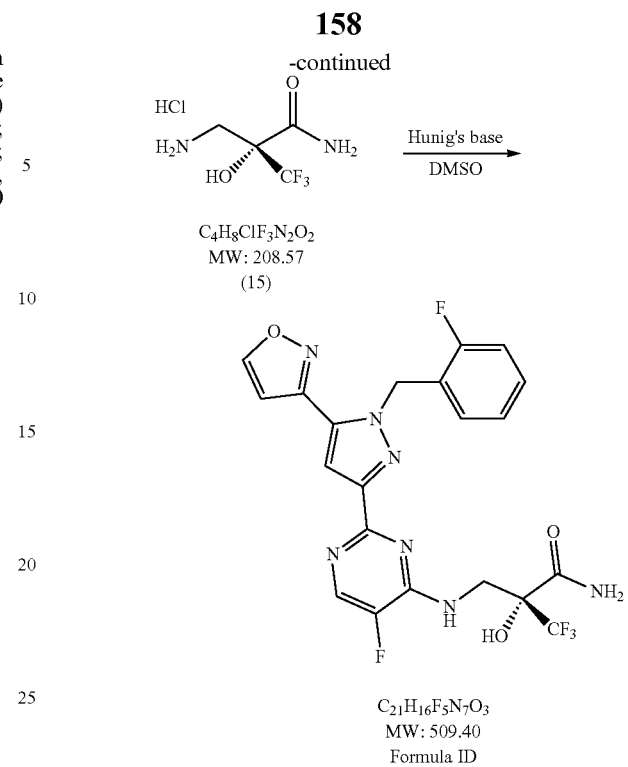

Malic acid salt (14) (1.53 kg, 4.42 mol, 1.0 equiv) and THF (12.3 L) were stirred in a 100 L jacketed reactor. The slurry was stirred at 20 to 25° C. for 5 minutes. Conc. HCl (37 wt %, 0.41 L, 4.92 mol, 1.1 equiv) was charged to the 100 L jacketed reactor in one portion. The reaction mixture was stirred at 20 to 30° C. for a minimum of 1 hour. The slurry was cooled to 0 to 5° C., over 1 hour and held at 0 to 5° C. for 1 hour. The resulting slurry was filtered, and the filter cake was washed with THF (3.1 L). The wet cake was dried under high vacuum at 45 to 55° C. for 16 hours until constant weight to furnish HCl salt (15) as an off-white solid (0.83 kg, 90% yield, R:S=97.7:2.3 by chiral GC). ¹H-NMR (500 MHz, D₂O) δ ppm 3.50 (d, J=13.73 Hz, 1H); 3.67 (d, J=13.73 Hz, 1H).

Large Scale Step vi): Coupling of Formula VI and HCl Salt (15) to Provide (R)-3,3,3-trifluoro-2-(((5-fluoro-2-(1-(2-fluorobenzyl)-5-(isoxazol-3-yl)-1H-pyrazol-3-yl)pyrimidin-4-yl)amino)methyl)-2-hydroxypropanamide (Formula ID)

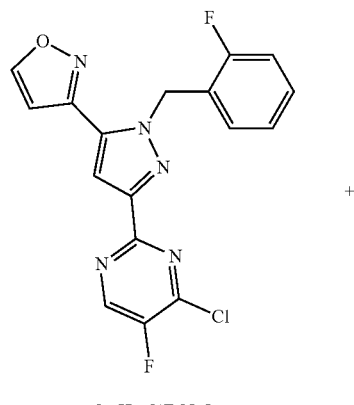

Formula VI (1.02 kg, 2.73 mol, 1.0 equiv), salt (15) (0.685 kg, 3.28 mol, 1.2 equiv), dimethyl sulfoxide (4.1 L) and Hunig's base (1.29 L, 7.41 mol, 2.7 equiv) were charged to a 30 L jacketed reaction vessel equipped with a nitrogen inlet-outlet, thermocouple, condenser, and an overhead stirrer. The reaction mixture was heated to 99 to 103° C. and held at 99 to 103° C. for a minimum of 4 hours. The reaction was complete by HPLC method A (Formula VI:Formula ID area:area %=0.6). The reaction mixture was cooled to 50 to 55° C. and methanol (4.1 L) was then charged in one portion. Water (2.7 L) was added to the reaction mixture at 50 to 55° C., over 30 minutes and the reaction mixture was stirred at 50 to 55° C. for 15 minutes to form the seed bed. More water (5.5 L) was added at 50 to 55° C., over 30 minutes, and the slurry was held at 50 to 55° C. for 30 minutes. The slurry was then cooled to 20 to 25° C., over 1 hour and stirred at 20 to 25° C. for 1 hour. The slurry was filtered, and the filter cake was washed with a pre-mixed solution of methanol and water (10.2 L/10.2 L). The filter cake was then dried under vacuum at 45 to 55° C. for 16 hours until constant weight to furnish compound of Formula ID as an off-white solid (1.29 kg, 93% yield, 100% pure by HPLC, R:S=99.2:0.8 by chiral HPLC). ¹H-NMR (500 MHz, DMSO-d₆) δ ppm 9.10 (s, 1H); 8.33 (d, J=2.90 Hz, 1H); 7.93 (s, br, 1H); 7.90 (s, 1H); 7.78 (s, br, 1H); 7.69 (s, br, 1H); 7.52 (s, 1H); 7.33 (q, J=7.02 Hz, 1H); 7.17-7.25 (m, 1H); 7.17-7.25 (m, 1H); 7.10 (t, J=7.48 Hz, 1H); 6.98 (t, J=7.55 Hz, 1H); 5.90 (s, 2H); 3.92-4.05 (m, 2H).

Kg Scale STEP vi): Coupling of Formula VI and HCl Salt (15) to Provide (R)-3,3,3-trifluoro-2-(((5-fluoro-2-(1-(2-fluorobenzyl)-5-(isoxazol-3-yl)-1H-pyrazol-3-yl)pyrimidin-4-yl)amino)methyl)-2-hydroxypropanamide (Formula ID)

Formula VI (53.5 mmol, 1.0 equiv), (15) (12.3 g, 59.0 mmol, 1.1 equiv), dimethyl sulfoxide (40.0 mL) and Hunig's base (21.4 g, 166 mmol, 3.1 equiv) were charged to a 500 mL jacketed reaction vessel equipped with a nitrogen inlet-outlet, thermocouple, condenser, and an overhead stirrer. The reaction mixture was heated to 100 to 105° C. and held at 100 to 105° C. for a minimum of 4 hours. The reaction was complete by HPLC method A (Formula VI:Formula ID area:area %=1.0). The reaction mixture was cooled to 58 to 63° C. and methanol (160 mL) was then charged to the reaction mixture in one portion. Water (60 mL) was added to the reaction mixture at 58 to 63° C., over 30 minutes, and the reaction mixture was stirred at 58 to 63° C. for 15 minutes to form the seed bed. More water (140 mL) was added at 58 to 63° C., over 30 minutes, and the slurry was held at 58 to 63° C. for 30 minutes. The slurry was then cooled to 30 to 35° C., over 2 hours and stirred at 30 to 35° C. for 1 hour. The slurry was filtered, and the filter cake was washed with a pre-mixed solution of methanol and water (100 mL/100 mL). The filter cake was then dried under vacuum at 70 to 80° C. for 16 hours until constant weight to furnish Formula ID as an off-white solid (26.3 g, 96% yield, 99.3% pure by HPLC). $^1$H-NMR (500 MHz, DMSO-$d_6$) δ ppm 9.10 (s, 1H); 8.33 (d, J=2.90 Hz, 1H); 7.93 (s, br, 1H); 7.90 (s, 1H); 7.78 (s, br, 1H); 7.69 (s, br, 1H); 7.52 (s, 1H); 7.33 (q, J=7.02 Hz, 1H); 7.17-7.25 (m, 1H); 7.17-7.25 (m, 1H); 7.10 (t, J=7.48 Hz, 1H); 6.98 (t, J=7.55 Hz, 1H); 5.90 (s, 2H); 3.92-4.05 (m, 2H).

Step G): Recrystallization of the Compound of Formula ID to Provide Polymorph Form B of the Compound of Formula ID (Corresponds to Steps A"), B"), C"), D") and E") in the Process of Preparing the Compound of Formula ID or in the 18$^{th}$ Specific Embodiment)

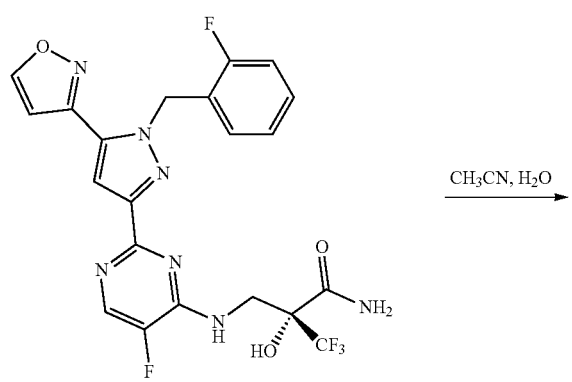

$C_{21}H_{16}F_5N_7O_3$
MW: 509.40
Formula ID

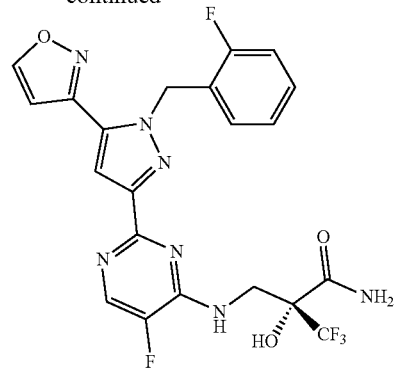

$C_{21}H_{16}F_5N_7O_3$
MW: 509.40
Formula ID Form B

Formula ID (25.7 g, 50.5 mmol), obtained above, acetonitrile (386 mL) and water (68 mL) were charged to a 1 L jacketed reaction vessel. The reaction mixture was stirred at low speed and heated to 70 to 75° C. until most solids dissolved. The solution in the 1 L jacketed reaction vessel was in-line filtered via gas dispersion tube (coarse frit) into another 1 L jacketed reaction vessel. The reaction mixture was then heated to 70 to 75° C. to obtain a solution, and water (318 mL) was charged while maintaining the batch temperature above 65° C., over 30 minutes. The resulting slurry was stirred at 65 to 72° C., over 1 hour and cooled to 0 to 5° C., over a minimum of 2 hours and held at 0 to 5° C. for a minimum of 1 hour. The slurry was filtered, and the filter cake was washed with a pre-mixed solution of acetonitrile and water (125 mL/125 mL). The filter cake was then dried under vacuum at 80 to 95° C. for a minimum of 20 hours to furnish Formula ID, Form B as a white solid (22.7 g, 88% yield). $^1$H-NMR (500 MHz, DMSO-$d_6$) δ ppm 9.10 (s, 1H); 8.33 (d, J=2.90 Hz, 1H); 7.93 (s, br, 1H); 7.90 (s, 1H); 7.78 (s, br, 1H); 7.69 (s, br, 1H); 7.52 (s, 1H); 7.33 (q, J=7.02 Hz, 1H); 7.17-7.25 (m, 1H); 7.17-7.25 (m, 1H); 7.10 (t, J=7.48 Hz, 1H); 6.98 (t, J=7.55 Hz, 1H); 5.90 (s, 2H); 3.92-4.05 (m, 2H).

Characterization of Crystalline Form B of the Compound of Formula ID

Figure 3A:
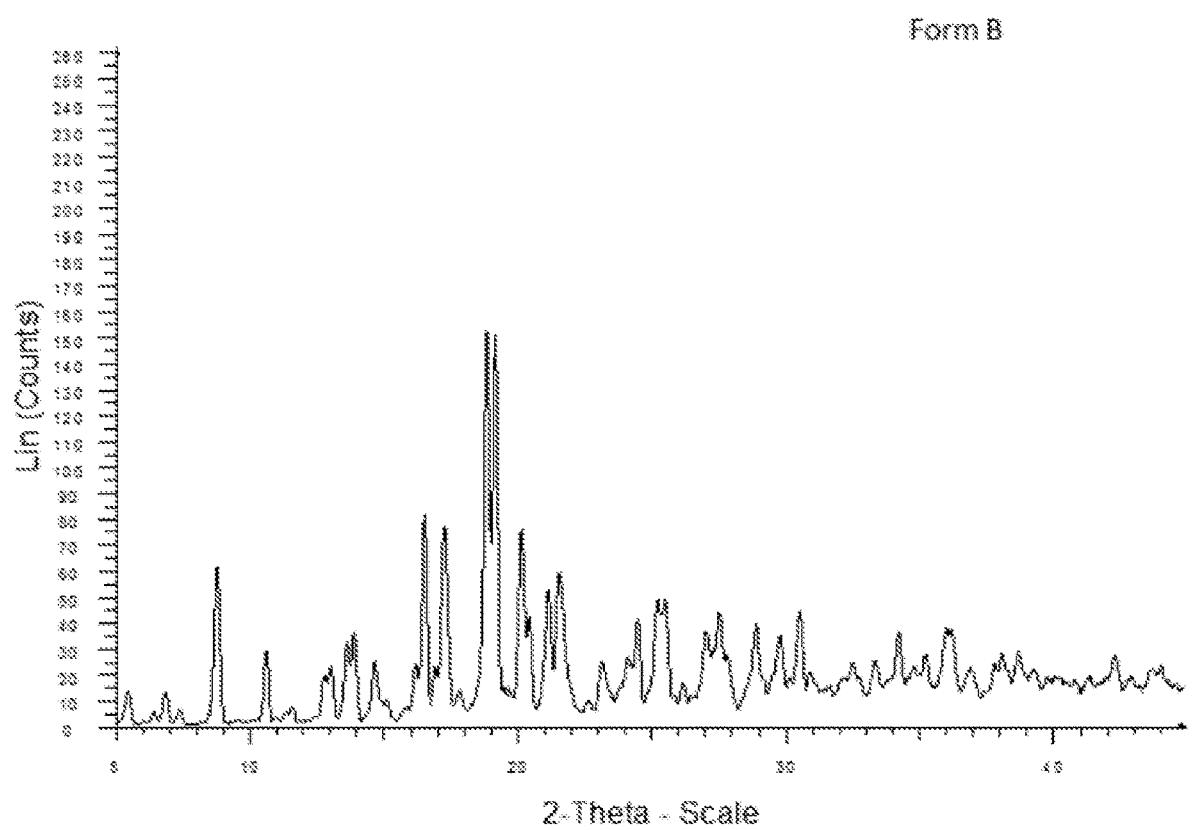
FIG. 3A shows an XRPD pattern of crystalline Form B of the compound of Formula ID in the 2θ angle range of 5 to 45 degrees.
Figure 3B:
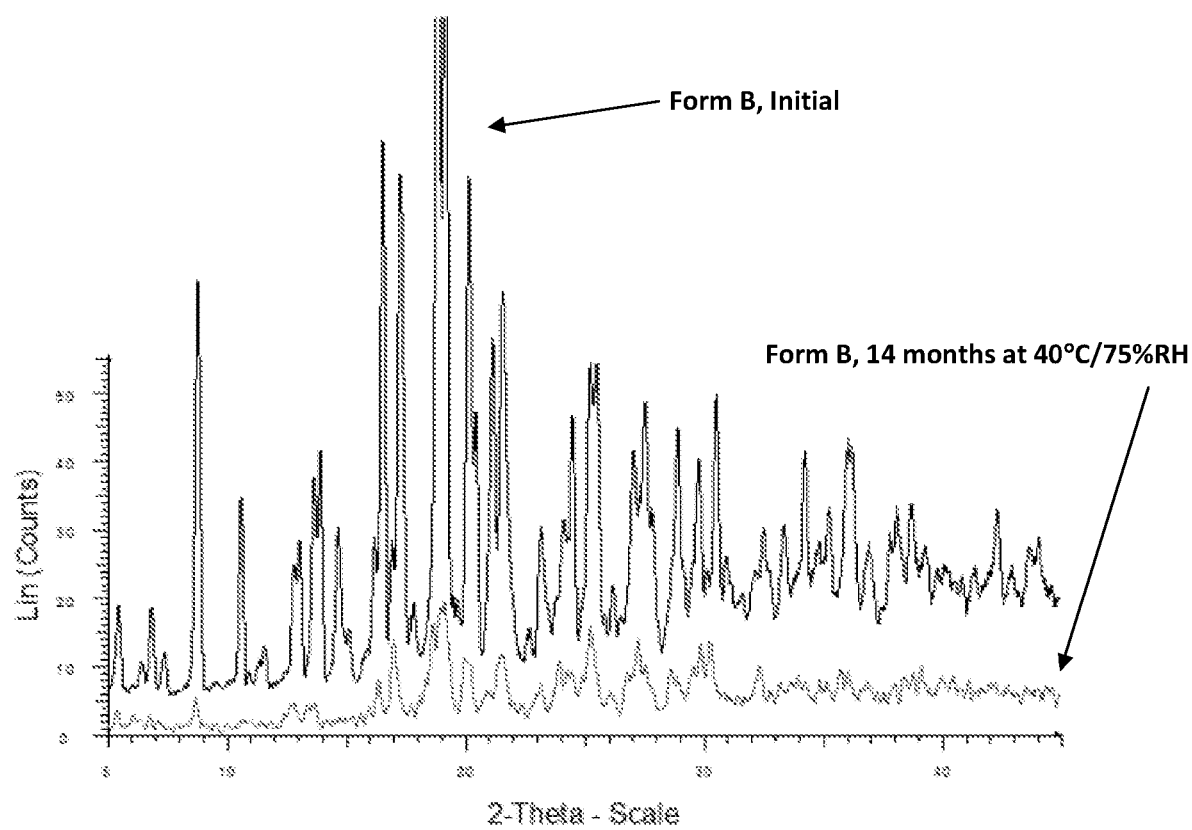
FIG. 3B shows an XRPD pattern of crystalline Form B of the compound of Formula ID before and after storage for 14 months.
Figure 3C:
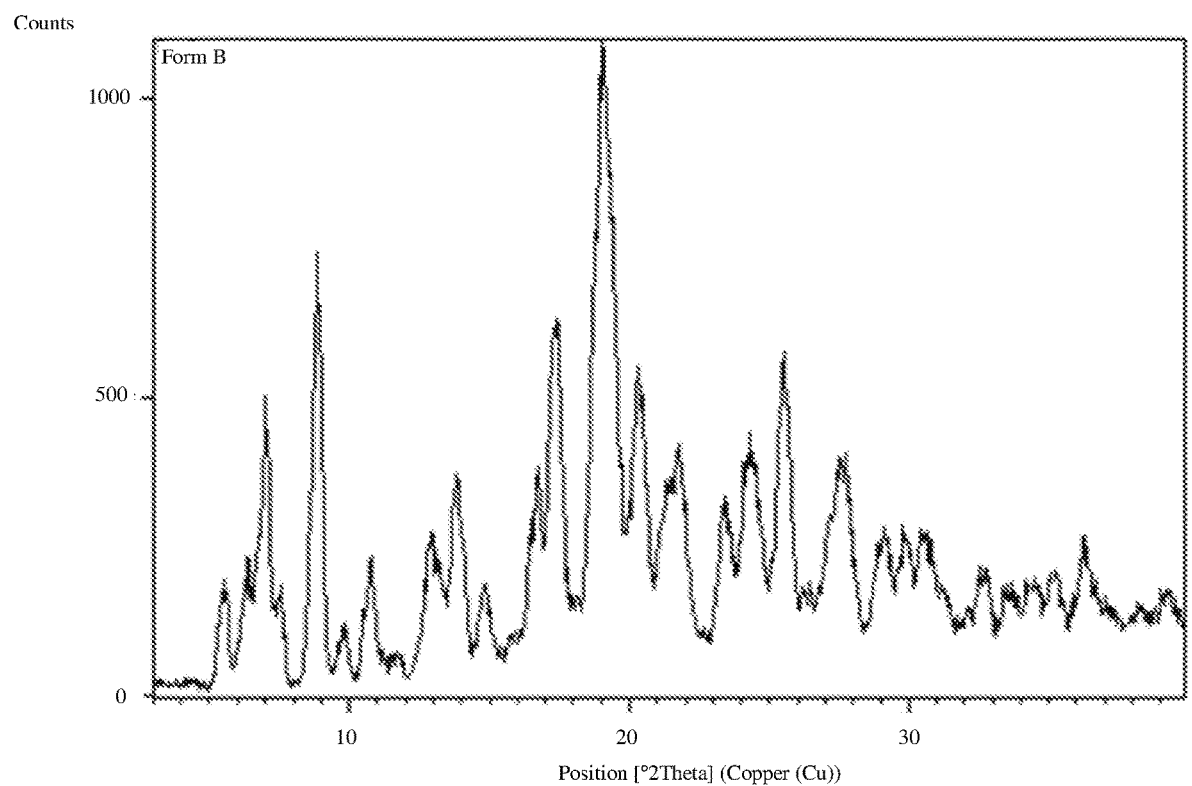
FIG. 3C shows an XRPD pattern of crystalline Form B of the Compound of Formula ID in the 2θ angle range of 3 to 40 degrees.

Crystallinity of Form B of Formula ID was analyzed by XRPD. Form B is characterized by an XRPD pattern as shown in FIGS. 3A, 3B and 3C.

In one embodiment, Form B is characterized by one or more peaks in the XRPD spectrum at 18.8 to 19.1 °2θ.

In another embodiment, Form B is characterized by one or more peaks in the XRPD spectrum selected from: 8.8, 16.4, 17.2, 18.8-19.1, 20.1, and 21.1-21.6 °2θ.

In another embodiment, Form B is characterized by one or more peaks in the XRPD spectrum selected from: 8.8, 10.6, 12.6-13.0, 14.6, 16.4, 17.2, 18.8-19.1, 20.1, 21.1-21.6, 24.5, 25.3, 27.0-27.5, 28.9, 29.8 and 30.5 °2θ.

In some embodiments, Form B is characterized by an XRPD spectrum substantially similar to that shown in FIG. 3C.

In other embodiments, Form B is characterized by one or more peaks in the XRPD spectrum selected from: 8.9 (76.55% rel int), 17.4 (57.67%), 19.1 (100.00%), and 25.5 (52.26) °2θ.

In other embodiments, Form B is characterized by one or more peaks in the XRPD spectrum selected from: 7.0

(44.44% rel int), 8.9 (76.55%), 17.4 (57.67%), 19.1 (100.00%), 20.3 (49.78%), 21.8 (36.16%), and 25.5 (52.26) °2θ.

In other embodiments, Form B is characterized by displaying an essentially unchanged XRPD trace when stored for 14 months under the stability conditions of 40° C. and 75% relative humidity. XRPD traces for Form B before and after storage under those conditions are shown in FIG. 3B.

Example 4. Large Scale Synthesis of Compound (4')

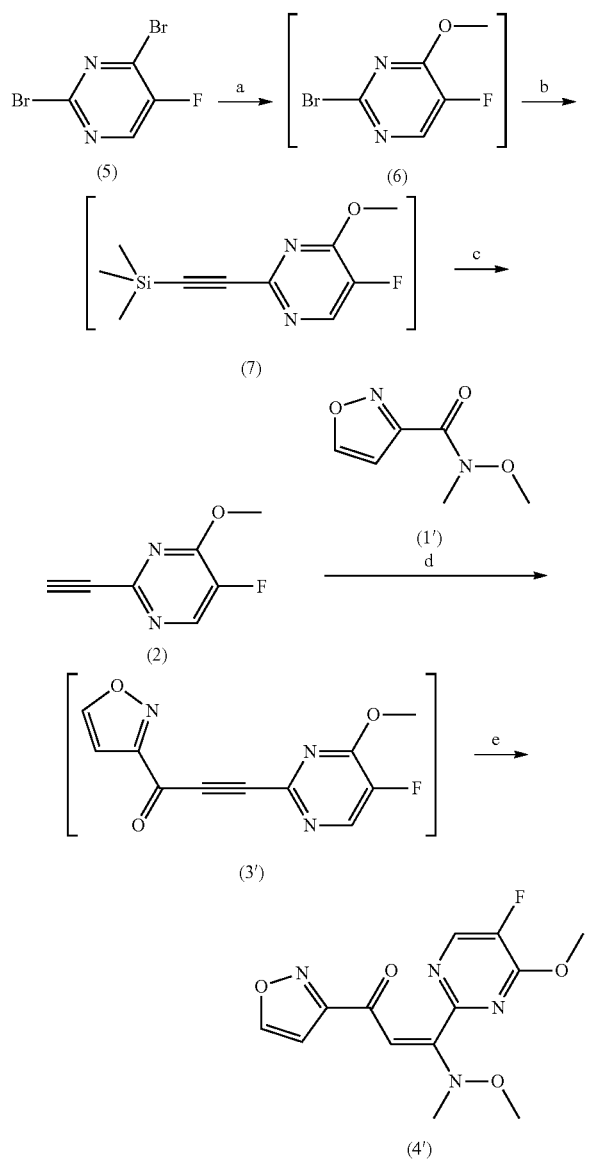

Reagents and conditions: (a) NaOMe, MeOH, -15~-5° C., 1-2 h; (b) CuI, PdCl₂(PPh₃)₂, TMS-Acetylene, Et₃N, 20-30° C., 15-20 h; (c) KF, MeOH, 20-30° C., 1-2 h, 75~84% yield (over three steps); (d) n-BuLi, THF, (1'), -78° C., 1-3 h; (e) NH(MeO)Me·HCl, 20-30° C., 0.5-1 h, EA, CH₃COOH, 75~84% yield (over two steps);

2-bromo-5-fluoro-4-methoxypyrimidine (6)

2,4-Dibromo-5-fluoropyrimidine (5) (44.9 kg, 175.4 mol, 1.0 equiv) and methanol (199 kg) were added into the reactor at 20~30° C. under N2. The mixture was stirred at 20~30° C. for 0.5-1 h until compound (5) was completely dissolved, then cooled down to -15~-5° C. (Note: compound (5) may be precipitated out below 5° C.). Sodium methoxide solution (35.0 kg, 192.9 mol, 1.1 equiv) was dropwise added to the reaction mixture over 7 h while maintaining the inner temperature between -15 to -10° C. (Note: The reaction was exothermic. The temperature should be kept below -10° C. to minimize bismethoxy byproduct.) After addition, a chase wash of methanol (22.6 kg) followed. Then the mixture was then stirred at -15~-5° C. for 1~2 h until the reaction was completed (Note: The temperature should be kept below -10° C. during IPC operation). The reaction mixture was quenched by the addition of 2M HCl solution (10 kg) over 10 minutes at -15~-5° C. (Note: The pH should be adjusted to be 3~4). Water (130 kg) was added to the reaction mixture (pH=~6), and then the solution was stirred for 10~30 min at -15~-5° C. and then warm to 20~30° C. The reaction solution was concentrated under vacuum until most methanol was distilled out (Note: the jacket temperature was kept below 30° C.). The resulting residue was extracted with Methyl t-butyl ether (MTBE) (350 kg), settled, separated and the aqueous layer was removed. The organic layer was then washed twice with water (2×200 kg) until the pH of aqueous layer to be ~7. The remaining organic layer (MTBE) was concentrated under vacuum to 5~6 volume below 30° C. An additional MTBE (150 kg) was added and then distilled to 5~6 volume to control the water content (by KF analysis) of compound (6)/MTBE solution below 0.5%. (Note: the jacket temperature was kept below 30° C.). The resulting solution was directly telescoped to the next step without further purification.

5-fluoro-4-methoxy-2-((trimethylsilyl)ethynyl)pyrimidine (7)

Triethylamine (35.2 kg, 347.8 mol, 1.98 equiv) was added into compound (6)/MTBE solution, and then the mixed solution was degassed via bubbling nitrogen for 0.5~1 h at 20~30° C. Pd(PPh₃)₂Cl₂ (0.32 kg, 0.455 mol, 0.0025 equiv) and Copper (I) iodide (CuI) (0.17 kg, 0.892 mol, 0.005 equiv) was added to the mixture under N2, and then stirred for 30 min. The ethynyltrimethylsilane (21.0 kg, 213.8 mol, 1.2 eq) was slowly added into the reaction mixture over 3~4 h, while maintaining the inner temperature at 20-30° C. (Note: the reaction was slightly exothermic.) The mixture was stirred at 20~30° C. for 15~20 h until the reaction was completed (Note: IPC control: less than 0.5% compound (6) remaining). The reaction mixture was quenched by the addition of 2M HCl solution (126 kg) over 10 minutes at 20~25° C. (Note: The pH should be adjusted to be 1~2). The reaction solution was stirred for 30 min, settled, separated and the aqueous layer was removed. And the organic layer was first washed with water (1×202 kg), then 10% N-Acetylcysteine solution (1×258 kg), 7% NaHCO₃ aqueous solution (1×248 kg) and finally with 10% Na₂SO₄ aqueous solution (1×178 kg). The organic layer was treated with CUNO circulation (with 3M CUNO carbon filtration system) for 18 h to remove palladium impurities, then chase washed with MTBE (150 kg). The remaining organic layer (MTBE) was concentrated under vacuum to 3~4 volume below 30° C. And methanol (280 kg) was added and then distilled to 3~4 volume below 30° C. The resulting solution was directly used for the next step without further purification.

2-ethynyl-5-fluoro-4-methoxypyrimidine (2)

Potassium fluoride (244 g, 4.2 mol, 0.023 equiv) was added into compound (7)/methanol solution under N2, and then the mixture was stirred for 1~2 h at 20~30° C. until the reaction was completed (Note: IPC control: less than 0.5% compound (7) remaining). The reaction mixture was quenched by the addition of water (180 kg) over 10 minutes at 20~30° C. (Note: The quenching is slightly exothermic). The reaction mixture was concentrated under vacuum to 3~5 volume most methanol until distilled out (Note: the jacket temperature should be kept below 30° C.). Then MTBE (250 kg) was added into the mixture, stirred for 1 h, settled, separated. The organic layer was kept and the aqueous layer was re-extracted with MTBE (80 kg), settled, separated and the aqueous layer was discarded. The combined organic layer was washed with water (1×100 kg), and then the resulting organic layer was concentrated under vacuum to 3~4 volume (Note: the jacket temperature should be kept below 30° C.). Methyl cyclohexane (200 kg) was added and then distilled to 3~4 volume below 30° C. The resulting solution was cooled down to 0~5° C. and stirred for 3 h. The reaction slurry was filtered and the filter cake was washed with pre-cold Methyl cyclohexane (60 kg). The isolated wet cake was dried under vacuum at 20~30° C. for 24~48 h giving the title compound as off-white solid (20.1 kg, 83% yield, HPLC purity=99.8%, assay=97.8%). $^1$H NMR (400 MHz, CHLOROFORM-d) δ ppm 3.00 (d, J=0.86 Hz, 1H), 4.04 (s, 3H), 8.22 (d, J=2.69 Hz, 1H).

(E)-3-(5-fluoro-4-methoxypyrimidin-2-yl)-1-(isoxazol-3-yl)-3-(methoxy(methyl)amino)prop-2-en-1-one (4')

Compound (2) (20.0 kg, 128.6 mol, 1.0 equiv) and tetrahydrofuran (THF, 108 kg) were added into the reactor (R1) at 20~30° C. under N2. The mixture was stirred at 20~30° C. for 0.5-1 h until compound (2) was completely dissolved, then cooled down to −90~−75° C. (Note: compound (2) may be precipitated out at low temperature). n-Butyllithium solution, 2.5M in hexanes (39.0 kg, 139.2 mol, 1.08 equiv) was dropwise added to the reaction mixture over 11 h while maintaining the inner temperature below −85° C. (Note: The reaction was exothermic. The temperature should be kept below −75° C. to minimize polymerization byproduct. An off-white sticky suspension was observed during addition). After addition, a chase wash of THF (18 kg) was followed. Then the mixture was stirred at −85° C. for 2 h. N-Methoxy-N-methylisoxazole-3-carboxamide (5) (22.8 kg, 146.0 mol, 1.1 equiv) was charged to the reaction suspension via addition funnel over 3 h while maintaining the inner temperature below −80° C. (Note: The reaction was slightly exothermic, and the off-white suspension gradually turned into brown suspension.) After addition, a chase wash of THF (18 kg) was followed. Then the mixture was warmed to −70~−60° C. over 1 h, and then stirred at −70~−60° C. for 1.5 h. In the meantime, N,O-dimethylhydroxyamine hydrochloride (3.9 kg, 39.9 mol, 0.3 equiv), glacial acetic acid (8.0 kg, 133.2 mol, 1.03 equiv) and ethyl acetate (EtOAc) (190 kg) were added into another reactor (R2). The reaction mixture was stirred at 20~30° C. for 0.5~1 h to obtain a solution and cooled to 0~5° C., and then stirred at 0~5° C. for 0.5~6 h. The reaction mixture was transferred from R1 into the vigorously stirred acidic solution in R2 over 10~60 min while maintaining the inner temperature below 10° C. After transfer, a chase wash of EtOAc (92 kg) was followed to rinse R1 and combined into R2. Then 7% sodium bicarbonate solution (120 kg) was added to the reaction mixture in R2, and the mixture was warmed to 20~30° C., and then stirred at 20~30° C. for 0.5~1 h. (Note: The reaction was monitored by quenching the reaction mixture into acetonitrile/water, and IPC was reported). The two layers were separated and the aqueous layer was discarded. The organic layer was washed twice with 10% sodium sulfate solution (2×130 kg), and then filtered through Celite, followed by a chase wash of EtOAc (57 kg). The combined filtrate was concentrated under vacuum to 3~4 volume (Note: the jacket temperature should be kept below 40° C.). Methanol (170 kg) was added and then distilled to 3~5 volume below 40° C. The resulting solution was warmed to 60~70° C. and stirred for 0.5~1 h, and then gradually cooled down to 0~5° C. over 8~9 h. The reaction slurry was stirred at 0~5° C. for another 5~8 h, and then filtered, the filter cake was rinsed with pre-cold methanol. The isolated wet cake was dried under vacuum at 30~40° C. for 24~48 h giving the title compound as off-white solid (28.95 kg, 73% yield, HPLC purity=99.5%, assay=98.7%). $^1$H NMR (400 MHz, CHLOROFORM-d) δ ppm 3.03 (s, 3H), 3.71 (s, 3H), 3.99 (s, 3H), 6.46 (s, 1H), 6.55 (d, J=1.71 Hz, 1H), 8.30 (d, J=1.71 Hz, 1H), 8.34 (d, J=2.69 Hz, 1H).

What is claimed is:

1. A process of preparing a compound of Formula IA:

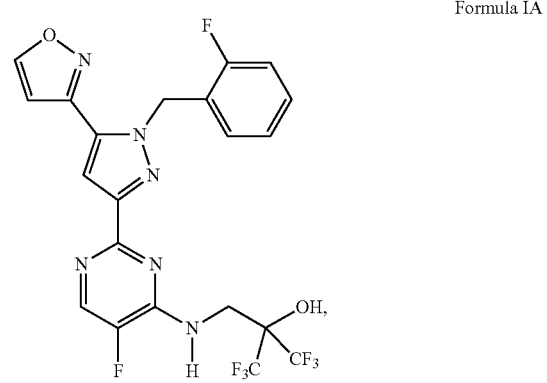 [SMILES: OC(CNc1nc(-c2cc(-c3ccon3)n(Cc3ccccc3F)n2)ncc1F)(C(F)(F)F)C(F)(F)F]

Formula IA comprising the step of:

i) coupling an amide of formula (1'):

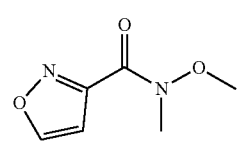

(1')

with a pyrimidine compound of formula (2):

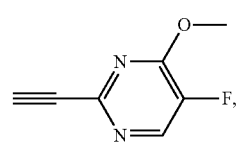

(2)

in an aprotic organic solvent in the presence of a base, to form, after quenching with acid, an intermediate of formula (3'):

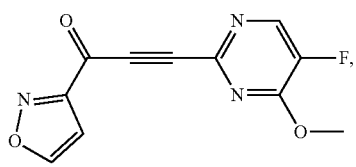
(3')

ii) at a pH>5, optionally in the presence of added N,O-dimethylhydroxylamine or a salt thereof, allowing the mixture to react to form the compound of formula (4'):

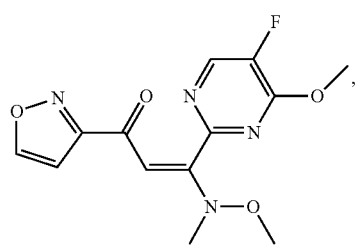
(4')

iii) condensing the compound of formula (4') with a hydrazine of formula

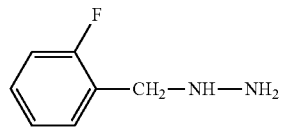

or a salt thereof, optionally in the presence of a base, to form a compound of Formula V:

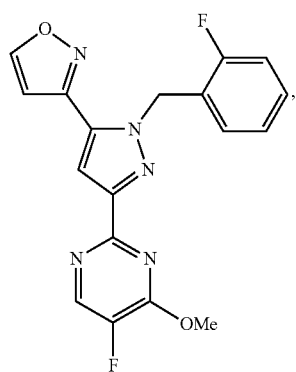
Formula V iv) de-methylating the compound of Formula V to form an alcohol compound of formula (9'):

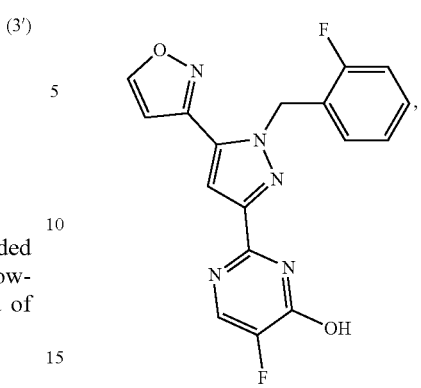
(9')

v) chlorinating the alcohol compound of formula (9') with phosphoryl chloride to form a compound of Formula VI:

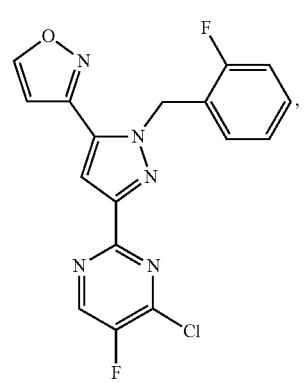
Formula VI vi) reacting an amine of formula (17):

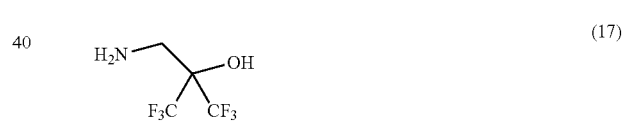
(17)

with the compound of Formula VI, optionally in the presence of a base, to yield the compound of Formula IA.

2. A process of preparing a compound of Formula IA:

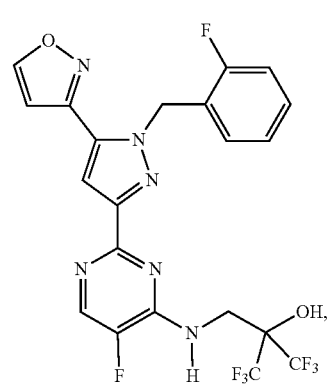
Formula IA comprising the step of:
i) coupling an amide of formula (1'):

(1')

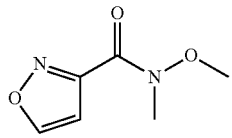

with a pyrimidine compound of formula (2):

(2)

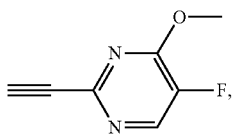

in an aprotic organic solvent in the presence of a base, to form, after quenching with an acid, an intermediate of formula (3'):

(3')

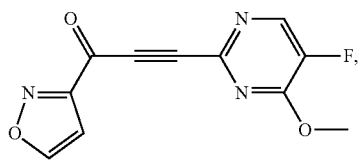

and
ii) at a pH>5, optionally in the presence of added N,O-dimethylhydroxylamine or a salt thereof, allowing the mixture to react to form the compound of formula (4'):

(4')

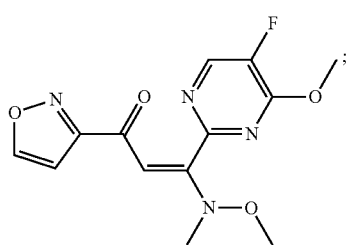

iiia) condensing the compound of formula (4') with hydrazine to form the compound of formula (24'):

(24')

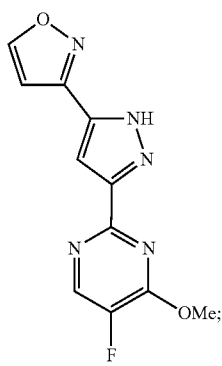

iiib) alkylating intermediate of formula (24') with an alkylating agent of formula (23A) to provide the compound of Formula V:

(23A)

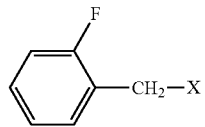

Formula V

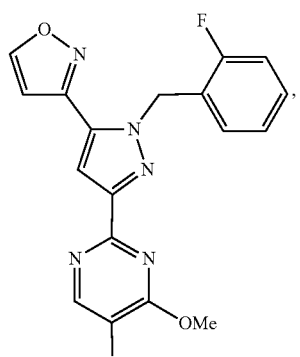

iv) de-methylating the compound of Formula V to form an alcohol compound of formula (9'):

(9')

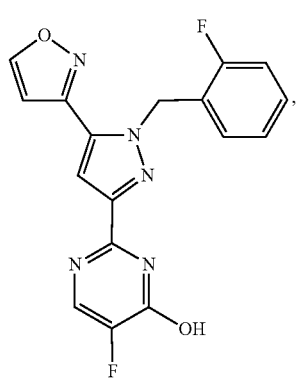

v) chlorinating the alcohol compound of formula (9') with phosphoryl chloride o form a compound of Formula VI:

Formula VI

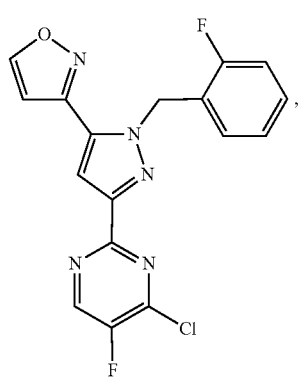

and
vi) reacting an amine of formula (17):

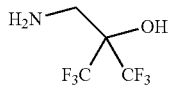
(17)

with the compound of Formula VIA, optionally in the presence of a base, to yield the compound of Formula IA, wherein X is a leaving group selected from —Br, —I, —Cl, —F, and a sulfonate ester.

3. The process of claim 1, wherein the process further comprises re-crystalization of the compound of Formula IA in a mixture of methanol and water.

4. The process of claim 3, wherein the re-crystallization comprises the steps of: A') dissolving the compound of Formula IA in methanol at a temperature between 30° C. and 65° C. to obtain a methanol solution of the compound of Formula IA; B') filtering the methanol solution of the compound of Formula IA from step A') to form a filtered methanol solution of the compound of Formula IA; C') adding water to the filtered methanol solution of the compound of Formula IA at a temperature between 50° C. and 60° C. to yield a slurry; D') cooling the slurry of step 3) to yield a recrystallized compound of Formula IA; and E') filtering and drying the recrystallized compound of Formula IA.

5. The process of claim 1, wherein the compound of formula (2) is prepared by a process comprising the steps of:
a) reacting dibromopyrimidine compound of formula (5):

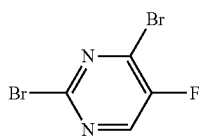
(5)

with a base in methanol or a methoxide salt in an aprotic solvent to form a bromopyrimidine compound of formula (6):

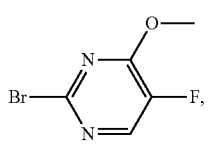
(6)

b) coupling the bromopyrimidine compound of formula (6) with ethynyltrimethylsilane, in an aprotic organic solvent in the presence of a base and a Pd catalyst, optionally in the presence of a Cu(I) catalyst, to form a compound of formula (7):

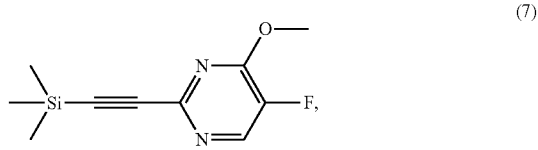
(7)

and
c) de-silylating the compound of formula (7) to form the pyrimidine compound of (2).

6. The process of claim 1, wherein the compound of formula (1') is prepared by reacting a carboxylic acid of formula (8')

(8')

with oxalyl chloride or an equivalent amide coupling reagent, followed by N,O-dimethylhydroxylamine or a salt thereof, in the presence of a base to form the amide of formula (1').

7. The process of claim 1, wherein the base in step i) is n-butyllithium.

8. The process of claim 1, wherein the process comprises contacting the reaction product of the reaction between the amide of formula (1') and the pyrimidine compound of formula (2) with a solution comprising N,O-dimethylhydroxylamine or a salt thereof and an acid to form the compound of formula (4').

9. The process of claim 8, wherein the solution comprises N,O-dimethylhydroxylamine hydrochloride.

10. The process of claim 8, wherein the acid is an aqueous acid.

11. The process of claim 10, wherein the acid is hydrochloric acid.

12. The process of claim 8, wherein the acid is glacial acetic acid.

13. The process of claim 2, wherein X is —Br.

14. The process of claim 2, wherein said salt of N,O-dimethylhydroxylamine is HCl salt; said hydrazine is hydrazine hydrate; and said sulfonate ester is mesylate, tosylate or triflate.

* * * * *